US007786273B2

(12) United States Patent
Tous et al.

(10) Patent No.: US 7,786,273 B2
(45) Date of Patent: Aug. 31, 2010

(54) MACROMOLECULES COMPRISING A THIOETHER CROSS-LINK

(75) Inventors: Guillermo I. Tous, East Windsor, NJ (US); Mark Schenerman, Reisterstown, MD (US); Ziping Wei, North Potomac, MD (US)

(73) Assignee: Medimmune, LLC, Gaithersburg, MD (US)

( * ) Notice: Subject to any disclaimer, the term of this patent is extended or adjusted under 35 U.S.C. 154(b) by 73 days.

(21) Appl. No.: 11/375,810

(22) Filed: Mar. 14, 2006

(65) Prior Publication Data
US 2006/0216284 A1  Sep. 28, 2006

Related U.S. Application Data

(60) Provisional application No. 60/661,724, filed on Mar. 14, 2005, provisional application No. 60/699,138, filed on Jul. 13, 2005.

(51) Int. Cl.
C07K 16/00 (2006.01)
C07K 16/08 (2006.01)
C07K 1/10 (2006.01)
A61K 39/395 (2006.01)
A61K 39/42 (2006.01)

(52) U.S. Cl. ............ 530/388.1; 530/402; 530/387.3; 530/388.9; 424/133.1; 424/139.1; 424/141.1; 424/147.1

(58) Field of Classification Search .......... 530/387.1, 530/387.3, 388.1, 388.15, 389.1, 388.9, 389.8, 530/402, 408
See application file for complete search history.

(56) References Cited

U.S. PATENT DOCUMENTS

2006/0123504 A1* 6/2006 Leavitt et al. ............. 800/19
2006/0286548 A1* 12/2006 Liposky et al. ............. 435/5

FOREIGN PATENT DOCUMENTS

| EP | 0 446 071 A2 | 9/1991 |
| EP | 1 174 126 A1 | 1/2002 |
| WO | WO 91/03493 | 3/1991 |
| WO | WO 93/03056 | 2/1993 |
| WO | WO 00/44788 | 8/2000 |

OTHER PUBLICATIONS

Glennie et al. Preparation and performance of bispecific F(ab')2 antibody containing thioether-linked Fab' gamma fragments. Journal of immunology 1987, vol. 139, pp. 2367-2375.*

(Continued)

*Primary Examiner*—Shafiqul Haq

(57) ABSTRACT

The present invention provides macromolecules comprising at least one thioether cross-link. A thioether cross-link comprising a single thioether bond between two residues of a macromolecule. The macromolecules of the invention can display enhanced stability, pharmaceutical properties and functional properties. In particular, the invention provides an isolated antibodies comprising at least one thioether cross-link that specifically bind to particular antigens. The present invention also provides a composition comprising a macromolecule substantially free of a denaturing reagent, wherein the macromolecule comprises at least one thioether cross-link. In addition, the present invention provides a method for producing the macromolecules and compositions of the invention.

16 Claims, 6 Drawing Sheets

OTHER PUBLICATIONS

Beavis et al., 1988, "A Novel Protein Cross-Linking Reaction in Stressed Neutral Protamine Hagedorn Formulations of Insulin," *Journal of Pharmaceutical Sciences*, 88(3):331-336 and *Journal of Pharmaceutical Sciences*, 88(8):842.

Brems et al., 1992, "Improved Insulin Stability Through Amino Acid Substitution," Protein Engineering, 5(6):519-525.

Brody et al., 1997, "Multistep Denaturation and Hierarchy of Disulfide Bond Cleavage of a Monoclonal Antibody," Anal. Biochem., 24:247-256.

Du Vigneaud et al., 1941, "The Formation of Lanthionine on Treatment of Insulin with Dilute Alkali," J. Biol. Chem., 141:707-708.

Forrer et al., 2004, "Chip-Based Gel Electrophoresis Method for the Quantification of Half-Antibody Species in IgG4 and their By-and Degradation Products," Anal. Biochm. 334:81-88.

Kroon et al., 1995, "Analysis of Monoclonal Antibodies by Sodium Dodecyl Sulfate-Capillary Gel Electrophoresis with Special Reference to Quantitation of Half-Antibody," J. Cap. Elec. 1:34-38.

McClellan et al. Jan. 11, 2005, "Detection and Characterization of a Non-Reducible Inter-Chain Cross-Link in a Recombinant Antibody," WCBP 2005, 9th Symposium on the Interface of Regulatory and Analytical Sciences for Biotechnology Health Products, Poster P-25-T.

Toren et al., 1988, "Determination of Interchain Crosslinkages in Insulin B-Chain Dimers by Fast Atom Bombardment Mass Spectrometry," Anal. Biochem. 169:287-299.

Tous et al., 2005, "Characterization of a Novel Modification to Monoclonal Antibodies: Thioether Cross-Link of Heavy and Light Chains," 2005, Anal. Chem..77:2675:2682.

Vasilyeva et al., 2005, "Development of a Chip-Based Capillary Gel Electrophoresis Method for Quantification of a Half-Antibody in Immunoglobulin $G_4$ Samples," Electrophoresis 25:3890-3896.

Zhang et al. Jan. 11, 2005, "Development of a Reversed Phase HPLC Method for Analysis of a HGS Monoclonal Antibody," WCBP 2005, 9th Symposium on the Interface of Regulatory and Analytical Sciences for Biotechnology Health Products, Poster P-47-W.

Finley JW, Friedman M. "New amino acid derivatives formed by alkaline treatment of proteins," Adv Exp Med Biol. 1977;86B:123-30.

Friedman M. Gumbmann MR, Masters PM, "Protein-alkali reactions: chemistry, toxicology, and nutritional consequences," Adv Exp Med Biol. 1984:177:367-412.

Friedman M, Chemistry, biochemistry, nutrition, and microbiology of lysinoalanine, lanthionine. and histidinoalanine in food and other proteins. J Agric Food Chem. Apr. 1999:47(4):1295-319.

Klostermeyer H. Reimerdes E, "Heat induced crosslinks in milk proteins and consequences for the milk system." Adv Exp Med Biol. 1977;86B:263-75.

Walsh RG. Nashef AS. Feeney RE, "Intramolecular cross-linking of proteins by formation of lysinoalanine or lanthionine. Modification of disulfides in ovomucoids," Int J Pept Protein Res. Oct. 1979:14(4):290-9.

European Search Report dated Nov. 18, 2009 for corresponding PCT/US2006/009311.

Kalofonos, H.P., et al., 1994, "Targeting of Tumours With Murine and Reshaped Human Monoclonal Antibodies Against Placental Alkaline Phosphatase: Immunolocalisation, Pharmacokinetics and Immune Response", European Journal of Cancer, 30A(112):1842-1850.

Schütt, C., et al., 1989, "Selective Killing of Human Monocytes by an Immunotoxin Containing Partially Denatured Mistletoe Lectin 1", International Society of Immunopharmacology,11(8):977-980.

Shen, Wei-Chang, 1990, "Acid-sensitive dissociation between poly(lysine) and histamine-modified poly(glutamate) as a model for drug-releasing from carriers in endosomers", Biochimica et Biophysics Acta., (Elsevier Science), 1034:122-124.

Youle, Richard J., et al., 1980, "Anti-Thy 1.2 monoclonal antibody linked to ricin is a potent cell-type-specific toxin," Medical Sciences, 77(9):5483-5486.

\* cited by examiner

SEQUENCE LISTING

<160> NUMBER OF SEQ ID NOS: 38

<210> SEQ ID NO 1
<211> LENGTH: 450
<212> TYPE: PRT
<213> ORGANISM: Artificial Sequence
<220> FEATURE:
<223> OTHER INFORMATION: Amino acid sequence derived from Murine monoclonal antibody and further modified by amino acid substitutions

<400> SEQUENCE: 1

```
Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Asp Lys Lys Asp Tyr Asn Pro Ser
 50                  55                  60

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 2
<211> LENGTH: 120
<212> TYPE: PRT
<213> ORGANISM: Artificial Sequence
<220> FEATURE:
<223> OTHER INFORMATION: Humanized antibody - VH Chain

<400> SEQUENCE: 2

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120

<210> SEQ ID NO 3
<211> LENGTH: 7
<212> TYPE: PRT
<213> ORGANISM: Murine

<400> SEQUENCE: 3

Thr Ser Gly Met Ser Val Gly
1               5

<210> SEQ ID NO 4
<211> LENGTH: 16
<212> TYPE: PRT
<213> ORGANISM: Murine

<400> SEQUENCE: 4

Asp Ile Trp Trp Asp Asp Lys Lys Asp Tyr Asn Pro Ser Leu Lys Ser
1               5                   10                  15
```

<210> SEQ ID NO 5
<211> LENGTH: 10
<212> TYPE: PRT
<213> ORGANISM: Murine

<400> SEQUENCE: 5

Ser Met Ile Thr Asn Trp Tyr Phe Asp Val
1               5                   10

<210> SEQ ID NO 6
<211> LENGTH: 213
<212> TYPE: PRT
<213> ORGANISM: Artificial Sequence
<220> FEATURE:
<223> OTHER INFORMATION: Humanized antibody - VL Chain

<400> SEQUENCE: 6

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 7
<211> LENGTH: 106
<212> TYPE: PRT
<213> ORGANISM: Artificial Sequence
<220> FEATURE:
<223> OTHER INFORMATION: Humanized antibody - VL Domain

<400> SEQUENCE: 7

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
             35                  40                  45

Asp Thr Ser Lys Leu Ala Ser Gly Val Pro Ser Arg Phe Ser Gly Ser
     50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
            100                 105

<210> SEQ ID NO 8
<211> LENGTH: 10
<212> TYPE: PRT
<213> ORGANISM: Murine

<400> SEQUENCE: 8

Lys Cys Gln Leu Ser Val Gly Tyr Met His
1               5                   10

<210> SEQ ID NO 9
<211> LENGTH: 7
<212> TYPE: PRT
<213> ORGANISM: Murine

<400> SEQUENCE: 9

Asp Thr Ser Lys Leu Ala Ser
1               5

<210> SEQ ID NO 10
<211> LENGTH: 9
<212> TYPE: PRT
<213> ORGANISM: Murine

<400> SEQUENCE: 10

Phe Gln Gly Ser Gly Tyr Pro Phe Thr
1               5

<210> SEQ ID NO 11
<211> LENGTH: 450
<212> TYPE: PRT
<213> ORGANISM: Artificial Sequence
<220> FEATURE:
<223> OTHER INFORMATION: Humanized antibody - VH Chain

<400> SEQUENCE: 11

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 12
<211> LENGTH: 120
<212> TYPE: PRT
<213> ORGANISM: Artificial Sequence
<220> FEATURE:
<223> OTHER INFORMATION: Humanized antibody - VH Chain

<400> SEQUENCE: 12

Gln Val Thr Leu Arg Glu Ser Gly Pro Ala Leu Val Lys Pro Thr Gln
1               5                   10                  15

```
Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser
        115                 120

<210> SEQ ID NO 13
<211> LENGTH: 7
<212> TYPE: PRT
<213> ORGANISM: Artificial Sequence
<220> FEATURE:
<223> OTHER INFORMATION: Amino acid sequence derived from Murine
      monoclonal antibody and further modified by amino acid
      substitutions

<400> SEQUENCE: 13

Thr Ala Gly Met Ser Val Gly
1               5

<210> SEQ ID NO 14
<211> LENGTH: 16
<212> TYPE: PRT
<213> ORGANISM: Artificial Sequence
<220> FEATURE:
<223> OTHER INFORMATION: Amino acid sequence derived from Murine
      monoclonal antibody and further modified by amino acid
      substitutions

<400> SEQUENCE: 14

Asp Ile Trp Trp Asp Asp Lys Lys His Tyr Asn Pro Ser Leu Lys Asp
1               5                   10                  15

<210> SEQ ID NO 15
<211> LENGTH: 10
<212> TYPE: PRT
<213> ORGANISM: Artificial Sequence
<220> FEATURE:
<223> OTHER INFORMATION: Amino acid sequence derived from Murine
      monoclonal antibody and further modified by amino acid
      substitutions

<400> SEQUENCE: 15

Asp Met Ile Phe Asn Phe Tyr Phe Asp Val
1               5                   10

<210> SEQ ID NO 16
<211> LENGTH: 213
<212> TYPE: PRT
<213> ORGANISM: Artificial Sequence
<220> FEATURE:
<223> OTHER INFORMATION: Humanized antibody - VL Chain

<400> SEQUENCE: 16

Asp Ile Gln Met Thr Gln Ser Pro Ser Thr Leu Ser Ala Ser Val Gly
1               5                   10                  15
```

```
Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
210

<210> SEQ ID NO 17
<211> LENGTH: 120
<212> TYPE: PRT
<213> ORGANISM: Artificial Sequence
<220> FEATURE:
<223> OTHER INFORMATION: Humanized antibody - VH Domain

<400> SEQUENCE: 17

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser
        115                 120

<210> SEQ ID NO 18
<211> LENGTH: 10
<212> TYPE: PRT
<213> ORGANISM: Artificial Sequence
```

```
<220> FEATURE:
<223> OTHER INFORMATION: Amino acid sequence derived from Murine
      monoclonal antibody and further modified by amino acid
      substitutions

<400> SEQUENCE: 18

Ser Ala Ser Ser Arg Val Gly Tyr Met His
1               5                   10

<210> SEQ ID NO 19
<211> LENGTH: 112
<212> TYPE: PRT
<213> ORGANISM: Homo sapiens

<400> SEQUENCE: 19

Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Glu Ala Ile Phe Thr Tyr Trp Gly Gln Gly Thr Leu Val Thr
            100                 105                 110

<210> SEQ ID NO 20
<211> LENGTH: 10
<212> TYPE: PRT
<213> ORGANISM: Homo sapiens

<400> SEQUENCE: 20

Gly Phe Thr Phe Ser Ser Tyr Thr Met Ser
1               5                   10

<210> SEQ ID NO 21
<211> LENGTH: 16
<212> TYPE: PRT
<213> ORGANISM: Homo sapiens

<400> SEQUENCE: 21

Thr Ile Ser Ser Gly Gly Thr Tyr Thr Tyr Tyr Pro Asp Ser Val Lys
1               5                   10                  15

<210> SEQ ID NO 22
<211> LENGTH: 6
<212> TYPE: PRT
<213> ORGANISM: Homo sapiens

<400> SEQUENCE: 22

Glu Ala Ile Phe Thr Tyr
1               5

<210> SEQ ID NO 23
<211> LENGTH: 107
<212> TYPE: PRT
<213> ORGANISM: Homo sapiens

<400> SEQUENCE: 23
```

-continued

```
Asp Ile Lys Met Thr Gln Ser Pro Ser Ser Met Tyr Ala Ser Leu Gly
 1               5                  10                  15

Glu Arg Val Thr Ile Thr Cys Lys Ala Ser Gln Asp Ile Asn Asn Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Lys Tyr Asp Glu Phe Pro Tyr
                85                  90                  95

Thr Phe Gly Gly Gly Thr Lys Leu Glu Ile Lys
            100                 105
```

<210> SEQ ID NO 24
<211> LENGTH: 11
<212> TYPE: PRT
<213> ORGANISM: Homo sapiens

<400> SEQUENCE: 24

```
Lys Ala Ser Gln Asp Ile Asn Asn Tyr Leu Ser
 1               5                  10
```

<210> SEQ ID NO 25
<211> LENGTH: 7
<212> TYPE: PRT
<213> ORGANISM: Homo sapiens

<400> SEQUENCE: 25

```
Arg Ala Asn Arg Leu Val Asp
 1               5
```

<210> SEQ ID NO 26
<211> LENGTH: 9
<212> TYPE: PRT
<213> ORGANISM: Homo sapiens

<400> SEQUENCE: 26

```
Leu Lys Tyr Asp Glu Phe Pro Tyr Thr
 1               5
```

<210> SEQ ID NO 27
<211> LENGTH: 5
<212> TYPE: PRT
<213> ORGANISM: Mus sp.

<400> SEQUENCE: 27

```
Glu Tyr Tyr Met Tyr
 1               5
```

<210> SEQ ID NO 28
<211> LENGTH: 17
<212> TYPE: PRT
<213> ORGANISM: Mus sp.

<400> SEQUENCE: 28

```
Arg Ile Asp Pro Glu Asp Gly Ser Ile Asp Tyr Val Glu Lys Phe Lys
 1               5                  10                  15

Lys
```

```
<210> SEQ ID NO 29
<211> LENGTH: 9
<212> TYPE: PRT
<213> ORGANISM: Mus sp.

<400> SEQUENCE: 29

Gly Lys Phe Asn Tyr Arg Phe Ala Tyr
1               5

<210> SEQ ID NO 30
<211> LENGTH: 16
<212> TYPE: PRT
<213> ORGANISM: Mus sp.

<400> SEQUENCE: 30

Arg Ser Ser Gln Ser Leu Leu His Ser Ser Gly Asn Thr Leu Asn Trp
1               5                   10                  15

<210> SEQ ID NO 31
<211> LENGTH: 7
<212> TYPE: PRT
<213> ORGANISM: Mus sp.

<400> SEQUENCE: 31

Leu Val Ser Lys Leu Glu Ser
1               5

<210> SEQ ID NO 32
<211> LENGTH: 9
<212> TYPE: PRT
<213> ORGANISM: Mus sp.

<400> SEQUENCE: 32

Met Gln Phe Thr His Tyr Pro Tyr Thr
1               5

<210> SEQ ID NO 33
<211> LENGTH: 10
<212> TYPE: PRT
<213> ORGANISM: Homo sapiens

<400> SEQUENCE: 33

Gly Gly Thr Phe Ser Tyr Tyr Trp Ile Glu
1               5                   10

<210> SEQ ID NO 34
<211> LENGTH: 16
<212> TYPE: PRT
<213> ORGANISM: Homo sapiens

<400> SEQUENCE: 34

Glu Ile Leu Pro Gly Ser Gly Thr Thr Asn Tyr Asn Glu Lys Phe Lys
1               5                   10                  15

<210> SEQ ID NO 35
<211> LENGTH: 13
<212> TYPE: PRT
<213> ORGANISM: Homo sapiens

<400> SEQUENCE: 35

Ala Asp Tyr Tyr Gly Ser Asp Tyr Val Lys Phe Asp Tyr
1               5                   10

<210> SEQ ID NO 36
```

```
<211> LENGTH: 11
<212> TYPE: PRT
<213> ORGANISM: Homo sapiens

<400> SEQUENCE: 36

Lys Ala Ser Gln His Val Gly Thr His Val Thr
1               5                   10

<210> SEQ ID NO 37
<211> LENGTH: 7
<212> TYPE: PRT
<213> ORGANISM: Homo sapiens

<400> SEQUENCE: 37

Gly Thr Ser Tyr Arg Tyr Ser
1               5

<210> SEQ ID NO 38
<211> LENGTH: 9
<212> TYPE: PRT
<213> ORGANISM: Homo sapiens

<400> SEQUENCE: 38

Gln Gln Phe Tyr Glu Tyr Pro Leu Thr
1               5
```

MACROMOLECULES COMPRISING A THIOETHER CROSS-LINK

This application claims the benefit of priority of U.S. provisional application Nos. 60/661,724 and 60/699,138, filed Mar. 14, 2005, and Jul. 13, 2005, respectively, the contents of which are hereby incorporated by reference in their entireties.

1. FIELD OF THE INVENTION

The present invention provides compositions comprising macromolecules, for instance, polypeptides, e.g., an antibody, that comprise at least one thioether cross-link. This novel class of macromolecules can display enhanced stability, pharmaceutical properties and functional properties. The invention also provides isolated antibodies comprising at least one thioether cross-link that specifically bind to particular antigens. In addition, the present invention provides methods for producing the macromolecules and compositions of the invention.

2. BACKGROUND OF THE INVENTION

Antibodies play a vital role in our immune response. They can inactivate viruses and bacterial toxins, and are essential in recruiting the complement system and various types of white blood cells to kill invading microorganisms and large parasites. Antibodies are synthesized exclusively by B lymphocytes and are produced in millions of forms, each with a different amino acid sequence and a different binding site for an antigen.

A typical antibody is a Y-shaped molecule with two identical heavy (H) chains (each containing about 440 amino acids) and two identical light (L) chains (each containing about 220 amino acids). Proteolytic enzymes, such as papain and pepsin, can split an antibody molecule into different characteristic fragments. Papain produces two separate and identical Fab fragments, each with one antigen-binding site, and one Fc fragment. Pepsin produces one F(ab')$_2$ fragment. Alberts et al., Molecular Biology of the Cell, 2nd ed., 1989, Garland Publishing, Inc.

Both L and H chains have a variable sequence at their amino-terminal ends but a constant sequence at their carboxyl-terminal ends. The L chains have a constant region of about 110 amino acids long and a variable region of the same size. The H chains also have a variable region of about 110 amino acids long, but the constant region of the H chains is about 330 or 440 amino acid long, depending on the class of the H chain. Alberts et al., Molecular Biology of the Cell, 2nd ed., 1989, Garland Publishing, Inc.

The association between the four chains involves both covalent and noncovalent interactions. The covalent interactions are disulfide bonds formed between the cysteine residues in the carboxyl terminus of the light chain and the $C_H1$ domain of the heavy chain and disulfide bonds formed between the cysteine residues in the hinge regions of the two heavy chains.

Natural immunoglobulins have been used in assays, diagnosis and, to a more limited extent, therapy. However, such uses, especially in therapy, have been hindered by the polyclonal nature of natural immunoglobulins. The advent of monoclonal antibodies of defined specificity increased the opportunities for therapeutic use. Therapeutic monoclonal antibodies usually contain some microheterogeneity resulting from post-translational modifications and degradation events that occur during the production process and throughout the shelf-life of the biopharmaceutical product. The present invention provides a novel modification of monoclonal antibodies.

Citation or discussion of a reference herein shall not be construed as an admission that such is prior art to the present invention.

3. SUMMARY OF THE INVENTION

The present invention provides macromolecules comprising a thioether cross-link. In some embodiments, the macromolecule is a polypeptide, either a monomer or a multi-chain polypeptide. In further embodiments, the polypeptide is an antibody. The antibodies of the present invention may be, but are not limited to polyclonal antibodies, monoclonal antibodies, Fab fragments, F(ab)' fragments, F(ab)'$_2$ fragments, single chain antibodies, human antibodies, humanized or chimeric antibodies, and epitope-binding fragments of any of the above.

Briefly, a thioether cross-link is a thioether comprising a single thioether bond between two residues of a macromolecule. In certain embodiments, the thioether cross-links have a structure according to formula I: —OOC—CH(NH—)—R$^1$—S—R$^2$—CH(NH—)—COO—, wherein R$^1$ and R$^2$ are independently side chains of macromolecular residues, such as amino acid residues. Preferred R$^1$ and R$^2$ groups include methylene, ethylene, propylene, and butylene. Particularly preferred is methylene.

In one aspect, the present invention provides a composition substantially free of a denaturing reagent comprising a polypeptide, wherein the polypeptide comprises at least one thioether cross-link. In some embodiments, the polypeptide is more than 2%, 5%, 10% or 15% of the polypeptide molecules in the composition. In certain embodiments, the polypeptide is an antibody.

The thioether cross-link can link any two residues of a polypeptide or of two polypeptide chains. For example, in certain embodiments, the residues involved in a thioether cross-link can be any pair of the following: a cysteine, aspartic acid, glutamic acid, histidine, methionine, tyrosine, or any other naturally or non-naturally occurring amino acid. In certain embodiments, the thioether links a cysteine residue of the heavy chain and a cysteine residue of the light chain. The cysteine residue can be in any region of the heavy chain or light chain. In certain embodiments, the cysteine residue of the heavy chain is in the $C_H1$ region and the cysteine residue of the light chain is in $C_L$ region. In one embodiment, the cysteine residue in the $C_H1$ region of the heavy chain is at the amino acid position 223 according to the Kabat numbering system, and the cysteine residue in the $C_L$ region of the heavy chain is at the amino acid position 213 according to the Kabat numbering system.

The thioether cross-link can be at any location of a macromolecule. For instance, the thioether cross-link can be inter-molecular or intra-molecular. In some embodiments, the thioether cross-link is intra-molecular. For example, the thioether cross-link can link two polypeptide chains of an antibody. In some embodiments, the thioether cross-link links a heavy chain and a light chain of the antibody.

The thioether cross-link can be located in any position of a polypeptide. For example, the thioether cross-link can be at the N-terminus, at the C-terminus, or between the N-terminus and C-terminus of a polypeptide chain. In some embodiments, the thioether cross-link is located between the N-terminus and C-terminus of a polypeptide chain.

In certain embodiments, the present invention provides a composition comprising an antibody or fragment thereof, wherein the antibody or fragment thereof comprises at least one thioether cross-link and wherein the antibody or fragment thereof specifically binds to one or more particular antigens.

In certain embodiments, the antibody of the present invention specifically binds to an antigen of respiratory syncytial virus (RSV). In some embodiments, the antibody comprises the amino acid sequence of the variable heavy ($V_H$) and variable light ($V_L$) chains of palivizumab or motavizumab. In other embodiments, the antibody comprises the amino acid sequence of the complementarity determining regions (CDRs) of the $V_H$ and $V_L$ chains of palivizumab or motavizumab.

In certain embodiments, the antibody of the present invention specifically binds to an antigen of human metapneumovirus (hMPV). In some embodiments, the antibody is a humanized antibody that specifically binds to an antigen of hMPV.

In certain embodiments, the antibody of the present invention specifically binds to integrin $\alpha_v\beta_3$. In some embodiments, the antibody comprises the amino acid sequence of the $V_H$ and $V_L$ chains of MEDI-522 (Vitaxin®). In other embodiments, the antibody comprises the amino acid sequence of the CDRs of the $V_H$ and $V_L$ chains of MEDI-522 (Vitaxin®).

In certain embodiments, the antibody of the present invention specifically binds to CD2. In some embodiments, the antibody comprises the amino acid sequence of the $V_H$ and $V_L$ chains of siplizumab. In other embodiments, the antibody comprises the amino acid sequence of the complementarity determining regions (CDRs) of $V_H$ and $V_L$ chains of siplizumab.

In certain embodiments, the antibody of the present invention specifically binds to CD19. In some embodiments, the antibody comprises the amino acid sequence of the $V_H$ and $V_L$ chains of MT103. In other embodiments, the antibody comprises the amino acid sequence of the CDRs of the $V_H$ and $V_L$ chains of MT103.

In certain embodiments, the antibody of the present invention specifically binds to an Eph receptor. In certain embodiments, the antibody of the present invention specifically binds to EphA2. In some embodiments, the antibody comprises the amino acid sequence of the $V_H$ and $V_L$ chains of EA2 or EA5. In other embodiments, the antibody comprises the amino acid sequence of the $V_H$ and $V_L$ chains of EA2 or EA5. In certain embodiments, the antibody of the present invention specifically binds to EphA4. In some embodiments, the antibody of the present invention specifically binds to EphB4.

In certain embodiments, the antibody of the present invention specifically binds to IL-9. In some embodiments, the antibody comprises the amino acid sequence of the $V_H$ and $V_L$ chains of MEDI-528. In other embodiments, the antibody comprises the amino acid sequence of the CDRs of the $V_H$ and $V_L$ chains of MEDI-528.

In certain embodiments, the present invention provides a composition comprising a fusion protein. In some embodiments, the fusion protein comprises an Fc domain of an antibody or a fragment thereof, wherein the Fc domain of Fc domain fragment comprises at least one thioether cross-link. In other embodiments, the fusion protein comprises an $C_H1$, $C_H2$, $C_H3$ and/or $C_L$ domain of an antibody, wherein the $C_H1$, $C_H2$, $C_H3$ or $C_L$ domain comprises at least one thioether cross-link. In another embodiments, the fusion protein comprises two, three or all of the domains of $C_H1$, $C_H2$, $C_H3$ or $C_L$.

In a further aspect, the present invention provides a composition substantially free of a denaturing reagent comprising a polypeptide, wherein the polypeptide comprises a lanthionine. A lanthionine residue is known to those skilled in the art, as a sulfur bridged alanine dimer, having the structure of (—OOC—CH(NH—)—CH$_2$—S—CH$_2$—CH(NH—)—COO—). In some embodiments, the polypeptide is more than 2%, 5%, 10% or 15% of the polypeptide molecules of the composition. In certain embodiments, the polypeptide is an antibody. The antibodies in the composition may be, but are not limited to polyclonal antibodies, monoclonal antibodies, Fab fragments, F(ab)' fragments, F(ab)'$_2$ fragments, single chain antibodies, human antibodies, humanized or chimeric antibodies, and epitope-binding fragments of any of the above. The lanthionine can be located in any position of a polypeptide. For example, the thioether cross-link can be at the N-terminus, at the C-terminus, or between the N-terminus and C-terminus of a polypeptide chain.

In a further aspect, the present invention provides a composition substantially free of a denaturing reagent comprising a population of antibodies, i.e., two, three, four, five or more antibodies, wherein at least 2%, 5%, 10%, 15% or 20% of the antibodies comprise at least one thioether cross-link. In some embodiments, about 2-20%, 2-15%, 2-10%, 2-5%, 5-20%, 10-15%, 10-30%, 20-30%, 10-40%, 10-50%, 20-50% or 10-75% of the antibodies comprise at least one thioether cross-link.

In certain embodiments, at least 2%, 5%, 10%, 15% or 20% of the antibodies comprise at least two thioether cross-link. In some embodiments, about 2-20%, 2-15%, 2-10%, 2-5%, 5-20%, or 10-15% of the antibodies comprise at least two thioether cross-link.

In certain embodiments, the composition is a pharmaceutical composition. In some embodiments, the pharmaceutical composition further comprises a pharmaceutically acceptable carriers.

In certain embodiments, populations of antibodies all have the same amino acid sequence of $V_H$ and $V_L$ chains. In some embodiments, populations of antibodies all have the same CDRs of $V_H$ and $V_L$ chains.

In certain embodiments, populations of antibodies have different amino acid sequence of $V_H$ and $V_L$ chains. In some embodiments, populations of antibodies have different CDRs of $V_H$ and $V_L$ chains.

The invention provides a composition substantially free of a denaturing reagent comprising a population of fusion proteins, i.e. two, three, four, five or more fusion proteins, wherein at least 2%, 5%, 10%, 15% or 20% of the fusion proteins comprise an Fc domain or a fragment thereof comprising at least one thioether cross-link. In some embodiments, about 2-20%, 2-15%, 2-10%, 2-5%, 5-20%, 10-15%, 10-30%, 20-30%, 10-40%, 10-50%, 20-50% or 10-75% of the antibodies comprise at least one thioether cross-link. In certain embodiments, the population of fusion proteins have the same amino acid sequence. In other embodiments, the population of fusion proteins have different amino acid sequences. In a specific embodiment, the composition is a pharmaceutical composition.

The present invention provides a composition comprising a population of antibodies, i.e., two, three, four, five or more antibodies, wherein less than 2%, 1.5%, 1% or 0.5% of the antibodies in the population comprise a thioether cross-link. In certain embodiments, the population of the antibodies have the same amino acid sequences. In other embodiments, the population of antibodies have different amino acid sequences. In a specific embodiment, the composition is a pharmaceutical composition.

The present invention provides a composition a population of fusion proteins, i.e., two, three, four, five or more fusion proteins, wherein less than 2%, 1.5%, 1% or 0.5% of the fusion proteins in the population comprise a thioether cross-link. In certain embodiments, the population of antibodies have the same amino acid sequences. In other embodiments, the population of fusion proteins have different amino acid sequences. In a specific embodiment, the composition is a pharmaceutical composition.

In another aspect, the present invention provides an isolated antibody, wherein the antibody comprises at least one thioether cross-link, that binds to one or more particular antigens. In certain embodiments, the antibody of the present invention specifically binds to an antigen of respiratory syncytial virus (RSV). In some embodiments, the antibody comprises the amino acid sequence of the variable heavy ($V_H$) and variable light (VL) chains of palivizumab or motavizumab. In other embodiments, the antibody comprises the amino acid sequence of the complementarity determining regions (CDRs) of the $V_H$ and $V_L$ chains of palivizumab or motavizumab.

In certain embodiments, the antibody of the present invention specifically binds to an antigen of human metapneumovirus (hMPV). In some embodiments, the antibody is a humanized antibody that specifically binds to an antigen of hMPV.

In certain embodiments, the antibody of the present invention specifically binds to integrin $\alpha_v\beta_3$. In some embodiments, the antibody comprises the amino acid sequence of the $V_H$ and $V_L$ chains of MEDI-522 (Vitaxin®). In other embodiments, the antibody comprises the amino acid sequence of the CDRs of the $V_H$ and $V_L$ chains of MEDI-522 (Vitaxin®).

In certain embodiments, the antibody of the present invention specifically binds to CD2. In some embodiments, the antibody comprises the amino acid sequence of the $V_H$ and $V_L$ chains of siplizumab. In other embodiments, the antibody comprises the amino acid sequence of the complementarity determining regions (CDRs) of $V_H$ and $V_L$ chains of siplizumab.

In certain embodiments, the antibody of the present invention specifically binds to CD19. In some embodiments, the antibody comprises the amino acid sequence of the $V_H$ and $V_L$ chains of MT103. In other embodiments, the antibody comprises the amino acid sequence of the CDRs of the $V_H$ and $V_L$ chains of MT103.

In certain embodiments, the antibody of the present invention specifically binds to an Eph receptor. In certain embodiments, the antibody of the present invention specifically binds to EphA2. In some embodiments, the antibody comprises the amino acid sequence of the $V_H$ and $V_L$ chains of EA2 or EA5. In other embodiments, the antibody comprises the amino acid sequence of the CDRs of the $V_H$ and $V_L$ chains of EA2 or EA5. In certain embodiments, the antibody of the present invention specifically binds to EphA4. In some embodiments, the antibody of the present invention specifically binds to EphB4.

In certain embodiments, the antibody of the present invention specifically binds to IL-9. In some embodiments, the antibody comprises the amino acid sequence of the $V_H$ and $V_L$ chains of MEDI-528. In other embodiments, the antibody comprises the amino acid sequence of the CDRs of the $V_H$ and $V_L$ chains of MEDI-528.

In another aspect, the present invention provides a fusion protein comprising at least one thioether cross-link. In some embodiments, the fusion protein comprises an Fc domain of an antibody or a fragment thereof, wherein the Fc domain or Fc domain fragment comprises at least one thioether cross-link. In other embodiments, the fusion protein comprises an $C_H1$, $C_H2$, $C_H3$ and/or $C_L$ domain of an antibody, wherein the $C_H1$, $C_H2$, $C_H3$ or $C_L$ domain comprises at least one thioether cross-link. In another embodiments, the fusion protein comprises two, three or all of the domains of $C_H1$, $C_H2$, $C_H3$ or $C_L$.

In another aspect, the present invention provides a method for increasing the amount of an antibody in a composition, wherein the antibody comprises at least one thioether cross-link. The antibody in the composition can be any antibody comprising at least one thioether cross-link as described herein. In certain embodiments, the method comprises incubating the composition at a temperature greater than 4° C., or at pH greater than 7, for a time sufficient to increase the amount of said antibody species. In some embodiments, the method further comprises contacting the composition with a reducing agent.

In a further aspect, the present invention provides a method for producing a composition enriched in an antibody, wherein the antibody comprises at least one thioether cross-link. The antibody in the composition can be any antibody comprising at least one thioether cross-link as described herein. In certain embodiments, the method of the invention comprises incubating the composition at a temperature greater than 4° C., or at pH greater than 7, for a time sufficient to enrich said antibody species. In some embodiments, the method further comprises contacting the composition with a reducing agent.

In another aspect, the present invention provides a method for decreasing the amount of an antibody in a composition, wherein said antibody comprises at least one thioether cross-link in a composition resulting from a purification method. In certain embodiments, the method comprises reducing in pH and/or temperature of at least one step of said purification method resulting in a lower level of said antibody comprising at least one thioether cross-link than said first purification method.

In a further aspect, the present invention provides a method for producing a composition enriched in a fusion, wherein the fusion protein comprises at least one thioether cross-link. The fusion protein in the composition can be any fusion protein comprising at least one thioether cross-link as described herein. In certain embodiments, the method of the invention comprises incubating the composition at a temperature greater than 4° C., or at pH greater than 7, for a time sufficient to enrich said fusion protein species. In some embodiments, the method further comprises contacting the composition with a reducing agent.

In another aspect, the present invention provides a method for decreasing the amount of a fusion protein in a composition, wherein said fusion protein comprises at least one thioether cross-link in a composition resulting from a purification method. In certain embodiments, the method comprises reducing in pH and/or temperature of at least one step of said purification method resulting in a lower level of said fusion protein comprising at least one thioether cross-link than said first purification method.

4. BRIEF DESCRIPTION OF THE FIGURES

FIGS. 1A-1C show reducing CGE (panel A) and SDS-PAGE (panel B) analysis of a IgG1 monoclonal antibody. Lane 1 is molecular weight markers; Lane 2 and Lane 3 are a reduced monoclonal antibody. Panel C shows the graphical view of the heavy chain, light chain and 92 kDa cross-linked species.

Figure 4A:
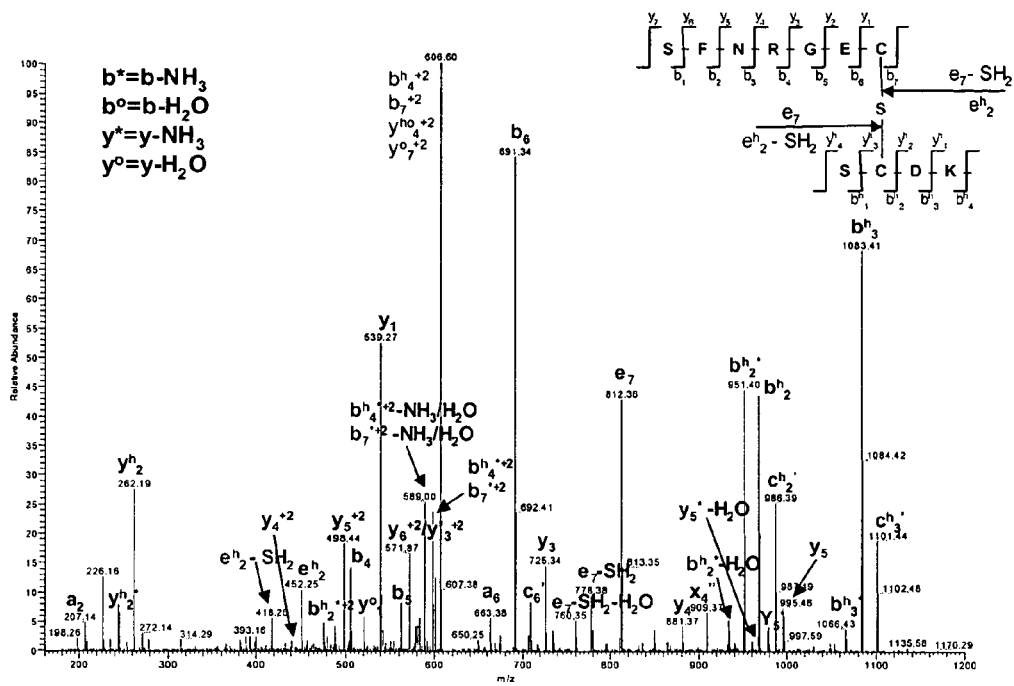
Figure 4B:
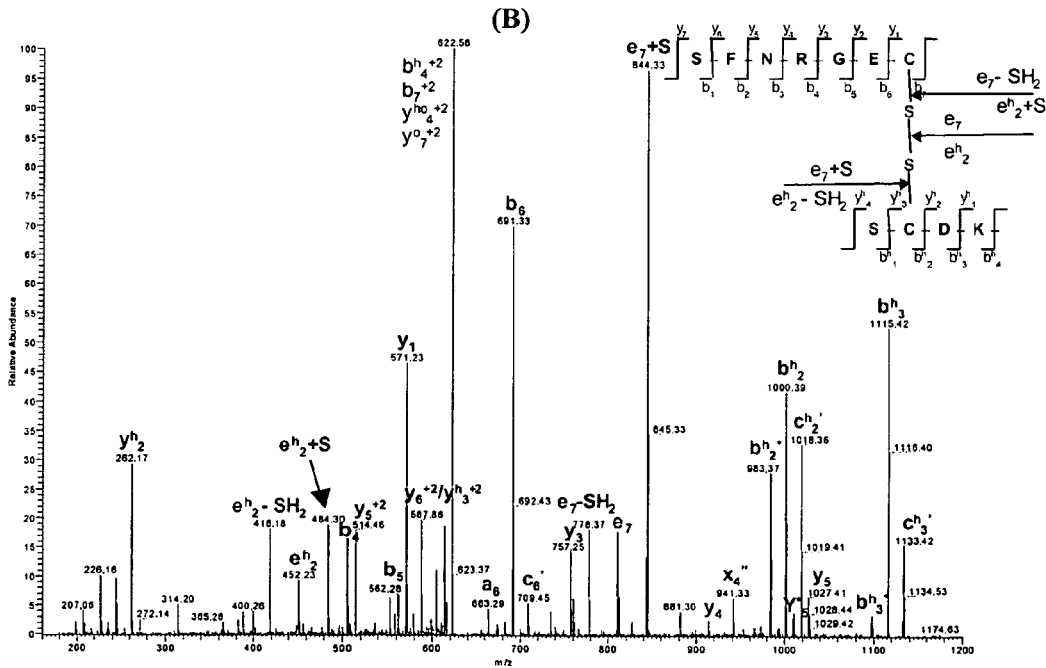

FIGS. 4A and 4B show MS/MS spectra and assignment of fragment ions of the cross-linked peptide of L19-L20 (SFN-RGEC) and H19 (SCDK) with a thioether bond linkage (ion at m/z 615.6$^{+2}$) (panel A) and a disulfide bond linkage (ion at m/z 631.6$^{+2}$) (panel B). Note: "e" in the figure refers to the side chain cleavage on the Cys and not the amino acid backbone. "2" refers to the Cys in the CSDK peptide chain. "7" refers to the Cys in the SFRNGEC peptide chain.

FIGS. 5A and 5B show deconvoluted mass spectra of the Fab fragment of a monoclonal antibody stored at 4° C. (panel A) and at 40° C. (panel B).

5. DETAILED DESCRIPTION OF THE INVENTION

The present invention is based, in part, on the discovery and characterization of a non-reducible thioether bridge between the heavy and light chains of different monoclonal antibodies. Accordingly, the invention provides macromolecules comprising a thioether cross-link, wherein the thioether cross-link is a thioether comprising a single thioether bond linking two residues of a macromolecule.

5.1. Definitions

As used herein, the term "isolated" in the context of a proteinaceous agent (e.g., peptide, polypeptide, fusion protein or antibody) refers to a proteinaceous agent which is substantially free of cellular material or contaminating proteins from the cell or tissue source from which it is derived, or substantially free of chemical precursors or other chemicals when chemically synthesized. The language "substantially free of cellular material" includes preparations of a proteinaceous agent in which the proteinaceous agent is separated from cellular components of the cells from which it is isolated or recombinantly produced. Thus, a proteinaceous agent that is substantially free of cellular material includes preparations of a proteinaceous agent having less than about 30%, 20%, 10%, or 5% (by dry weight) of heterologous protein (also referred to herein as a "contaminating protein"). When the proteinaceous agent is recombinantly produced, it is also preferably substantially free of culture medium, i.e., culture medium represents less than about 20%, 10%, or 5% of the volume of the protein preparation. When the proteinaceous agent is produced by chemical synthesis, it is preferably substantially free of chemical precursors or other chemicals, i.e., it is separated from chemical precursors or other chemicals which are involved in the synthesis of the proteinaceous agent. Accordingly such preparations of a proteinaceous agent have less than about 30%, 20%, 10%, 5% (by dry weight) of chemical precursors or compounds other than the proteinaceous agent of interest.

As used herein, the term "humanized antibody" refers to forms of non-human (e.g., murine) antibodies that are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to an EphA2 polypeptide, that has been altered by the introduction of amino acid residue substitutions, deletions or additions (i.e., mutations). In some embodiments, a humanized antibody is a derivative. Such a humanized antibody comprises amino acid residue substitutions, deletions or additions in one or more non-human CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated). For further details in humanizing antibodies, see European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, *Molecular Immunology* 28(4/5):489-498; Studnicka et al., 1994, *Protein Engineering* 7(6):805-814; Roguska et al., 1994, *PNAS* 91:969-973; Tan et al., 2002, *J. Immunol.* 169: 1119-25; Caldas et al., 2000, *Protein Eng.* 13:353-60; Morea et al., 2000, *Methods* 20:267-79; Baca et al., 1997, *J. Biol. Chem.* 272:10678-84; Roguska et al., 1996, *Protein Eng.* 9:895-904; Couto et al., 1995, *Cancer Res.* 55 (23 Supp): 5973s-5977s; Couto et al., 1995, *Cancer Res.* 55:1717-22; Sandhu, 1994, *Gene* 150:409-10; Pedersen et al., 1994, *J. Mol. Biol.* 235:959-73; Jones et al., 1986, *Nature* 321:522-525; Reichmann et al., 1988, *Nature* 332:323-329; and Presta, 1992, *Curr. Op. Struct. Biol.* 2:593-596, and Wu et al., U.S. Pat. Application. Publication. No. 2005/0042664, published Feb. 24, 2004.

As used herein, the terms "single-chain Fv" or "scFv" refer to antibody fragments comprise the VH and VL domains of antibody, wherein these domains are present in a single polypeptide chain. Generally, the Fv polypeptide further comprises a polypeptide linker between the VH and VL domains which enables the scFv to form the desired structure for antigen binding. For a review of sFv see Pluckthun in *The Pharmacology of Monoclonal Antibodies*, vol. 113, Rosenburg and Moore eds. Springer-Verlag, New York, pp. 269-315 (1994). In specific embodiments, scFvs include bispecific scFvs and humanized scFvs.

As used herein, the term "antigen" refers to a macromolecule that is recognized by antibodies and can trigger an immune response. An antigen can be a protein or a polysaccharide, but it can also be any type of molecule, even small molecules if coupled to a larger carrier.

As used herein, the term "epitopes" refers to fragments of a polypeptide or protein having antigenic or immunogenic activity in an animal, preferably in a mammal, and most preferably in a human. An epitope having immunogenic activity is a fragment of a polypeptide or protein that elicits an antibody response in an animal. An epitope having antigenic activity is a fragment of a polypeptide or protein to which an antibody immunospecifically binds as determined by any method well-known to one of skill in the art, for example by immunoassays. Antigenic epitopes need not necessarily be immunogenic.

As used herein, the terms "protein" and the term "polypeptide," used interchangeably, to refer to a complex organic compound composed of amino acid residues joined by peptide bonds.

As used herein, the term "specifically binds to an antigen" and analogous terms refer to peptides and polypeptides (e.g., fusion proteins and antibodies) that specifically bind to an antigen or a fragment thereof and do not specifically bind to other antigens. A peptide or polypeptide (e.g., fusion proteins and antibodies) that specifically binds to an antigen may bind to other peptides or polypeptides with lower affinity as determined by, e.g., immunoassays, BIAcore, or other assays known in the art. Peptides and polypeptides (e.g., fusion proteins and antibodies) that specifically bind to an antigen may cross-reactive with related antigens. Preferably, antibodies that specifically bind to an antigen do not cross-react with other antigens.

When describing the macromolecules, compositions containing such macromolecules and methods of using such macromolecules and compositions, the following terms have the following meanings unless otherwise indicated.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkenylene, alkynyl and alkynylene. Aliphatic groups typically have from 1 or 2 to about 12 carbon atoms.

"Alkyl" refers to monovalent saturated aliphatic hydrocarbyl groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyl" as defined below.

"Alkylene" refers to divalent saturated aliphatic hydrocarbyl groups particularly having up to about 11 carbon atoms and more particularly 1 to 6 carbon atoms which can be straight-chained or branched. This term is exemplified by groups such as methylene (—CH2-), ethylene (—CH2CH2-), the propylene isomers (e.g., —CH2CH2CH2- and —CH(CH3)CH2-) and the like.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Aralkyl" or "arylalkyl" refers to an alkyl group, as defined above, substituted with one or more aryl groups, as defined above.

"Amino" refers to the radical —NH$_2$.

"Aminocarbonyl" or "amido" refers to the group —C(O)NRR where each R is independently hydrogen, alkyl, aryl and cycloalkyl, or where the R groups are joined to form an alkylene group.

"Carbamoyl" refers to the radical —C(O)N(R)$_2$ where each R group is independently hydrogen, alkyl, cycloalkyl or aryl, as defined herein, which may be optionally substituted as defined herein.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" or "heteroaromatic" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, -carboline, chromane, chromene, cinnoline, furan, imidazole, indazole, indole, indoline, indolizine, isobenzofuran, isochromene, isoindole, isoindoline, isoquinoline, tetrahydroisoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, tetrahydroquinoline, quinolizine, quinoxaline, tetrazole, thiadiazole, thiazole, thiophene, triazole, xanthene, and the like. Particularly, heteroaryl can include other saturated ring systems, and can therefore be derived from indoline, indolizine, tetrahydroquinoline, and tetrahydroisoquinoline. Preferably, the heteroaryl group is between 5-20 membered heteroaryl, with 5-10 membered heteroaryl being particularly preferred. Particular heteroaryl groups are those derived from thiophene, pyrrole, benzothiophene, benzofuran, indole, pyridine, pyrimidine, quinoline, tetrahydroquinoline, isoquinoline, tetrahydroisoquinoline, imidazole, oxazole and pyrazine.

"Hetero substituent" refers to a halo, O, S or N atom-containing functionality that may be present as an R4 in a CR4 group present as substituents directly on W or Z of the compounds of this invention or may be present as a substituent in the "substituted" aryl, heteroaryl and aliphatic groups present in the compounds.

Examples of hetero substituents include:
-halo,
—NO$_2$, —NH$_2$, —NHR, —N(R)$_2$,
—NRCOR, —NRSOR, —NRSO$_2$R, OH, CN, CO$_2$R,
—COOH,
—O—R,
—CON(R)$_2$, —CONROR,
—SO$_3$H, —S—R, —SO$_2$N(R)$_2$,
—S(O)R, and —S(O)$_2$R, wherein each R is independently an aryl or aliphatic, optionally with substitution. Among hetero substituents containing R groups, preference is given to those materials having aryl and alkyl R groups as defined herein. Where feasible, each R may include hydrogen. Also, where feasible, two R groups when on same atom may join to form a heterocyclic ring of 3-8 atoms. For example, two R groups of NR2, SO2NR2, and CONR2 may join, together with the N atom, to form a N-morpholino, N-pyrrolo, N-piperidino, and N-pyrazolylo ring. Preferred hetero substituents are those listed above.

As used herein, the term "thioether cross-link" refers to a single thioether bond between two residues of a macromolecule. For purpose of this invention, the two residues of the macromolecules are linked by a single sulfur atom. Links that comprise two or more sulfur atoms, for instance, disulfide bridges, are not thioether cross-links of the present invention. A preferred thioether cross-link can be found in a lanthionine residue, where a single sulfur atom bridges the side chains of two amino acids. Other links having a single sulfur atom are described herein in detail. As will be recognized by those skilled in the art, the formation of a thioether cross-link can result in the loss of one or more atoms, such as a sulfur or hydrogen atoms, from one or both of the residues. Certain thioether cross-links have a structure according to formula I: —OOC—CH(NH—)—$R^1$—S—$R^2$—CH(NH—)—COO—, wherein $R^1$ and $R^2$ are independently side chains of macromolecule residues, such as amino acid residues. The residue can be natural or non-natural. In certain embodiments, $R^1$ and $R^2$ can lose one or more atoms, for instance, sulfur or hydrogen atoms in the formation of the thioether cross-link. Preferred $R^1$ and $R^2$ groups include methylene, ethylene, propylene, and butylene. Particularly preferred is methylene. The term "thioether cross-link" is intended to be interchangeable with the term "zero-order thioether" of provisional application No. 60/661,724, the contents of which are incorporated by reference in its entirety.

As used herein, a compositions that is "substantially free of a denaturing reagent" refers to a composition free of denaturing reagent or having only denaturing reagents in such an amount that macromolecules in the compositions maintain their three-dimensional structures. In certain embodiments, at least 50% of the macromolecules in the composition are in their native states.

As used herein, the term "disease" or "disorder," used interchangeably, refers to a condition, e.g., a pathogenic condition, in a subject.

As used herein, the terms "therapies" and "therapy" (e.g., a prophylactic agent or a therapeutic agent) can refer to any protocol(s), method(s) and/or agent(s) that can be used in the prevention, treatment, management or amelioration of a disorder or one or more symptoms thereof.

As used herein, the terms "prophylactic agent" and "prophylactic agents" refer to any agent(s) which can be used in the prevention of a disorder, or prevention of recurrence or spread of a disorder.

As used herein, the terms "prophylactically effective amount" may refer to the amount of prophylactic agent sufficient to prevent the recurrence or spread of a disease or the occurrence of such in a patient, including but not limited to those predisposed to the disease. A prophylactically effective amount may also refer to the amount of the prophylactic agent that provides a prophylactic benefit in the prevention of disease. Further, a prophylactically effective amount with respect to a prophylactic agent of the invention means that amount of prophylactic agent alone, or in combination with other agents, that provides a prophylactic benefit in the prevention of disease.

As used herein, the terms "therapeutic agent" and "therapeutic agents" refer to any agent(s) which can be used in the treatment, management or amelioration a disorder or one or more symptoms thereof.

As used herein, a "therapeutically effective amount" refers to that amount of the therapeutic agent sufficient to treat or manage a disorder or a symptom thereof. A therapeutically effective amount may refer to the amount of a therapy sufficient to delay or minimize the onset of disorder, e.g., delay or minimize the spread of cancer. A therapeutically effective amount may also refer to the amount of the therapy that provides a therapeutic benefit in the treatment or management of a disorder. A therapeutically effective amount may also refer to the amount of the therapy that reduces the progression, severity and/or duration in the treatment or management of a disorder.

As used herein, the terms "prevent", "preventing" and "prevention" in the context of the administration of a therapy, refer to the prevention of the recurrence or onset of a disorder or one or more symptoms thereof in a subject as result of the administration of a prophylactic or therapeutic agent.

As used herein, the terms "treat," "treating" and "treatment" in the context of the administration of a therapy refer to the reduction or amelioration of the progression, severity, and/or duration of a disorder or the eradication, reduction or amelioration of symptoms of a disorder, (e.g., the eradication, removal, modification, or control of primary, regional, or metastatic cancer tissue) that results from the administration of one or more therapies. In certain embodiments, such terms refer to the minimizing or delaying the spread of cancer resulting from the administration of one or more therapeutic agents to a subject with such a disease.

As used herein, the terms "manage", "managing" and "management" in the context of the administration of a therapy, refer to the beneficial effects that a subject derives from a therapy, which does not result in a cure of the disorder. In certain embodiments, a subject is administered one or more therapy to "manage" a disorder so as to prevent the progression or worsening of the disorder (i.e., hold disease progress).

As used herein, the term "in combination" refers to the use of one or more therapies. The use of the term "in combination" does not restrict the order in which prophylactic and/or therapeutic agents are administered to a subject with a disorder. A first therapies can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapies to a subject with a disorder.

As used herein, the terms "subject" and "patient" are used interchangeably. As used herein, a subject is preferably a mammal such as a non-primate (e.g., cows, pigs, horses, cats, dogs, rats etc.) and a primate (e.g., monkey and human), most preferably a human.

5.2. Macromolecules Comprising Thioether Cross-Links

As discussed in detail in the section below, the present invention provides macromolecules that comprise a thioether cross-link, and compositions comprising the macromolecules. The prevent invention also provides methods of using the macromolecules. Further, the present invention provides methods of producing and using the compositions comprising the macromolecules.

The macromolecules of the present invention can be any type of macromolecule as recognized by those skilled in the art. In some embodiments, the macromolecules of the present invention are polypeptides. The macromolecules of the present invention can be any type of polypeptides recognized by those skilled in the art, such as enzymes, antibodies, membrane-associated proteins, or secreted proteins, etc. In certain embodiments, the present invention encompasses cytokines, including but not limited to interleukins and interferons. In another embodiments, the present invention encompasses membrane-associated proteins, for instance, receptors or ion channels. In yet another embodiments, the present invention provides antibodies, wherein said antibodies comprises a thioether cross-link.

A thioether cross-link is any thioether bond that meets a definition provided herein. As discussed above, a thioether cross-link is a link between residues of a polypeptide, wherein the link has a single sulfur atom. Significantly, thioether cross-links expressly do not include links that comprise more than one sulfur atom, such as disulfide bridges that are familiar to those of skill in the art. Instead, a thioether cross-link has a single sulfur atom that bridges residues of a macromolecule.

The atoms that bridge residues of a macromolecule are those atoms that link one residue to another residue as recognized by those of skill in the art. In preferred embodiments, these atoms consist of the smallest number of atoms that connect a portion of one residue of the macromolecule to other residues of the macromolecule. In preferred embodiments, the atoms that bind residues of a macromolecule are not backbone atoms, as understood by those skilled in the art. These atoms form a thioether cross-link when they comprise no more than a single sulfur atom.

For instance, in certain embodiments, the thioether cross-link links the side chains of residues of the macromolecules. The atoms that link one side chain to the other side chains should comprise no more than a single sulfur atom. When the linked side chains comprise a single sulfur atom, the side chains are linked by a thioether cross-link. In certain embodiments, the residues may comprise other sulfur atoms so long as the other sulfur atoms are not necessary to bridge the residues. In further embodiments, the residues comprise only a single sulfur atom.

The residues linked by the thioether cross-link can be natural residues or non-natural residues. Formation of the thioether cross-link can result in the loss of atoms from the residues, as will be recognized by those of skill in the art. For instance, formation of a thioether cross-link between side chains of two cysteine residues can result in the loss of a sulfur atom and hydrogen atoms from the residues, yet the resulting thioether cross-link will be recognized as linking the cysteine residues by one of skill in the art.

The thioether cross-link can link any two residues of a polypeptide. In preferred embodiments, the residues linked by the thioether cross-link are natural residues. In particular embodiments, one or both of the residues are selected from the group consisting of cysteine, aspartic acid, glutamic acid, histidine, methionine and tyrosine. In further embodiments, two of the residues are selected from the group consisting of cysteine, aspartic acid, glutamic acid, histidine, methionine and tyrosine. In preferred embodiments, two of the residues are cysteine residues.

The macromolecule of the present invention can comprise one or more thioether cross-links. In some embodiments, the macromolecule comprises only one thioether cross-link. In other embodiments, the macromolecule comprises two, three or more thioether cross-links.

In certain embodiments the thioether cross-link has the structure of formula (I): —OOC—CH(NH—)—$R^1$—S—$R^2$—CH(NH—)—COO—, or any salt or solvate thereof. In formula I, the dashes indicate bonds. The dashes from the carboxy and amino groups can be bonds to other portions of the macromolecule or to hydrogen or to groups known to those of skill in the art to modify amino or carboxy termini of macromolecules. $R^1$ and $R^2$ are each independently side chains of natural or non-natural amino acids that would result from the formation of the thioether cross-link of formula I. In certain embodiments, each of $R^1$ and $R^2$ is independently selected from the group consisting of a bond, alkyl, heteroalkyl, aryl, arylalkyl, heteroaryl, heteroarylalkyl, alkylacyl, alkylamino and alkylacylamino. The sulfur can be bonded to any atom of $R^1$ and $R^2$ where chemically feasible as will be recognized by those of skill in the art. In preferred embodiments, each of $R^1$ and $R^2$ is independently $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl or C alkyl. In particularly preferred embodiments, each of $R^1$ and $R^2$ is independently methylene.

The thioether cross-link can be at any location of the macromolecule where feasible according to the knowledge of those of skill in the art. For instance, the thioether cross-link can be inter-molecular or intra-molecular. In some embodiments, the thioether cross-link is inter-molecular. For example, the thioether cross-link can link two polypeptide chains of an antibody. In some embodiments, the thioether cross-link links a heavy chain and a light chain of the antibody. In other embodiments, the thioether cross-link links two heavy chains or two light chains of the antibody.

Within a polypeptide chain, a residue of the thioether cross-link can be located in any position apparent to those of skill in the art. In some embodiments, a residue of the thioether cross-link is located at the N-terminus of a polypeptide. In other embodiments, a residue of the thioether cross-link is located at the C-terminus of a polypeptide. In further embodiments, a residue the thioether cross-link is located between the N-terminus and C-terminus of a polypeptide. In some embodiments, the thioether cross-link can link a residue in the middle of a polypeptide to a residue at the N or C-terminus of a polypeptide. In a particular embodiment, the thioether cross-link can link the residue at the N-terminus of a polypeptide, to the residue at the C-terminus of the same polypeptide thereby forming a cyclic polypeptide.

In certain antibody embodiments, the thioether links a cysteine residue of a heavy chain and a cysteine residue of a light chain. The cysteine residues can be in any region of the heavy chain or light chain. In certain embodiments, the cysteine residue of the heavy chain is in the $C_H1$ region and the cysteine residue of the light chain is in $C_L$ region. In one embodiment, the cysteine residue in the $C_H1$ region of the heavy chain is at the amino acid position 223, and the cysteine residue in the $C_L$ region of the heavy chain is at the amino acid position 213.

In certain embodiments, the present invention provides a macromolecule comprising lanthionine or a composition comprising a macromolecule, wherein the macromolecule comprises lanthionine. As will be recognized by those of skill in the art, lanthionine is a sulfide bridged alanine dimer (—OOC—CH(NH—)—$CH_2$—S—$CH_2$—CH(NH—)—COO—). Lanthionine, and macromolecules comprising lanthionine, can be prepared by methods described herein or by methods apparent to those of skill in the art. For instance, lanthionine can be prepared from cysteine and dehydroalanine, or from cysteine and cysteine, by post-translational modification of peptides. In certain embodiments, the macromolecule is a polypeptide, In further embodiments, the polypeptide is an antibody.

In some embodiments, polypeptides, preferably, antibodies, can be modified to incorporate a thioether cross-link according to the invention. For example, any residue can be substituted with a cysteine by techniques known to those of skill in the art. For instance, standard techniques can be used to introduce mutations in the nucleotide sequence encoding an antibody, or fragment thereof, including, e.g., site-directed mutagenesis and PCR-mediated mutagenesis, which results in amino acid substitutions. In a preferred embodiments, one or more non-essential amino acid residues of the polypeptide can be substituted with a cysteine. In certain embodiments, the antibody one or more non-essential amino acid residues substituted with a cysteine. In certain embodiments, the substitutions with a cysteine are conservative amino acid substitution made at one or more predicted non-essential amino acid residues (i.e., amino acid residues which are not critical for the antibody to immunospecifically bind to an antigen). A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

5.3. Compositions Comprising Macromolecules that Comprise Thioether Cross-Link In one aspect, the prevent invention provides compositions substantially free of a denaturing reagent comprising a macromolecule, wherein said macromolecule comprises at least one thioether cross-link. In certain embodiments, the macromolecule comprises two, three, four, five or more thioether cross-links. In other embodiments, the macromolecules comprise 1-3, 1-5, 2-5, 2-4, 1-10, 5-10, or 2-6 thioether cross-links. In some embodiments, the macromolecules are polypeptides. In some further embodiments, the macromolecules are antibodies. The antibodies comprising at least one thioether cross-link are described in detail in Section 5.2 and 5.4.

A composition that is "substantially free of a denaturing reagent" refers to a composition free of any denaturing reagent or having only denaturing reagents in such an amount that macromolecules in the compositions maintain their three-dimensional structures and thus their characteristic folded structures. In some embodiments, at least 50% of the macromolecules in the composition are in their native states. In some embodiments, at least 60% of the macromolecules in the composition are in their native states. In some embodiments, at least 70% of the macromolecules in the composition are in their native states. In some embodiments, at least 80% of the macromolecules in the composition are in their native states. In some embodiments, at least 90% of the macromolecules in the composition are in their native states. In some embodiments, at least 95% of the macromolecules in the composition are in their native states. In some embodiments, at least 99% of the macromolecules in the composition are in their native states. In some embodiments, about 50%-99.99%, 50%-99%, 50%-95%, 50%-90%, 50%-80%, 50%-70%, 50%-60%, 60%-99%, 70%-99%, 80%-99%, 90%-99%, 60%-95%, or 70%-90% of the macromolecules in the composition are in their native states.

A denaturing reagent is any reagent that might cause a structure change in an macromolecule, including but limited to acids, bases or detergents. Exemplary denaturing reagents include, for example, sodium dodecyl sulfate, urea, and guanidine. The amount of denaturing reagents in the composition to be qualified as "substantially free of a denaturing reagent" depends on the nature of the denaturing reagents and the particular antibodies in the composition. The stronger the denaturing reagents, the less the denaturing reagent should be in the composition. In some embodiments, the denaturing reagents are less than 50% of the composition. In some embodiments, the denaturing reagents are less than 25% of the composition. In some embodiments, the denaturing reagents are less than 10% of the composition. In some embodiments, the denaturing reagents are less than 5% of the composition. In some embodiments, the denaturing reagents are less than 2.5% of the composition. In some embodiments, the denaturing reagents are less than 1% of the composition. In some embodiments, the denaturing reagents are less than 0.5% of the composition. In some embodiments, the denaturing reagents are less than 0.25% of the composition. In some embodiments, the denaturing reagents are less than 0.1% of the composition. In some embodiments, the denaturing reagents are about 0.1%-50%, 0.1%-25%, 0.1%-10%, 0.1%-5%, 0.1%-2.5%, 0.1%-1%, 0.1%-0.5%, 0.1%-0.25%, 0.25%-50%, 0.25%-25%, 0.5%-10%, or 0.5%-1% of the composition.

In some embodiments, the macromolecules comprising at least one thioether cross-link are more than 2%, 5%, 10%, 15%, 25%, 35%, 45%, 50% or 75% of the total macromolecules in the composition. In certain embodiments, the macromolecules comprising at least one thioether cross-link are more than 2% of the total macromolecules in the composition. In certain embodiments, the macromolecules comprising at least one thioether cross-link are more than 5% of the total macromolecules in the composition. In certain embodiments, the macromolecules comprising at least one thioether cross-link are more than 10% of the total macromolecules in the composition. In certain embodiments, the macromolecules comprising at least one thioether cross-link are more than 15% of the total macromolecules in the composition. In some embodiments, the macromolecules comprising at least one thioether cross-link are about 2%-15%, 2%-10%, 2%-5%, 5%-15%, 5%-10%, 10%-15%, 10-30%, 20-30%, 10-40%, 10-50%, 20-50% or 10-75% of the total macromolecules in the composition.

In other embodiments, the macromolecules comprising at least one thioether cross-link are less than 4%, 2%, 1%, 0.75%, 0.5%, 0.25%, 0.1% and 0.05% of the total macromolecules in the composition. In certain embodiments, the macromolecules comprising at least one thioether cross-link are less than 4% of the total macromolecules in the composition. In certain embodiments, the macromolecules comprising at least one thioether cross-link are less than 2% of the total macromolecules in the composition. In certain embodiments, the macromolecules comprising at least one thioether cross-link are less than 1% of the total macromolecules in the composition. In certain embodiments, the macromolecules comprising at least one thioether cross-link are less than 0.75% of the total macromolecules in the composition. In certain embodiments, the macromolecules comprising at least one thioether cross-link are less than 0.5% of the total macromolecules in the composition. In certain embodiments, the macromolecules comprising at least one thioether cross-link are less than 0.25% of the total macromolecules in the composition. In certain embodiments, the macromolecules comprising at least one thioether cross-link are less than 0.1% of the total macromolecules in the composition. In certain embodiments, the macromolecules comprising at least one thioether cross-link are less than 0.05% of the total macromolecules in the composition. In some embodiments, the macromolecules comprising at least one thioether cross-link are about 0.05%-4%, 0.05%-2%, 0.05%-1%, 0.05%-0.5%, 0.05%-0.25%, 0.05%-0.1%, 0.1%-4%, 0.25%-2%, 0.5%-1% of the total macromolecules in the composition.

In a further aspect, the present invention provides compositions substantially free of a denaturing reagent comprising an antibody, wherein the antibody comprises at least one thioether cross-link and wherein the antibody specifically binds to one or more particular antigens. In another aspect, the present invention provides an isolated antibody that comprises at least one thioether cross-link, wherein the antibody specifically binds to one or more particular antigens.

In certain embodiments, the antibody of the present invention specifically binds to an antigen of respiratory syncytial virus (RSV). In some embodiments, the antibody comprises the amino acid sequence of the variable heavy ($V_H$) and variable light (VL) chains of palivizumab or motavizumab. In other embodiments, the antibody comprises the amino acid sequence of the complementarity determining regions (CDRs) of the $V_H$ and $V_L$ chains of palivizumab or motavizumab.

In certain embodiments, the antibody of the present invention specifically binds to an antigen of human metapneumovirus (hMPV). In some embodiments, the antibody is a humanized antibody that specifically binds to an antigen of hMPV.

In certain embodiments, the antibody of the present invention specifically binds to integrin $\alpha_v\beta_3$. In some embodiments, the antibody comprises the amino acid sequence of the $V_H$ and $V_L$ chains of MEDI-522 (Vitaxin®). In other embodiments, the antibody comprises the amino acid sequence of the CDRs of the $V_H$ and $V_L$ chains of MEDI-522 (Vitaxin®).

In certain embodiments, the antibody of the present invention specifically binds to CD2. In some embodiments, the antibody comprises the amino acid sequence of the $V_H$ and $V_L$ chains of siplizumab. In other embodiments, the antibody comprises the amino acid sequence of the complementarity determining regions (CDRs) of $V_H$ and $V_L$ chains of siplizumab.

In certain embodiments, the antibody of the present invention specifically binds to CD 19. In some embodiments, the antibody comprises the amino acid sequence of the $V_H$ and $V_L$ chains of MT103. In other embodiments, the antibody comprises the amino acid sequence of the CDRs of the $V_H$ and $V_L$ chains of MT103.

In certain embodiments, the antibody of the present invention specifically binds to an Eph receptor. In certain embodiments, the antibody of the present invention specifically binds to EphA2. In some embodiments, the antibody comprises the amino acid sequence of the CDRs of the $V_H$ and $V_L$ chains of EA2 or EA5. In other embodiments, the antibody comprises the amino acid sequence of the $V_H$ and $V_L$ chains of EA2 or EA5. In certain embodiments, the antibody of the present invention specifically binds to EphA4. In some embodiments, the antibody of the present invention specifically binds to EphB4.

In certain embodiments, the antibody of the present invention specifically binds to IL-9. In some embodiments, the antibody comprises the amino acid sequence of the $V_H$ and $V_L$ chains of MEDI-528. In other embodiments, the antibody comprises the amino acid sequence of the CDRs of the $V_H$ and $V_L$ chains of MEDI-528.

Particular antibodies comprising at least one thioether cross-link are described in detail in Section 5.4 below.

In a further aspect, the present invention provides a composition substantially free of a denaturing reagent comprising a population of antibodies, i.e., two, three, four, five or more antibodies, wherein at least 2%, 5%, 10%, 15% or 20% of the antibodies comprise at least one thioether cross-link. In some embodiments, about 2-20%, 2-15%, 2-10%, 2-5%, 5-20%, 10-15%, 10-30%, 20-30%, 10-40%, 10-50%, 20-50% or 10-75% of the antibodies comprise at least one thioether cross-link.

In certain embodiments, at least 2%, 5%, 10%, 15% or 20% of the antibodies comprise at least two thioether cross-link. In some embodiments, about 2-20%, 2-15%, 2-10%, 2-5%, 5-20%, 10-15%, 10-30%, 20-30%, 10-40%, 10-50%, 20-50% or 10-75% of the antibodies comprise at least two thioether cross-link.

In certain embodiments, the composition is a pharmaceutical composition. In some embodiments, the pharmaceutical composition further comprises a pharmaceutically acceptable carriers.

In certain embodiments, populations of antibodies all have the same amino acid sequence of $V_H$ and $V_L$ chains. In some embodiments, populations of antibodies all have the same CDRs of $V_H$ and $V_L$ chains.

In certain embodiments, populations of antibodies have different amino acid sequence of $V_H$ and $V_L$ chains. In some embodiments, populations of antibodies have different CDRs of $V_H$ and $V_L$ chains.

The present invention provides a composition comprising a fusion protein. In some embodiments, the fusion protein comprises an Fc domain of an antibody or a fragment thereof, wherein the Fc domain or Fc domain fragment comprises at least one thioether cross-link. In other embodiments, the fusion protein comprises an $C_H1$, $C_H2$, $C_H3$ and/or $C_L$ domain of an antibody, wherein the $C_H1$, $C_H2$, $C_H3$ or $C_L$ domain comprises at least one thioether cross-link. In another embodiments, the fusion protein comprises two, three or all of the domains of $C_H1$, $C_H2$, $C_H3$ or $C_L$.

The present invention provides a composition substantially free of a denaturing reagent, the composition comprising a population of fusion proteins, i.e., two, three, four, five or more fusion proteins, wherein at least 2%, 5%, 10%, 15% or 20% of the fusion proteins comprise at least one thioether cross-link. In certain embodiments, the fusion proteins comprises an Fc domain or a fragment thereof, wherein the thioether cross-link is in the Fc domain or Fc domain fragment. In other embodiments, the fusion proteins comprise a $C_H1$, $C_H2$, $C_H3$ and/or $C_L$ domain, wherein the domain comprises the thioether cross-link.

The present invention provides a composition substantially free of a denaturing reagent, the composition comprising a population of antibodies, i.e., two, three, four, five or more antibodies, wherein less than 2%, 1.5%, 1% or 0.5% of the antibodies in the population comprise a thioether cross-link. In certain embodiments, the population of antibodies have the same amino acid sequences. In other embodiments, the population of antibodies have different amino acid sequences. In a specific embodiment, the composition is a pharmaceutical composition.

The present invention provides a composition substantially free of a denaturing reagent, the composition comprising a population of fusion proteins, i.e., two, three, four, five or more fusion proteins, wherein less than 2%, 1.5%, 1% or 0.5% of the fusion proteins in the population comprise a thioether cross-link. In some embodiments, the fusion proteins comprise an Fc domain or a fragment thereof, wherein the thioether cross-link is in the Fc domain or Fc domain fragment. In other embodiments, the fusion proteins comprise a $C_H1$, $C_H2$, $C_H3$ and/or $C_L$ domain, wherein the domain comprises the thioether cross-link. In certain embodiments, the population of antibodies have the same amino acid sequences. In other embodiments, the population of fusion proteins have different amino acid sequences. In a specific embodiment, the composition is a pharmaceutical composition.

5.3.1 Pharmaceutical Compositions and Formulations

The invention provides compositions comprising macromolecules, for instance, polypeptides (e.g., an antibody or a fusion protein) of the invention for use in diagnosing, detecting, or monitoring a disorder, in preventing, treating, managing, or ameliorating of a disorder or one or more symptoms thereof, and/or in research. In a specific embodiment, a composition comprises one or more antibodies or fusion proteins of the invention. In another embodiment, a composition comprises one or more antibodies fusion proteins of the invention and one or more prophylactic or therapeutic agents other than antibodies fusion proteins of the invention. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The compositions of the invention include, but are not limited to, bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention are pharmaceutical compositions and comprise an effective amount of one or more antibodies of the invention, a pharmaceutically acceptable carrier, and, optionally, an effective amount of another prophylactic or therapeutic agent.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is contained in or administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The pharmaceutical composition can be formulated as an oral or non-oral dosage form, for immediate or extended release. The composition can comprise inactive ingredients ordinarily used in pharmaceutical preparation such as diluents, fillers, disintegrants, sweeteners, lubricants and flavors. The pharmaceutical composition is preferably formulated for intravenous administration, either by bolus injection or sustained drip, or for release from an implanted capsule. A typical formulation for intravenous administration utilizes physiological saline as a diluent.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The composition of the present invention can also include printed matter that describes clinical indications for which the antibodies can be administered as a therapeutic agent, dosage amounts and schedules, and/or contraindications for administration of the antibodies of the invention to a patient.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In particular, the invention also provides that one or more of the prophylactic or therapeutic agents, or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the invention is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

Generally, the ingredients of the compositions of the invention are derived from a subject that is the same species origin or species reactivity as recipient of such compositions. Thus, in a preferred embodiment, human or humanized antibodies are administered to a human patient for therapy or prophylaxis.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

The compositions of the invention may be administered topically. Such compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

The compositions of the invention may be administered intranasally. Such composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

The compositions of the invention may be administered orally. Such compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The compositions of the invention may be used for pulmonary administration, e.g., by use of an inhaler or nebulizer. Such compositions can be formulated with an aerosolizing agent. See, e.g., U.S. Pat. Nos. 6,019,968, 5,985, 320, 5,985, 309, 5,934,272, 5,874,064, 5,855,913, 5,290,540, and 4,880, 078; and PCT Publication Nos. WO 92/19244, WO 97/32572, WO 97/44013, WO 98/31346, and WO 99/66903, each of which is incorporated herein by reference their entireties. In a specific embodiment, macromolecules of the invention, combination therapy, and/or composition of the invention is administered using Alkermes AIR™ pulmonary drug delivery technology (Alkermes, Inc., Cambridge, Mass.).

The compositions of the invention may be formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The compositions of the invention can be formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

5.3.2 Methods of Administration

Various delivery systems are known and can be used to administer one or more antibodies of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidurala administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985, 320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, for a description of pulmonary administration, each of which is incorporated herein by reference their entireties. In one embodiment, an antibody of the invention, combination therapy, or a composition of the invention is administered using Alkermes AIR™ pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies of the invention is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the prophylactic or therapeutic agent can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. No. 5,679,377; U.S. Pat. No. 5,916,597; U.S. Pat. No. 5,912, 015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more therapeutic agents of the invention. See, e.g., U.S. Pat. No. 4,526, 938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entireties.

In a specific embodiment, where the composition of the invention is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868). Alternatively, a nucleic acid can be introduced intracellularly and incorporated within host cell DNA for expression by homologous recombination.

5.3.3 Dosage and Frequency of Administration

The amount of a prophylactic or therapeutic agent or a composition of the present invention which will be effective in the treatment, management, prevention, or amelioration of a disorder or one or more symptoms thereof can be determined by standard clinical. The frequency and dosage will vary according to factors specific for each patient depending on the specific therapy or therapies (e.g., the specific therapeutic or prophylactic agent or agents) administered, the severity of the disorder, disease, or condition, the route of administration, as well as age, body, weight, response, the patient's immune status, and the past medical history of the patient. For example, the dosage of a prophylactic or therapeutic agent or a composition of the invention which will be effective in the treatment, prevention, management, or amelioration of a disorder or one or more symptoms thereof can be determined by administering the composition to an animal model such as, e.g., the animal models disclosed herein or known to those skilled in the art. In addition, in vitro assays may optionally be employed to help identify optimal dosage ranges. Suitable regimens can be selected by one skilled in the art by considering such factors and by following, for example, dosages reported in the literature and recommended in the Physician's Desk Reference (57th ed., 2003).

The toxicity and/or efficacy of the prophylactic and/or therapeutic protocols of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapies that exhibit large therapeutic indices are preferred. While therapies that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any therapy used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

For macromolecules comprising at least one thioester cross-link of the present invention, the dosage administered to a patient is typically 0.01 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human and humanized antibodies have a longer half-life within the human body than antibodies from other species due to the immune response to the foreign polypeptides. Thus, lower dosages of human antibodies and less frequent administration is often possible.

Exemplary doses of a small molecule include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

The dosages of prophylactic or therapeutically agents are described in the Physicians' Desk Reference (56th ed., 2002).

5.4. Antibodies of the Present Invention

The antibodies of the present invention include, but are not limited to, monoclonal antibodies, synthetic antibodies, multispecific antibodies (including bi-specific antibodies), human antibodies, humanized antibodies, chimeric antibodies, single-chain Fvs (scFv) (including bi-specific scFvs), single chain antibodies, Fab fragments, F(ab') fragments, disulfide-linked Fvs (sdFv), and epitope-binding fragments of any of the above. In particular, antibodies of the present invention include immunoglobulin molecules and immunologically active portions of immunoglobulin molecules, i.e., molecules that contain an antigen binding site that immunospecifically binds to an antigen. The immunoglobulin molecules of the invention can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule. Preferably, the antibodies of the invention are IgG, more preferrably, $IgG_1$.

In certain embodiments, the antibodies of the invention comprise four polypeptide chains—two light chains and two heavy chains. In other embodiments, the antibodies of the invention comprise a $V_H$ chain and/or a $V_L$ chain. In yet another embodiments, the antibodies of the present invention are epitope-binding fragments.

Throughout the present specification, the numbering of the residues in an IgG light or heavy chain is that of the EU index as in Kabat et al., Sequences of Proteins of Immunological Interest, 5th Ed. Public Health Service, NH1, MD (1991), expressly incorporated herein by references. The "EU index as in Kabat" refers to the numbering of the human IgG1 EU antibody.

The antibodies of the invention may be from any animal origin including birds and mammals (e.g., human, murine, donkey, sheep, rabbit, goat, guinea pig, camel, horse, or chicken). Preferably, the antibodies are human or humanized monoclonal antibodies. As used herein, "human" antibodies include antibodies having the amino acid sequence of a human immunoglobulin and include antibodies isolated from human immunoglobulin libraries or from mice or other animal that express antibodies from human genes.

The antibodies of the present invention may be monospecific, bispecific, trispecific or of greater multispecificity. Multispecific antibodies may immunospecifically bind to different epitopes of a polypeptide or may immunospecifically bind to both a polypeptide as well a heterologous epitope, such as a heterologous polypeptide or solid support material. See, e.g., International Publication Nos. WO 93/17715, WO 92/08802, WO 91/00360, and WO 92/05793; Tutt, et al., 1991, J. Immunol. 147:60-69; U.S. Pat. Nos. 4,474,893, 4,714,681, 4,925,648, 5,573,920, and 5,601,819; and Kostelny et al., 1992, J. Immunol. 148:1547-1553.

The antibodies of the invention include derivatives of the antibodies known to those of skill in the art. Standard techniques known to those of skill in the art can be used to introduce mutations in the nucleotide sequence encoding an antibody to be used with the methods of the invention, including, for example, site-directed mutagenesis and PCR-mediated mutagenesis which result in amino acid substitutions. Preferably, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a preferred embodiment, the derivatives have conservative amino acid substitutions are made at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

The antibodies of the present invention include derivatives that are modified, i.e, by the covalent attachment of any type of molecule to the antibody such that covalent attachment. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, synthesis in the presence of tunicamycin, etc. Additionally, the derivative may contain one or more non-classical amino acids.

The present invention also provides antibodies of the invention that comprise a framework region known to those of skill in the art. In certain embodiments, one or more framework regions, preferably, all of the framework regions, of an antibody to be used in the methods of the invention or fragment thereof are human. In certain other embodiments of the invention, the fragment region of an antibody of the invention is humanized. In certain embodiments, the antibody to be used with the methods of the invention is a synthetic antibody, a monoclonal antibody, an intrabody, a chimeric antibody, a human antibody, a humanized chimeric antibody, a humanized antibody, a glycosylated antibody, a multispecific antibody, a human antibody, a single-chain antibody, or a bispecific antibody.

In certain embodiments of the invention, the antibodies of the invention have half-lives in a mammal, preferably a human, of greater than 12 hours, greater than 1 day, greater than 3 days, greater than 6 days, greater than 10 days, greater than 15 days, greater than 20 days, greater than 25 days, greater than 30 days, greater than 35 days, greater than 40 days, greater than 45 days, greater than 2 months, greater than 3 months, greater than 4 months, or greater than 5 months. Antibodies or antigen-binding fragments thereof having increased in vivo half-lives can be generated by techniques known to those of skill in the art. For example, antibodies or antigen-binding fragments thereof with increased in vivo half-lives can be generated by modifying (e.g., substituting, deleting or adding) amino acid residues identified as involved in the interaction between the Fc domain and the FcRn receptor (see, e.g., PCT Publication No. WO 97/34631, U.S. patent application Ser. No. 10/020,354, entitled "Molecules with Extended Half-Lives, Compositions and Uses Thereof", filed Dec. 12, 2001, by Johnson et al., and U.S. patent application Ser. No. 11/263,230, filed Oct. 31, 2005, entitled "Methods of Preventing and Treating RSV Infections and Related Conditions," by Losonsky, which are incorporated herein by reference in their entireties). Such antibodies or antigen-binding fragments thereof can be tested for binding activity to an antigens as well as for in vivo efficacy using methods known to those skilled in the art, for example, by immunoassays described herein.

Further, antibodies with increased in vivo half-lives can be generated by attaching to said antibodies or antibody fragments polymer molecules such as high molecular weight polyethyleneglycol (PEG). PEG can be attached to said antibodies with or without a multifunctional linker either through site-specific conjugation of the PEG to the N- or C-terminus of said antibodies or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography. PEG-derivatizated antibodies or antigen-binding fragments thereof can be tested for binding activity to RSV antigens as well as for in vivo efficacy using methods known to those skilled in the art, for example, by immunoassays described herein.

The antibodies of the invention can be single-chain antibodies. The design and construction of a single-chain antibody is described in Marasco et al, 1993, Proc Natl Acad Sci 90:7889-7893, which is incorporated herein by reference in its entirety.

In certain embodiments, the antibodies of the invention bind to an intracellular epitope, i.e., are intrabodies. An intrabody comprises at least a portion of an antibody that is capable of immunospecifically binding an antigen and preferably does not contain sequences coding for its secretion. Such antibodies will bind its antigen intracellularly. In one embodiment, the intrabody comprises a single-chain Fv ("sFv").

In a further embodiment, the intrabody preferably does not encode an operable secretory sequence and thus remains within the cell (see generally Marasco, W A, 1998, "Intrabodies: Basic Research and Clinical Gene Therapy Applications" Springer: New York).

sFv are antibody fragments comprising the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds. Springer-Verlag, New York, pp. 269-315 (1994).

5.4.1 Antibody Conjugates

The present invention also encompasses antibodies that are conjugated or fused to one or more moieties, including but not limited to, peptides, polypeptides, proteins, fusion proteins, nucleic acid molecules, small molecules, mimetic agents, synthetic drugs, inorganic molecules, and organic molecules.

The present invention encompasses antibodies that are recombinantly fused or chemically conjugated (including both covalent and non-covalent conjugations) to a heterologous protein or polypeptide (or fragment thereof, preferably to a polypepetide of at least 10, at least 20, at least 30, at least 40, at least 50, at least 60, at least 70, at least 80, at least 90 or at least 100 amino acids) to generate fusion proteins. The fusion does not necessarily need to be direct, but may occur through linker sequences. For example, antibodies may be used to target heterologous polypeptides to particular cell types, either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452, which are incorporated by reference in their entireties.

The present invention further includes compositions comprising heterologous proteins, peptides or polypeptides fused or conjugated to antibody fragments. For example, the heterologous polypeptides may be fused or conjugated to a Fab fragment, Fd fragment, Fv fragment, F(ab)$_2$ fragment, a Fc domain, a VH domain, a VL domain, a VH CDR, a VL CDR, or fragment thereof. Methods for fusing or conjugating polypeptides to antibody portions are well-known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341, (said references incorporated by reference in their entireties). See also PCT Publication No. WO 97/34631, U.S. patent application Ser. No. 10/020,354, entitled "Molecules with Extended Half-Lives, Compositions and Uses Thereof", filed Dec. 12, 2001, by Johnson et al., and U.S. patent application Ser. No. 11/263,230, filed Oct. 31, 2005, entitled "Methods of Preventing and Treating RSV Infections and Related Conditions," by Losonsky, the contents of which are incorporated by reference in their entireties.

In certain embodiments, the present invention provides a fusion protein that comprises an Fc domain of an antibody or a fragment thereof, wherein the Fc domain or the Fc domain fragment comprises at least one thioether cross-link. Such a fusion protein can be any fusion protein comprising an Fc domain or an Fc domain fragment known in the art, such as human tumor necrosis factor receptor Fc fusion protein, as described in Moreland et al., 2000, *New Eng. J. Med.* 343: 15869-93; or B7.1 Fc fusion protein, as described in Liu et al., 2005, *Cancer Research* 11(23):8492-8502, the contents of which are incorporated by reference in their entireties.

In some embodiments, the Fc domain may further comprise one or more amino acid substitutions (Fc variants). In some embodiments, Fc variants exhibit altered binding affinity for at least one or more Fc ligands (e.g., FcγRs, c1q). Exemplary Fc variants and methods of making such are described for example, in U.S. Patent Publication Nos. 2006/0039904 and 2006/0040325, both published on Feb. 23, 2006, the contents of which are incorporated by reference in their entireties.

In certain embodiments, the present invention provides a fusion protein that comprises an $C_H1$, $C_H2$, $C_H3$ and/or $C_L$ domain of an antibody, wherein the $C_H1$, $C_H2$, $C_H3$ or $C_L$ domain comprises at least one thioether cross-link.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment may be recombined with one or more components, motifs, sections, parts, domains, fragments, etc. of one or more heterologous molecules.

Moreover, the antibodies can be fused to marker sequences, such as a peptide to facilitate purification. In embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag.

In other embodiments, antibodies of the present invention, analogs or derivatives thereof can be conjugated to a diagnostic or detectable agent. Such antibodies can be useful for monitoring or prognosing the development or progression of a disorder as part of a clinical testing procedure, such as determining the efficacy of a particular therapy. Such diagnosis and detection can be accomplished by coupling the antibody to detectable substances including, but not limited to various enzymes, such as but not limited to horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I,), carbon ($^{14}$C), sulfur ($^{35}$S), tritium ($^{3}$H), indium ($^{115}$In, $^{113}$In, $^{112}$In, $^{111}$In,), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, noradioactive paramagnetic metal ions, and molecules that are radiolabelled or conjugated to specific radioisotopes.

The present invention further encompasses antibodies that are conjugated to a therapeutic moiety. An antibody or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), Auristatin molecules (e.g., auristatin PHE, bryostatin 1, and solastatin 10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40

(2001), Wall et al., Biochem. Biophys. Res. Commun. 266: 76-80 (1999), Mohammad et al., Int. J. Oncol. 15:367-72 (1999), all of which are incorporated herein by reference), hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantaijian et al., Clin Cancer Res. 8(7):2167-76 (2002)), cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, procaine, tetracaine, lidocaine, propranolol, and puromycin and analogs or homologs thereof) and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459), farnesyl transferase inhibitors (e.g., R115777, BMS-214662, and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305), topoisomerase inhibitors (e.g., camptothecin; irinotecan; SN-38; topotecan; 9-aminocamptothecin; GG-211 (GI 147211); DX-895 If; IST-622; rubitecan; pyrazoloacridine; XR-5000; saintopin; UCE6; UCE1022; TAN-1518A; TAN-1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin) and pharmaceutically acceptable salts, solvates, clathrates, and prodrugs thereof. See, e.g., Rothenberg, M. L., Annals of Oncology 8:837-855(1997); and Moreau, P., et al., J. Med. Chem. 41:1631-1640(1998)), antisense oligonucleotides (e.g., those disclosed in the U.S. Pat. Nos. 6,277,832, 5,998,596, 5,885,834, 5,734,033, and 5,618,709), immunomodulators (e.g., antibodies and cytokines), antibodies, and adenosine deaminase inhibitors (e.g., Fludarabine phosphate and 2-Chlorodeoxyadenosine).

Further, an antibody or fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, cholera toxin, or diphtheria toxin; a protein such as tumor necrosis factor, alpha.-interferon, .beta.-interferon, nerve growth factor, platelet derived growth factor, tissue plasminogen activator, an apoptotic agent, e.g., TNFα, TNFβ, AIM I (see, International publication No. WO 97/33899), AIM II (see, International Publication No. WO 97/34911), Fas Ligand (Takahashi et al., 1994, J. Immunol., 6:1567-1574), and VEGI (see, International publication No. WO 99/23105), a thrombotic agent or an anti-angiogenic agent, e.g., angiostatin, endostatin or a component of the coagulation pathway (e.g., tissue factor); or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid. fibrinopeptides A and B from the α and β chains of fibrinogen, fibrin monomer).

Moreover, an antibody can be conjugated to therapeutic moieties such as a radioactive metal ion, such as alph-emiters such as $^{213}$Bi or macrocyclic chelators useful for conjugating radiometal ions, including but not limited to, $^{131}$In, $^{131}$LU, $^{131}$Y, $^{131}$Ho, $^{131}$Sm, to polypeptides. In certain embodiments, the macrocyclic chelator is 1,4,7,10-tetraazacyclododecane-N,N',N'',N'''-tetraa-cetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Alternatively, an antibody can be conjugated to a second antibody to form an antibody heteroconjugate as described by Segal in U.S. Pat. No. 4,676,980, which is incorporated herein by reference in its entirety.

The therapeutic moiety or drug conjugated to an antibody or fragment thereof should be chosen to achieve the desired prophylactic or therapeutic effect(s) for a particular disorder in a subject. A clinician or other medical personnel should consider the following when deciding on which therapeutic moiety or drug to conjugate to an antibody or fragment thereof: the nature of the disease, the severity of the disease, and the condition of the subject.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

5.4.2 Isolated Antibodies Comprising at Least One Thioether Cross-Link that Specifically Bind to a Particular Antigen of and Compositions Comprising the Same In further embodiments, the present invention provides isolated antibodies or compositions comprising antibodies, wherein said antibodies comprises at least one thioether cross-link, and wherein said antibodies specifically bind to one or more particular antigens.

In certain embodiments, the antibody of the present invention specifically binds to an antigen of respiratory syncytial virus (RSV). In some embodiments, the antibody comprises the amino acid sequence of the variable heavy ($V_H$) and variable light (VL) chains of palivizumab or motavizumab. In other embodiments, the antibody comprises the amino acid sequence of the complementarity determining regions (CDRs) of the $V_H$ and $V_L$ chains of palivizumab or motavizumab.

In certain embodiments, the antibody of the present invention specifically binds to an antigen of human metapneumovirus (hMPV). In some embodiments, the antibody is a humanized antibody that specifically binds to an antigen of hMPV.

In certain embodiments, the antibody of the present invention specifically binds to integrin $\alpha_v\beta_3$. In some embodiments, the antibody comprises the amino acid sequence of the $V_H$ and $V_L$ chains of MEDI-522 (Vitaxin®). In other embodiments, the antibody comprises the amino acid sequence of the CDRs of the $V_H$ and $V_L$ chains of MEDI-522 (Vitaxin®).

In certain embodiments, the antibody of the present invention specifically binds to CD2. In some embodiments, the antibody comprises the amino acid sequence of the $V_H$ and $V_L$ chains of siplizumab. In other embodiments, the antibody comprises the amino acid sequence of the complementarity determining regions (CDRs) of $V_H$ and $V_L$ chains of siplizumab.

In certain embodiments, the antibody of the present invention specifically binds to CD19. In some embodiments, the antibody comprises the amino acid sequence of the $V_H$ and $V_L$ chains of MT103. In other embodiments, the antibody comprises the amino acid sequence of the CDRs of the $V_H$ and $V_L$ chains of MT103.

In certain embodiments, the antibody of the present invention specifically binds to an Eph receptor. In certain embodiments, the antibody of the present invention specifically binds to EphA2. In some embodiments, the antibody comprises the amino acid sequence of the $V_H$ and $V_L$ chains of EA2 or EA5. In other embodiments, the antibody comprises the amino acid sequence of the CDRs of the $V_H$ and $V_L$ chains of EA2 or EA5. In certain embodiments, the antibody of the present invention specifically binds to EphA4. In some embodiments, the antibody of the present invention specifically binds to EphB4.

In certain embodiments, the antibody of the present invention specifically binds to IL-9. In some embodiments, the antibody comprises the amino acid sequence of the $V_H$ and $V_L$ chains of MEDI-528. In other embodiments, the antibody comprises the amino acid sequence of the CDRs of the $V_H$ and $V_L$ chains of MEDI-528.

In certain embodiments, the antibodies of the present invention are those antibodies other than an antibody that specifically binds to an antigen of RSV, an antigen of human metapneumovirus (hMPV), integrin $\alpha_v\beta_3$, CD2, CD19, Eph receptor (e.g., EphA2, EphA4 or EphB4), or IL-9. In certain embodiments, the antibody of the present invention is not an antibody that specifically binds to an antigen of respiratory syncytial virus (RSV). In other embodiments, the antibody of the present invention is not an antibody that specifically binds to an antigen of human metapneumovirus (hMPV). In certain embodiments, the antibody of the present invention is not an antibody that specifically binds to integrin $\alpha_v\beta_3$. In certain embodiments, the antibody of the present invention is not an antibody that specifically binds to CD2. In certain embodiments, the antibody of the present invention is not an antibody that specifically binds to CD19. In further embodiments, the antibody of the present invention is not an antibody that specifically binds to EphA2. In certain embodiments, the antibody of the present invention is not an antibody that specifically binds to EphA4. In certain embodiments, the antibody of the present invention is not an antibody that specifically binds to IL-9.

In some embodiments, the antibody is not palivizumab. In other embodiments, the antibody is not motavizumab. In some embodiments, the antibody is not MEDI-522 (Vitaxin®). In some embodiments, the antibody is not siplizumab. In some embodiments, the antibody is not MT-103™. In some embodiments, the antibody is not human or humanized EA2 or EA5. In some embodiments, the antibody is not MEDI-528.

The antibodies of the present invention may be high potency antibodies. The term "high potency" as used herein refers to antibodies that exhibit high potency as determined in various assays for biological activity (e.g., neutralization of an antigen). High potency antibodies can be produced by genetically engineering appropriate antibody gene sequences and expressing the antibody sequences in a suitable host. See U.S. Application Publication No. 2002/0098189, published Jul. 25, 2002, the contents of which are incorporate by reference in their entirety. The antibodies produced can be screened to identify antibodies with, e.g., high $k_{on}$ values in a BIAcore assay.

In a specific embodiment, the antibodies of the present invention have an association rate constant or $k_{on}$ rate (antibody (Ab)+antigen (Ag)$^{k_{on}}$→Ab-Ag) of at least $10^5$ M$^{-1}$s$^{-1}$, at least $5\times10^5$ M$^{-1}$s$^{-1}$, at least $10^6$ M$^{-1}$s$^{-1}$, at least $5\times10^6$ M$^{-1}$s$^{-1}$, at least $10^7$ M$^{-1}$S$^{-1}$, at least $5\times10^7$ M$^{-1}$s$^{-1}$, or at least $10^8$ M$^{-1}$s$^{-1}$. In a preferred embodiment, the antibodies of the present invention have a $k_{on}$ of at least $2\times10^5$ M$^{-1}$s$^{-1}$, at least $5\times10^5$ M$^{-1}$s$^{-1}$, at least $10^6$ M$^{-1}$s$^{-1}$, at least $5\times10^6$ M$^{-1}$s$^{-1}$, at least $10^7$ M$^{-1}$s$^{-1}$, at least $5\times10^7$ M$^{-1}$ s$^{-1}$, or at least $10^8$ M$^{-1}$ s$^{-1}$. In some embodiments, the antibodies of the present invention have a $k_{on}$ rate between $10^5$ M$^{-1}$s$^{-1}$ and $10^8$ M$^{-1}$s$^{-1}$, between $10^5$ M$^{-1}$s$^{-1}$ and $10^8$ M$^{-1}$s$^{-1}$, between $10^5$ M$^{-1}$s$^{-1}$ and $10^7$ M$^{-1}$s$^{-1}$, between $10^5$ M$^{-1}$s$^{-1}$ and $10^6$ M$^{-1}$s$^{-1}$, or between $10^6$ M$^{-1}$s$^{-1}$ and $10^7$ M$^{-1}$S$^{-1}$.

In another embodiment, the antibodies of the present invention have a $k_{off}$ rate (antibody (Ab)+antigen) of less than $5\times10^{-1}$ s$^{-1}$, less than $10^{-1}$ s$^{-1}$, less than $5\times10^{-2}$ s$^{-1}$, less than $10^{-2}$ s$^{-1}$, less than $5\times10^{-3}$ s$^{-1}$, less than $10^{-3}$ s$^{-1}$, less than $5\times10^{-4}$s$^{-1}$, less than $10^{-4}$ s$^{-1}$, less than $5\times10^{-5}$ s$^{-1}$, less than $10^{-5}$ s$^{-1}$, less than $5\times10^{-6}$ s$^{-1}$, less than $10^{-6}$ S$^{-1}$, less than $5\times10^{-7}$ s$^{-1}$, less than $10^{-7}$ s$^{-1}$, less than $5\times10^{-8}$ S$^{-1}$, less than $10^{-8}$ s$^{-1}$, less than $5\times10^{-9}$ s$^{-1}$, less than $10^{-9}$ s$^{-1}$, or less than $10^{-10}$ s$^{-1}$. In a preferred embodiment, the antibodies of the present invention have a $k_{off}$ of less than $5\times10^{-4}$ s$^{-1}$, less than $5\times10^{-5}$ s$^{-1}$, less than $10^{-5}$ s$^{-1}$, less than $5\times10^{-6}$ s$^{-1}$, less than $10^{-6}$ s$^{-1}$, less than $5\times10^{-7}$ s$^{-1}$, less than $10^{-7}$ s$^{-1}$, less than $5\times10^{-8}$ s$^{-1}$, less than $10^{-8}$ s$^{-1}$, less than $5\times10^{-9}$ s$^{-1}$, less than $10^{-9}$ s$^{-1}$, or less than $10^{-10}$ s$^{-1}$. In some embodiments, the antibodies of the present invention have a $k_{off}$ between $5\times10^{-4}$ s$^{-1}$ and $10^{-10}$ s$^{-1}$, between $5\times10^{-4}$ s$^{-1}$ and $10^{-9}$ s$^{-1}$, between $5\times10^4$ s$^{-1}$ and $10^{-8}$ s$^{-1}$, between $5\times10^{-7}$ s$^{-1}$ and $10^{-7}$ s$^{-1}$, between $10^{-5}$ s$^{-1}$ and $10^{-10}$ s$^{-1}$, or between $10^{-6}$ s$^{-1}$ and $10^{-9}$s$^{-1}$.

In certain embodiments, the antibodies of the present invention have a high binding affinity for one or more antigens. See U.S. Pat. No. 6,656,467, the contents of which are incorporated by reference in its entirety. In certain embodiments, the antibodies of the present invention have an affinity constant or $K_a$ ($k_{on}/k_{off}$) of at least $10^2$ M$^{-1}$, at least $5\times10^2$ M$^{-1}$, at least $10^3$ M$^{-1}$, at least $5\times10^3$ M$^{-1}$, at least $10^4$ M$^{-1}$, at least $5 \times 10^4$ M$^{-1}$, at least $10^5$ M$^{-1}$, at least $5 \times 10^5$ M$^{-1}$, at least $10^6$ M$^{-1}$, at least $5 \times 10^6$ M$^{-1}$, at least $10^7$ M$^{-1}$, at least $5 \times 10^7$ M$^{-1}$, at least $10^8$ M$^{-1}$, at least $5 \times 10^8$ M$^{-1}$, at least $10^9$ M$^{-1}$, at least $5 \times 10^9$ M$^{-1}$, at least $10^{10}$ M$^{-1}$, at least $5 \times 10^1$ M$^{-1}$, at least $10^{11}$ M$^{-1}$, at least $5 \times 10^{11}$ M$^{-1}$, at least $10^{12}$ M$^{-1}$, at least $5 \times 10^{12}$ M$^{-1}$, at least $10^{13}$ M$^{-1}$, at least $5 \times 10^{13}$ M$^{-1}$, at least $10^{14}$ M$^{-1}$, at least $5 \times 10^{14}$ M$^{-1}$, at least $10^{15}$ M$^{-1}$, or at least $5 \times 10^{15}$ M$^{-1}$. The present invention also provides compositions comprising one or more antibodies which immunospecifically bind to an antigen with an affinity constant of at least $2 \times 10^8$ M$^{-1}$, at least $2.5 \times 10^8$ M$^{-1}$, at least $5 \times 10^8$ M$^{-1}$, at least $10^9$ M$^{-1}$, at least $5 \times 10^9$ M$^{-1}$, at least $10^{10}$ M$^{-1}$, at least $5 \times 10^{11}$ M$^{-1}$, at least $10^{11}$ M$^{-1}$, at least $5 \times 10^{11}$ M$^{-1}$, at least $10^{12}$ M$^{-1}$, at least $5 \times 10^{12}$ M$^{-1}$, at least $10^{13}$ M$^{-1}$, at least $5 \times 10^{13}$ M$^{-1}$, at least $10^{14}$ M$^{-1}$, at least $5 \times 10^{14}$ M$^{-1}$, at least $1105$ M$^{-1}$, or at least $5 \times 10^{15}$ M$^{-1}$. In certain embodiments, the antibodies of the present invention has $K_a$ ($k_{on}/k_{off}$) between $10^2$ M$^{-1}$ and $5 \times 10^{15}$ M$^{-1}$, between $10^4$ M$^{-1}$ and $5 \times 10^{15}$ M$^{-1}$, between $10^6$ M$^{-1}$ and $5 \times 10^{15}$ M$^{-1}$, between $10^8$ M$^{-1}$ and $5 \times 10^{15}$ M$^{-1}$, between $10^{10}$ M$^{-1}$ and $5 \times 10^{15}$ M$^{-1}$, between $10^{12}$ M$^{-1}$ and $5 \times 10^{15}$ M$^{-1}$, between $10^{14}$ M$^{-1}$ and $5 \times 10^{15}$ M$^{-1}$, between $10^4$ M$^{-1}$ and $10^{14}$ M$^{-1}$, between $10^6$ M$^{-1}$ and $10^{12}$ M$^{-1}$, or between $10^8$ M$^{-1}$ and $10^{10}$ M$^{-1}$.

In yet another embodiment, the antibodies of the present invention have a dissociation constant or $K_d$ ($k_{off}/k_{on}$) of less than $5 \times 10^{-2}$ M, less than $10^{-2}$ M, less than $5 \times 10^{-3}$ M, less than $10^{-3}$ M, $5 \times$ less than $10^4$ M, less than $10^4$ M, $5 \times$ less than $10^{-5}$ M, less than $10^{-5}$ M, less than $5 \times 10^{-6}$ M, less than $10^{-6}$ M, less than $5 \times 10^{-7}$ M, less than $10^{-7}$ M, less than $5 \times 10^{-8}$ M, less than $10^{-8}$ M, less than $5 \times 10^{-9}$ M, less than $10^{-9}$ M, less than $5 \times 10^{-10}$ M, less than $10^{-10}$ M, less than $5 \times 10^{-11}$ M, less than $10^{-11}$ M, less than $5 \times 10^{-12}$ M, less than $10^{-12}$ M, less than $5 \times 10^{-13}$ M, less than $10^{-13}$ M, less than $5 \times 10^{-14}$ M, less than $10^{-14}$ M, less than $5 \times 10^{-15}$ M, or less than $10^{-15}$ M. In some embodiments, the antibodies of the present invention have a $K_d$ between $10^{-2}$ M and $5 \times 10^{-15}$ M, between $10^{-5}$ M and $5 \times 10^{-15}$ M, between $10^{-8}$ M and $5 \times 10^{-15}$ M, between $10^{-11}$ M and $5 \times 10^{-15}$ M, between $10^{-4}$ M and $10^{-14}$ M, between $10^{-6}$ M and $10^{-12}$ M, or between $10^{-8}$ M and $10^{-10}$ M.

In certain embodiments, the antibodies of the present invention have a median effective concentration (EC$_{50}$) of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay. The median effective concentration is the concentration of antibody or antibody fragments that neutralizes 50% of an antigen in an in vitro microneutralization assay. In a preferred embodiment, the antibodies of the present invention have an EC$_{50}$ of less than 0.01 nM, less than 0.025 nM, less than 0.05 nM, less than 0.1 nM, less than 0.25 nM, less than 0.5 nM, less than 0.75 nM, less than 1 nM, less than 1.25 nM, less than 1.5 nM, less than 1.75 nM, or less than 2 nM, in an in vitro microneutralization assay. In certain embodiments, the antibodies of the present invention have an EC$_{50}$ between 0.01 nM and 2 nM, between 0.025 nM and 1.75 nM, between 0.05 nM and 1.5 nM, between 0.1 nM and 1.25 nM, or between 0.25 nM and 1 nM.

5.4.2.1. Antibodies Comprising at Least One Thioether Cross-Link that Specifically Bind to an Antigen of Respiratory Syncytial Virus (RSV) and Compositions Comprising the Same The present invention provides an isolated antibody that comprises at least one thioether cross-link and specifically binds to an antigen of respiratory syncytial virus (RSV) and a composition comprising this antibody. The thioether cross-link is described in detail in Section 5.2. The antibodies of the present invention can comprise one or multiple thioether cross-links. The thioether cross-link can link any two residues of the antibody. In certain embodiments, the residues linked by the thioether cross-link are natural residues. In preferred embodiments, two of the residues are cysteine residues. The thioether cross-link can be at any location of the antibodies where feasible according to the knowledge of those of skill in the art. In preferred embodiments, the thioether cross-link links a heavy chain and a light chain of the antibody. In particular preferred embodiments, the thioether cross-link links a cysteine of a heavy chain and a cysteine of a light chain of the antibody.

This antibody of the invention specifically binds to an antigen of respiratory syncytial virus (RSV). The term "anti-RSV-antigen antibody" refers to an antibody that binds immunospecifically to a RSV antigen. A RSV antigen refers to a RSV polypeptide or fragment thereof such as of RSV nucleoprotein, RSV phosphoprotein, RSV matrix protein, RSV small hydrophobic protein, RSV RNA-dependent RSV polymerase, RSV F protein, and RSV G protein. A RSV antigen also refers to a polypeptide that has a similar amino acid sequence compared to a RSV polypeptide or fragment thereof such as of RSV nucleoprotein, RSV phosphoprotein, RSV matrix protein, RSV small hydrophobic protein, RSV RNA-dependent RSV polymerase, RSV F protein, and RSV G protein. In certain embodiments, the antibody specifically binds to an epitope in the A antigenic site of the fusion (F) protein of RSV.

The anti-RSV-antigen antibody of the invention can be a monoclonal antibody, human antibody, humanized antibody or chimeric antibody. In some preferred embodiments, the present invention provides a palivizumab that comprises at least one thioether cross-link. In a specific preferred embodiment, the palivizumab is SYNAGIS®.

Palivizumab is a humanized monoclonal antibody produced by recombinant DNA technology that specifically binds to an epitope in the A antigenic site of the fusion (F) protein of RSV. It is a composite of human (95%) and murine (5%) antibody sequences. Palivizumab has high specific activity against RSV in vitro and is known to neutralize a broad range of RSV isolates. Since it is not derived from human plasma, prophylactic treatment with palivizumab does not carry potential risk of transmission of blood borne pathogens. The amino acid sequence of palivizumab is disclosed, e.g., in Johnson et al., 1997, J. Infectious Disease 176:1215-1224, and International Application Publication No.: WO 02/43660, entitled "Methods of Administering/Dosing Anti-RSV Antibodies for Prophylaxis and Treatment", by Young et al., which are incorporated herein by reference in their entireties. The properties and uses of palivizumab are also disclosed in, e.g., other applications, see, e.g., U.S. patent application Ser. No. 09/724,396 filed Nov. 28, 2000; U.S. patent application Ser. No. 09/996,265 filed Nov. 28, 2001 and U.S. patent application Ser. No. 10/403,180 filed Mar. 31, 2003, all of which are incorporated herein by reference.

In some embodiments, the antibody comprises the amino acid sequence of the $V_H$ and $V_L$ chains of palivizumab. In other embodiments, the antibody comprises the amino acid sequence of the CDRs of the $V_H$ and $V_L$ chains of palivizumab. The amino acid sequences of the $V_H$ and $V_L$ chains of palivizumab and the CDRs of the $V_H$ and $V_L$ chains of palivizumab are listed in Table 1 and provided in U.S. patent application Ser. No. 11/263,230, filed Oct. 31, 2005, entitled "Methods of Preventing and Treating RSV Infections and Related Conditions," by Losonsky, the contents of which are hereby incorporated by reference in their entirety.

In further embodiments, the invention provides a motavizumab that comprises at least one thioether cross-link. The amino acid sequence, properties and uses of motavizumab are disclosed in U.S. Pat. No. 6,818,216 and Young et al. In some embodiments, the amino acid sequence of motavizumab is encoded by SEQ ID NOs. 254 and 255 for the heavy and light chain respectively, disclosed in U.S. Pat. No. 6,818,216.

In certain specific embodiments, the anti-RSV-antigen antibody is AFFF; P12f2 P12f4; P11d4; A1e9; A12a6; A13c4; A17d4; A4B4; 1X-493L1; FR H3-3F4; M3H9; Y10H6; DG; AFFF(1); 6H8; L1-7E5; L2-15B10; A13a11; A1h5; A4B4(1); A4B4-F52S; or A4B4L1FR-S28R. These antibodies are disclosed in International Application Publication No.: WO 02/43660, entitled "Methods of Administering/Dosing Anti-RSV Antibodies for Prophylaxis and Treatment", by Young et al., and U.S. patent application Ser. No. 396 filed Nov. 28, 2000; U.S. patent application Ser. No. 09/724,531 filed Nov. 28, 2000; U.S. patent application Ser. No. 09/996,265 filed Nov. 28, 2001; U.S. patent application Ser. No. 10/403,180 filed Mar. 31, 2003; U.S. patent application Ser. No. 09/796,848 filed Mar. 1, 2001 and published on Jul. 25, 2002, as U.S. Pat. Pub. No. 2002/0098189; U.S. patent application Ser. No. 10/135,636, filed Apr. 29, 2002 and published May 29, 2003, as U.S. Pat. Pub. No. 2002/0097974; U.S. patent application Ser. No. 10/461,904 filed Jun. 13, 2003; U.S. patent application Ser. No. 10/461,863 filed Jun. 13, 2003 and published on Jan. 29, 2004, as U.S. Pat. Pub. No. 2004/0018200, and U.S. patent application Ser. No. 11/263,230, filed Oct. 31, 2005, entitled "Methods of Preventing and Treating RSV Infections and Related Conditions," by Losonsky, the contents of which are hereby incorporated by reference in their entirety.

TABLE 1

VH, VL AND CDR SEQUENCES

| Antibody Name | VH Chain | VH Domain | VH CDR1 | VH CDR2 | VH CDR3 | VL Chain | VL Domain | VL CDR1 | VL CDR2 | VL CDR3 |
|---|---|---|---|---|---|---|---|---|---|---|
| palivizumab | SEQ ID NO:1 | SEQ ID NO:2 | TSGMSVG (SEQ ID NO:3) | DIWWDDKK DYNPSLKS (SEQ ID NO:4) | SMITNWYF DV (SEQ ID NO:5) | SEQ ID NO:6 | SEQ ID NO:7 | KCQLSVGY MH (SEQ ID NO:8) | DTSKLAS (SEQ ID NO:9) | FQGSGYPF T (SEQ ID NO:10) |
| motovizumab | SEQ ID NO:11 | SEQ ID NO:12 | TAGMSVG (SEQ ID NO:13) | DIWWDDKK HYNPSLKD (SEQ ID NO:14) | DMIFNFYF DV (SEQ ID NO:15) | SEQ ID NO:16 | SEQ ID NO:17 | SASSRVGY MH (SEQ ID NO:18) | DTSKLAS (SEQ ID NO:9) | FQGSGYPF T (SEQ ID NO:10) |
| EA2 | SEQ ID NO:19 | | SEQ ID NO:20 | SEQ ID NO:21 | SEQ ID NO:22 | SEQ ID NO:23 | | SEQ ID NO:24 | SEQ ID NO:25 | SEQ ID NO:26 |
| siplizumab | | | SEQ ID NO:27 | SEQ ID NO:28 | SEQ ID NO:29 | | | SEQ ID NO:30 | SEQ ID NO:31 | SEQ ID NO:32 |
| 7F3com-2H2 | | | SEQ ID NO:33 | SEQ ID NO:34 | SEQ ID NO:35 | | | SEQ ID NO:36 | SEQ ID NO:37 | SEQ ID NO:38 |
| MT-103 ™ | CD19 portion (SEQ ID NO:40) CD3 portion (SEQ ID NO:41) | | | | | CD19 portion SEQ ID NO:39 CD3 portion (SEQ ID NO:42) | | | | |

11/263,230, filed Oct. 31, 2005, entitled "Methods of Preventing and Treating RSV Infections and Related Conditions," by Losonsky, which is incorporated herein by reference in its entirety.

In some embodiments, the antibody comprises the amino acid sequence of the $V_H$ and $V_L$ chains of motobizumab. In other embodiments, the antibody comprises the amino acid sequence of the CDRs of the $V_H$ and $V_L$ chains of motobizumab. The amino acid sequences of the $V_H$ and $V_L$ chains of palivizumab and the CDRs of the $V_H$ and $V_L$ chains of motobizumab are listed in Table 1 and provided in U.S. patent application Ser. No. 11/263,230, filed Oct. 31, 2005, entitled "Methods of Preventing and Treating RSV Infections and Related Conditions," by Losonsky, the contents of which are hereby incorporated by reference in their entirety.

The anti-RSV-antigen antibodies of this section can be made, formulated, administered, used therapeutically or used prophylactically as described in U.S. Pat. No. 5,824,307; U.S. Pat. No. 6,818,216; U.S. patent application Ser. No. 09/724,

5.4.2.2. Antibodies Comprising at least One Thioether Cross-Link that Specifically Bind to an Antigen of Human Metapneumovirus (hMPV) and Compositions Comprising the Same The present invention provides an isolated antibody that comprises at least one thioether cross-link and specifically binds to an antigen of human metapneumovirus (hMPV) and a composition comprising this antibody. The thioether cross-link is described in detail in Section 5.2. The antibodies of the present invention can comprise one or multiple thioether cross-links. he thioether cross-link can link any two residues of the antibody. In certain embodiments, the residues linked by the thioether cross-link are natural residues. In preferred embodiments, two of the residues are cysteine residues. The thioether cross-link can be at any location of the antibodies where feasible according to the knowledge of those of skill in the art. In preferred embodiments, the thioether cross-link links a heavy chain and a light chain of the antibody. In particular preferred embodiments, the thioether cross-link links a cysteine of a heavy chain and a cysteine of a light chain of the antibody.

This antibody of the invention specifically binds to an antigen of human metapneumovirus (hMPV). The term "anti-hMPV-antigen antibody" refers to an antibody or antibody fragment thereof that binds immunospecifically to a hMPV antigen. A hMPV antigen refers to a hMPV polypeptide or fragment thereof such as of hMPV nucleoprotein, hMPV phosphoprotein, hMPV matrix protein, hMPV small hydrophobic protein, hMPV RNA-dependent hMPV polymerase, hMPV F protein, and hMPV G protein. A hMPV antigen also refers to a polypeptide that has a similar amino acid sequence compared to a hMPV polypeptide or fragment thereof such as of hMPV nucleoprotein, hMPV phosphoprotein, hMPV matrix protein, hMPV small hydrophobic protein, hMPV RNA-dependent hMPV polymerase, hMPV F protein, and hMPV G protein.

The anti-hMPV-antigen antibodies of this invention can be monoclonal antibodies, human antibodies, humanized antibodies or chimeric antibodies. In some preferred embodiments, the anti-hMPV antibody of the invention is the antibody disclosed in U.S. patent application Ser. No. 10/628,088, filed Jul. 25, 2003 and published May 20, 2004, as U.S. Pat. Pub. No. US 2004/0096451 A1.

The anti-hMPV-antigen antibodies of this section can be made, formulated, administered, used therapeutically or used prophylactically as described in U.S. patent application Ser. No. 10/628,088, filed Jul. 25, 2003 and published May 20, 2004, as U.S. Pat. Pub. No. US 2004/0096451 A1, the contents of which are hereby incorporated by reference in their entirety.

5.4.2.3. Antibodies Comprising at Least One Thioether Cross-Link that Specifically Bind to Integrin $\alpha_v\beta_3$ and Compositions Comprising the Same The present invention provides an isolated antibody that comprises at least one thioether cross-link and specifically binds to integrin $\alpha_v\beta_3$ and a composition comprising this antibody. The thioether cross-link is described in detail in Section 5.2. The antibodies of the present invention can comprise one or multiple thioether cross-links. The thioether cross-link can link any two residues of the antibody. In certain embodiments, the residues linked by the thioether cross-link are natural residues. In preferred embodiments, two of the residues are cysteine residues. The thioether cross-link can be at any location of the antibodies where feasible according to the knowledge of those of skill in the art. In preferred embodiments, the thioether cross-link links a heavy chain and a light chain of the antibody. In particular preferred embodiments, the thioether cross-link links a cysteine of a heavy chain and a cysteine of a light chain of the antibody.

This antibody of the invention specifically binds to integrin $\alpha_v\beta_3$. The antibodies can be monoclonal antibodies, human antibodies, humanized antibodies or chimeric antibodies. In some preferred embodiments, the anti-integrin $\alpha_v\beta_3$ antibody of the invention is MEDI-522 (Vitaxin®). Vitaxin® and compositions or formulations comprising Vitaxin® are disclosed, e.g., in International Publication Nos. WO 98/33919, WO 00/78815, and WO 02/070007; U.S. application Ser. No. 09/339,222; U.S. patent application Ser. No. 10/091,236, filed Mar. 4, 2002 and published Nov. 12, 2002, as U.S. Pat. Pub. No. US 2002/0168360, each of which is incorporated herein by reference in its entirety.

In further embodiments, the antibody that immunospecifically binds to integrin $\alpha_v\beta_3$ is not Vitaxin® or an antigen-binding fragment of Vitaxin®. Examples of known antibodies that immunospecifically bind to integrin $\alpha_v\beta_3$ include, but are not limited to, 11D2 (Searle), the murine monoclonal LM609 (Scripps, International Publication Nos. WO 89/05155 and U.S. Pat. No. 5,753,230, which is incorporated herein by reference in its entirety), International Publication Nos WO 98/33919 and WO 00/78815, each of which is incorporated herein by reference in its entirety), 17661-37E and 17661-37E 1-5 (USBiological), MON 2032 and 2033 (Cal-Tag), ab7166 (BV3) and ab 7167 (BV4) (Abcam), and WOW-1 (Kiosses et al., Nature Cell Biology, 3:316-320).

$\alpha_v\beta_3$ an integrin has been found on new blood vessels as well as surface of many solid tumors, activated macrophages, monocytes, and osteoclasts. As the such, the anti-integrin $\alpha_v\beta_3$ antibodies of this section can be used, for example, as an investigational antibody, or in the prevention or treatment of several destructive diseases.

The anti-integrin $\alpha_v\beta_3$ antibodies of this section can be made, formulated, administered, used therapeutically or used prophylactically as described in U.S. patent application Ser. No. 10/091,236, filed Mar. 4, 2002 and published Nov. 12, 2002, as U.S. Pat. Pub. No. US 2002/0168360; U.S. patent application Ser. No. 10/769,712, filed Jan. 30, 2004; U.S. patent application Ser. No. 10/769,720, filed Jan. 30, 2004 and published Sep. 9, 2004, as U.S. Pat. Pub. No. US 2004/0176272; U.S. patent application Ser. No. 10/379,145, filed Mar. 4, 2003; U.S. patent application Ser. No. 10/379,189, filed Mar. 4, 2003 and published as U.S. Pat. Pub. No. US 2004/0001835; PCT Application No. PCT/US04/02701, filed Jan. 30, 2004; International Application Publication No.: WO 00/78815 A1, entitled "Anti-$\alpha_v\beta_3$ recombinant human antibodies, nucleic acids encoding same and methods", by Huse et al.; and International Application Publication No.: WO 98/33919 A1, entitled "Anti-alpha-V-veta-3 recombinant humanized antibodies, nucleic acids encoding same and methods of use", by Huse et al.; International Publication No. WO 89/05155, the contents of which are hereby incorporated by reference in their entirety.

5.4.2.4. Antibodies Comprising at Least One Thioether Cross-Link that Specifically Bind to CD2 and Compositions Comprising the Same The present invention provides an isolated antibody that comprises at least one thioether cross-link and specifically binds to CD2 and a composition comprising this antibody. The thioether cross-link is described in detail in Section 5.2. The antibodies of the present invention can comprise one or multiple thioether cross-links. he thioether cross-link can link any two residues of the antibody. In certain embodiments, the residues linked by the thioether cross-link are natural residues. In preferred embodiments, two of the residues are cysteine residues. The thioether cross-link can be at any location of the antibodies where feasible according to the knowledge of those of skill in the art. In preferred embodiments, the thioether cross-link links a heavy chain and a light chain of the antibody. In particular preferred embodiments, the thioether cross-link links a cysteine of a heavy chain and a cysteine of a light chain of the antibody.

This antibody of the invention specifically binds to CD2. The antibodies can be monoclonal antibodies, human antibodies, humanized antibodies or chimeric antibodies. In some preferred embodiments, the anti-CD2 antibody of the invention is siplizumab (MEDI-507). Siplizumab can selectively binds to cells expressing the CD2 antigen (specifically T cells, natural killer cells and thymocytes) and can be used, for example, in the prophylaxis and treatment of T cell lymphoma or other related conditions. MEDI-507 is disclosed, e.g., in International Publication No. WO 99/03502, International Application Nos. PCT/US02/22273 and PCT/US02/06761, and U.S. application Ser. Nos. 09/462,140, 10/091, 268, and 10/091,313, each of which is incorporated herein by reference in its entirety. MEDI-507 is a humanized IgG1κ class monoclonal antibody that immunospecifically binds to human CD2 polypeptide. MEDI-507 was constructed using molecular techniques to insert the CDRs from the rat monoclonal antibody LO-CD2a/BTI-322 into a human IgG1 framework. LO-CD2a/BTI-322 has the amino acid sequence disclosed, e.g., in U.S. Pat. Nos. 5,730,979, 5,817,311, and 5,951,983; and U.S. application Ser. Nos. 09/056,072 and 09/462,140 (each of which is incorporated herein by reference in its entirety), or the amino acid sequence of the monoclonal antibody produced by the cell line deposited with the American Type Culture Collection (ATCC®), 10801 University Boulevard, Manassas, Va. 20110-2209 on Jul. 28, 1993 as Accession Number HB 11423.

In some embodiments, the antibody comprises the amino acid sequence of the $V_H$ and $V_L$ chains of siplizumab (MEDI-507). In other embodiments, the antibody comprises the amino acid sequence of the CDRs of the $V_H$ and $V_L$ chains of siplizumab (MEDI-507). The amino acid sequences of the CDRs of the $V_H$ and $V_L$ chains of siplizumab (MEDI-507) are listed in Table 1 are provided in U.S. Patent Publication No. 2003/0044406, published on Mar. 6, 2003, the contents of which are hereby incorporated by reference in its entirety.

The anti-CD2 antibodies of this section can be made, formulated, administered, used therapeutically or prophylactically, or in other context as described in U.S. patent application Ser. No. 10/091,268, filed Mar. 4, 2002, and published Apr. 15, 2003, as U.S. Pat. Pub. No. US 2003/0068320; U.S. patent application Ser. No. 10/091,313, filed Mar. 4, 2002, and published Mar. 6, 2003, as U.S. Pat. Pub. No. US 2003/0044406; and U.S. patent application Ser. No. 10/657,006, filed Sep. 5, 2003, and published Dec. 30, 2004, as U.S. Pat. Pub. No. US 2004/0265315, the contents of which are hereby incorporated by reference in their entirety.

5.4.2.5. Antibodies Comprising at least One Thioether Cross-Link that Specifically Bind to CD19 and Compositions Comprising the Same The present invention provides an isolated antibody that comprises at least one thioether cross-link and specifically binds to CD19 and a composition comprising this antibody. The thioether cross-link is described in detail in Section 5.2. The antibodies of the present invention can comprise one or multiple thioether cross-links. The thioether cross-link is described in detail in the section above. The thioether cross-link can link any two residues of the antibodies. In certain embodiments, the residues linked by the thioether cross-link are natural residues. In preferred embodiments, two of the residues are cysteine residues. The thioether cross-link can be at any location of the antibodies where feasible according to the knowledge of those of skill in the art. In preferred embodiments, the thioether cross-link links a heavy chain and a light chain of the antibodies. In particular preferred embodiments, the thioether cross-link links a cysteine of a heavy chain and a cysteine of a light chain of the antibodies.

This antibody of the invention specifically binds to CD19. The antibodies can be monoclonal antibodies, human antibodies, humanized antibodies or chimeric antibodies. In some preferred embodiments, the anti-CD19 antibody of the invention is MT-103™. MT-103™ is the most-advanced clinical representative of a novel class of antibody derivatives called Bi-Specific T Cell Engagers (BiTE™). The BiTE compound MT-103™ directs and activates the patient's own immune system against the cancer cells, stimulating T cells (a very potent type of white blood cell) to destroy B tumor cells (cancerous white blood cells). MT-103™ specifically targets a particular protein (the CD19 antigen), which is present on cancerous B cells but not on other types of blood cells or healthy tissues, therefore avoiding the side effects of traditional chemotherapy The anti-CD19 antibodies of this section can be made, formulated, administered, used therapeutically or prophylactically, or in other context as described in U.S. Pat. No. 6,723,538, and U.S. Pat. Pub. No. 2004/0162411, which are incorporated herein by reference in their entirety. The amino acid sequences of the $V_H$ and $V_L$ domains of MT-103™ are listed in Table 1 and provided in U.S. Patent Publication No. 2004/0162411.

5.4.2.6. Antibodies Comprising at Least One Thioether Cross-Link that Specifically Bind to an Eph Receptor and Compositions Comprising the Same The present invention provides an isolated antibody that comprises at least one thioether cross-link and specifically binds to an Eph receptor and a compositions comprising this antibody. The thioether cross-link is described in detail in Section 5.2. The antibodies of the present invention can comprise one or multiple thioether cross-links. he thioether cross-link can link any two residues of the antibody. In certain embodiments, the residues linked by the thioether cross-link are natural residues. In preferred embodiments, two of the residues are cysteine residues. The thioether cross-link can be at any location of the antibodies where feasible according to the knowledge of those of skill in the art. In preferred embodiments, the thioether cross-link links a heavy chain and a light chain of the antibody. In particular preferred embodiments, the thioether cross-link links a cysteine of a heavy chain and a cysteine of a light chain of the antibody.

As used herein, the term "Eph receptor" or "Eph receptor tyrosine kinase" refers to any Eph receptor that has or will be identified and recognized by the Eph Nomenclature Committee (Eph Nomenclature Committee, 1997, Cell 90:403-404). Eph receptors of the present invention include, but are not limited to EphA1, EphA2, EphA3, EphA4, EphA5, EphA6, EphA7, EphA8, EphB1, EphB2, EphB3, EphB4, EphB5 and EphB6. In a specific embodiment, an Eph receptor polypeptide is from any species. In a preferred embodiment, an Eph receptor polypeptide is human. The nucleotide and/or amino acid sequences of Eph receptor polypeptides can be found in the literature or public databases (e.g., GenBank), or the nucleotide and/or amino acid sequences can be determined using cloning and sequencing techniques known to one of skill in the art. The GenBank Accession Nos. for the nucleotide and amino acid sequences of the human Eph receptors are summarized in TABLE 2 below.

TABLE 2

| Eph Receptor | Nucleotide Sequence | Amino Acid Sequence |
|---|---|---|
| EphA1 | NM_005232.2 | NP_005223.2 |
| EphA2 | NM_004431.2 | NP_004422.2 |
| EphA3, variant 1 | NM_005233.3 | NP_005224.2 |
| EphA3, variant 2 | NM_182644.1 | NP_872585.1 |
| EphA4 | NM_004438.3 | NP_004429.1 |
| EphA5, variant 1 | NM_004439.3 | NP_004430.2 |
| EphA5, variant 2 | NM_182472.1 | NP_872272.1 |
| EphA6 (predicted) | XM_114973.4 | XP_114973.4 |
| EphA7 | NM_004440.2 | NP_004431.1 |
| EphA8 | NM_020526.2 | NP_065387.1 |
| EphB1 | NM_004441.2 | NP_004432.1 |
| EphB2, variant 1 | NM_017449.1 | NP_059145.1 |
| EphB2, variant 2 | NM_004442.4 | NP_004433.2 |
| EphB3 | NM_004443.3 | NP_004434.2 |
| EphB4 | NM_004444.3 | NP_004435.3 |
| EphB5 (chicken; human sequence not reported) | NM_001004387.1 | NP_001004387.1 |
| EphB6 | NM_004445.1 | NP_004436.1 |

In some embodiments, the present invention provides an isolated antibody that comprises at least one thioether crosslink and specifically binds to EphA2 and a compositions comprising this antibody. The antibodies of the invention can be monoclonal antibodies, human antibodies, humanized antibodies or chimeric antibodies. In some embodiments, the anti-EphA2 antibody of the invention is EA2. In some preferred embodiments, the EA2 antibody is human or humanized. In other embodiments, the is EA5. In some preferred embodiments, the EA5 antibody is human or humanized. Hybridomas producing the anti-EphA2 antibodies of the invention have been deposited with the American Type Culture Collection (ATCC, P.O. Box 1549, Manassas, Va. 20108) under the provisions of the Budapest Treaty on the International Recognition of the Deposit of Microorganisms for the Purposes of Patent Procedures, and assigned accession numbers, which are incorporated by reference, as shown in TABLE 3.

TABLE 3

| EphA2 Antibodies | Deposit No. | Date of Deposit |
|---|---|---|
| EA2.31 | PTA-4380 | May 22, 2002 |
| EA5.12 | PTA-4381 | May 22, 2002 |
| Eph099B-102.147 | PTA-4572 | Aug. 7, 2002 |
| Eph099B-208.261 | PTA-4573 | Aug. 7, 2002 |
| Eph099B-210.248 | PTA-4574 | Aug. 7, 2002 |
| Eph099B-233.152 | PTA-5194 | May 12, 2003 |
| Eph101.530.241 | PTA-4724 | Sep. 26, 2002 |

EphA2 is a 130 kDa receptor tyrosine kinase that is expressed in adult epithelia, where it is found at low levels and is enriched within sites of cell-cell adhesion (Zantek, et al, *Cell Growth & Differentiation* 10:629, 1999; Lindberg, et al., *Molecular & Cellular Biology* 10: 6316, 1990). EphA2 is upregulated on a large number of aggressive carcinoma cells. The anti-EphA2 antibodies of this invention can be used, for example, in the treatment of a variety of tumors, including breast, colon, prostate, lung and skin cancers, as well as to prevent metastasis.

The anti-EphA2 antibodies of this section can be made, formulated, administered, used therapeutically or used prophylactically as described in U.S. patent application Ser. No. 10/823,259, filed Apr. 12, 2004; U.S. patent application Ser. No. 10/823,254, filed on Apr. 12, 2004; U.S. patent application Ser. No. 10/436,782, filed on May 12, 2003 and published Feb. 12, 2004 as U.S. Pat. Pub. No. 2004/0028685; U.S. patent application Ser. No. 10/436,783, filed on May 12, 2003 and published May 13, 2004 as U.S. Pat. Pub. No. 2004/0091486; U.S. patent application Ser. No. 11/004,794, filed on Dec. 3, 2004; U.S. patent application Ser. No. 10/994, 129, filed on Nov. 19, 2004; U.S. patent application Ser. No. 11/004,795, filed on Dec. 3, 2004; and U.S. Provisional Application Nos. 60/662,517,60/622,711, 60/622,489, filed Oct. 27, 2004, the contents of which are hereby incorporated by reference in their entirety.

In some embodiments, the antibody comprises the amino acid sequence of the $V_H$ and $V_L$ chains of EA2. In other embodiments, the antibody comprises the amino acid sequence of the CDRs of the $V_H$ and $V_L$ chains of EA2. The amino acid sequences of the $V_H$ and $V_L$ chains of EA2 and the CDRs of the $V_H$ and $V_L$ chains of EA2 are listed in Table 1 and are provided in U.S. Patent. Publication No. 2004/0028685, published on Feb. 12, 2004, the contents of which are hereby incorporated by reference in its entirety.

The present invention provides an isolated antibody that comprises at least one thioether cross-link and specifically binds to an antigen of EphA4 and a compositions comprising this antibody. The antibodies of the invention can be monoclonal antibodies, human antibodies, humanized antibodies or chimeric antibodies. Hybridomas producing the anti-EphA4 antibodies of the invention have been deposited with the American Type Culture Collection (ATCC, P.O. Box 1549, Manassas, Va. 20108) on Jun. 4, 2004 under the provisions of the Budapest Treaty on the International Recognition of the Deposit of Microorganisms for the Purposes of Patent Procedures, and assigned accession number PTA-6044 and PTA-4381 and incorporated by reference.

EphA4 is a receptor tyrosine kinase that is expressed in brain, heart, lung, muscle, kidney, placenta, pancreas (Fox, et al, *Oncogene* 10:897, 1995) and melanocytes (Easty, et al., *Int. J. Cancer* 71:1061, 1997). EphA4 is overexpressed in a number of cancers. The anti-EphA4 antibodies of this section can be used, for example, to decrease the expression of EphA4 in the treatment of pancreatic cancers etc.

The anti-EphA4 antibodies of this section can be made, formulated, administered, used therapeutically or used prophylactically as described in U.S. patent application Ser. No. 10/863,729, filed Jun. 7, 2004; U.S. patent application Ser. No. 11/004,794, filed on Dec. 3, 2004; U.S. patent application Ser. Nos. 11/004,794 and 11/004,795, filed on Dec. 3, 2004, the contents of which are hereby incorporated by reference in their entirety.

The present invention provides an isolated antibody that comprises at least one thioether cross-link and specifically binds to an antigen of EphB4 and a compositions comprising this antibody. The antibodies of the invention can be monoclonal antibodies, human antibodies, humanized antibodies or chimeric antibodies.

The anti-EphB4 antibodies of this section can be made, formulated, administered, used therapeutically or used prophylactically as described in U.S. Patent Application Publication Nos. 2003/0207447, 2005/0249736, 2005/0164965 and 2005/0084873, International Application Publication No. WO 99/52541, U.S. Pat. Nos. 6,864,227 and 6,579,683, the contents of which are hereby incorporated by reference in their entirety.

5.4.2.7. Antibodies Comprising at Least One Thioether Cross-Link that Specifically Bind to IL-9 and Compositions Comprising the Same The present invention provides an isolated antibody that comprises at least one thioether cross-link and specifically binds to IL-9 and a compositions comprising this antibody. The thioether cross-link is described in detail in Section 5.2. The antibodies of the present invention can comprise one or multiple thioether cross-links. he thioether cross-link can link any two residues of the antibody. In certain embodiments, the residues linked by the thioether cross-link are natural residues. In preferred embodiments, two of the residues are cysteine residues. The thioether cross-link can be at any location of the antibodies where feasible according to the knowledge of those of skill in the art. In preferred embodiments, the thioether cross-link links a heavy chain and a light chain of the antibody. In particular preferred embodiments, the thioether cross-link links a cysteine of a heavy chain and a cysteine of a light chain of the antibody.

This antibody of the invention specifically binds to IL-9. The antibodies of the invention can be monoclonal antibodies, human antibodies, humanized antibodies or chimeric antibodies. In some preferred embodiments, the anti-IL-9 antibodies is MEDI-528. In some preferred embodiments, the anti-IL-9 antibodies is 7F3com-2H2.

In some embodiments, the antibody comprises the amino acid sequence of the $V_H$ and $V_L$ chains of 7F3com-2H2. In other embodiments, the antibody comprises the amino acid sequence of the CDRs of the $V_H$ and $V_L$ chains of 7F3com- 2H2. The amino acid sequences of the CDRs of the V$_H$ and V$_L$ chains of 7F3com-2H2 are listed in Table 1 and are provided in U.S. Patent. Publication No. 2005/002934, published on Jan. 16, 2005, the contents of which are hereby incorporated by reference in its entirety.

It has been shown that IL-9 may be a key mediator of asthma and may also contribute to other respiratory disorders including chronic obstructive pulmonary disease (COPD) and cystic fibrosis. The anti-IL-9 antibodies of this section may be used in the prophylaxis or treatment of asthma.

The anti-IL-9 antibodies of this section can be made, formulated, administered, used therapeutically or used prophylactically as described in U.S. patent application Ser. No. 10/823,253, filed Apr. 12, 2004 and published Jan. 6, 2005, as U.S. Pat. Pub. No. US 2005/0002934 A1; U.S. patent application Ser. No. 10/823, 810, filed on Apr. 12, 2004; U.S. Provisional Application Nos. 60/371,728 and 60/371,683, filed Apr. 12, 2002; and U.S. Provisional Application No. 60/561,845, filed Apr. 12, 2004, the contents of which are hereby incorporated by reference in their entirety.

5.4.2.8. Antibodies Comprising at Least One Thioether Cross-Link that have Therapeutic Utility Compositions Comprising the Same The invention also encompasses antibodies comprising at least one thioether cross-link that have therapeutic utility, including but not limited to antibodies listed in TABLE 4. These antibody listed in Table 3 can be engineered and/or enriched to comprise at least one thioether cross-link.

TABLE 4

THERAPEUTIC ANTIBODIES THAT CAN BE ENGINEERED ACCORDING TO THE METHODS OF THE INVENTION

| Company | Product | Disease | Target |
| --- | --- | --- | --- |
| Abgenix | ABX-EGF | Cancer | EGF receptor |
| AltaRex | OvaRex | ovarian cancer | tumor antigen CA125 |
| | BravaRex | metastatic cancers | tumor antigen MUC1 |
| Antisoma | Theragyn (pemtumomabytrrium-90) | ovarian cancer | PEM antigen |
| | Therex | breast cancer | PEM antigen |
| Boehringer Ingelheim | Blvatuzumab | head & neck cancer | CD44 |
| Centocor/J&J | Panorex | Colorectal cancer | 17-1A |
| | ReoPro | PTCA | gp IIIb/IIIa |
| | ReoPro | Acute MI | gp IIIb/IIIa |
| | ReoPro | Ischemic stroke | gp IIIb/IIIa |
| Corixa | Bexocar | NHL | CD20 |
| CRC Technology | MAb, idiotypic 105AD7 | colorectal cancer vaccine | gp72 |
| Crucell | Anti-EpCAM | cancer | Ep-CAM |
| Cytoclonal | MAb, lung cancer | non-small cell lung cancer | NA |
| Genentech | Herceptin | metastatic breast cancer | HER-2 |
| | Herceptin | early stage breast cancer | HER-2 |
| | Rituxan | Relapsed/refractory low-grade or follicular NHL | CD20 |
| | Rituxan | intermediate & high-grade NHL | CD20 |
| | MAb-VEGF | NSCLC, metastatic | VEGF |
| | MAb-VEGF | Colorectal cancer, metastatic | VEGF |
| | AMD Fab | age-related macular degeneration | CD18 |
| | E-26 (2$^{nd}$ gen. IgE) | allergic asthma & rhinitis | IgE |
| IDEC | Zevalin (Rituxan + yttrium-90) | low grade of follicular, relapsed or refractory, CD20-positive, B-cell NHL and Rituximab-refractory NHL | CD20 |
| ImClone | Cetuximab + innotecan | refractory colorectal carcinoma | EGF receptor |
| | Cetuximab + cisplatin & radiation | newly diagnosed or recurrent head & neck cancer | EGF receptor |

TABLE 4-continued

THERAPEUTIC ANTIBODIES THAT CAN BE ENGINEERED
ACCORDING TO THE METHODS OF THE INVENTION

| Company | Product | Disease | Target |
|---|---|---|---|
| | Cetuximab + gemcitabine | newly diagnosed metastatic pancreatic carcinoma | EGF receptor |
| | Cetuximab + cisplatin + 5FU or Taxol | recurrent or metastatic head & neck cancer | EGF receptor |
| | Cetuximab + carboplatin + paclitaxel | newly diagnosed non-small cell lung carcinoma | EGF receptor |
| | Cetuximab + cisplatin | head & neck cancer (extensive incurable local-regional disease & distant metasteses) | EGF receptor |
| | Cetuximab + radiation | locally advanced head & neck carcinoma | EGF receptor |
| | BEC2 + Bacillus Calmette Guerin | small cell lung carcinoma | mimics ganglioside GD3 |
| | BEC2 + Bacillus Calmette Guerin | melanoma | mimics ganglioside GD3 |
| | IMC-1C11 | colorectal cancer with liver metasteses | VEGF-receptor |
| ImmonoGen | nuC242-DM1 | Colorectal, gastric, and pancreatic cancer | nuC242 |
| ImmunoMedics | LymphoCide | Non-Hodgkins lymphoma | CD22 |
| | LymphoCide Y-90 | Non-Hodgkins lymphoma | CD22 |
| | CEA-Cide | metastatic solid tumors | CEA |
| | CEA-Cide Y-90 | metastatic solid tumors | CEA |
| | CEA-Scan (Tc-99m-labeled arcitumomab) | colorectal cancer (radioimaging) | CEA |
| | CEA-Scan (Tc-99m-labeled arcitumomab) | Breast cancer (radioimaging) | CEA |
| | CEA-Scan (Tc-99m-labeled arcitumomab) | lung cancer (radioimaging) | CEA |
| | CEA-Scan (Tc-99m-labeled arcitumomab) | intraoperative tumors (radio imaging) | CEA |
| | LeukoScan (Tc-99m-labeled sulesomab) | soft tissue infection (radioimaging) | CEA |
| | LymphoScan (Tc-99m-labeled) | lymphomas (radioimaging) | CD22 |
| | AFP-Scan (Tc-99m-labeled) | liver 7 gem-cell cancers (radioimaging) | AFP |
| Intracel | HumaRAD-HN (+ yttrium-90) | head & neck cancer | NA |
| | HumaSPECT | colorectal imaging | NA |
| Medarex | MDX-101 (CTLA-4) | Prostate and other cancers | CTLA-4 |
| | MDX-210 (her-2 overexpression) | Prostate cancer | HER-2 |
| | MDX-210/MAK | Cancer | HER-2 |

TABLE 4-continued

THERAPEUTIC ANTIBODIES THAT CAN BE ENGINEERED ACCORDING TO THE METHODS OF THE INVENTION

| Company | Product | Disease | Target |
|---|---|---|---|
| MedImmune | Vitaxin | Cancer | $\alpha v \beta_3$ |
| Merck KGaA | MAb 425 | Various cancers | EGF receptor |
|  | IS-IL-2 | Various cancers | Ep-CAM |
| Millennium | Campath (alemtuzumab) | chronic lymphocytic leukemia | CD52 |
| NeoRx | CD20-streptavidin (+ biotin-yttrium 90) | Non-Hodgkins lymphoma | CD20 |
|  | Avidicin (albumin + NRLU13) | metastatic cancer | NA |
| Peregrine | Oncolym (+ iodine-131) | Non-Hodgkins lymphoma | HLA-DR 10 beta |
|  | Cotara (+ iodine-131) | unresectable malignant glioma | DNA-associated proteins |
| Pharmacia Corporation | C215 (+ staphylococcal enterotoxin) | pancreatic cancer | NA |
|  | MAb, lung/kidney cancer | lung & kidney cancer | NA |
|  | nacolomab tafenatox (C242 + staphylococcal enterotoxin) | colon & pancreatic cancer | NA |
| Protein Design Labs | Nuvion | T cell malignancies | CD3 |
|  | SMART M195 | AML | CD33 |
|  | SMART 1D10 | NHL | HLA-DR antigen |
| Titan | CEAVac | colorectal cancer, advanced | CEA |
|  | TriGem | metastatic melanoma & small cell lung cancer | GD2-ganglioside |
|  | TriAb | metastatic breast cancer | MUC-1 |
| Trilex | CEAVac | colorectal cancer, advanced | CEA |
|  | TriGem | metastatic melanoma & small cell lung cancer | GD2-ganglioside |
|  | TriAb | metastatic breast cancer | MUC-1 |
| Viventia Biotech | NovoMAb-G2 radiolabeled | Non-Hodgkins lymphoma | NA |
|  | Monopharm C | colorectal & pancreatic carcinoma | SK-1 antigen |
|  | GlioMAb-H (+ gelonin toxin) | glioma, melanoma & neuroblastoma | NA |
| Xoma | Rituxan | Relapsed/refractory low-grade or follicular NHL | CD20 |
|  | Rituxan | intermediate & high-grade NHL | CD20 |
|  | ING-1 | adenomcarcinoma | Ep-CAM |

5.4.2.9. Antibodies Comprising at Least One Thioether Cross-Link that can be Used for Inflammatory Disorders or Autoimmune Diseases and Compositions Comprising the Same The invention further contemplates any of the antibodies known in the art for the treatment and/or prevention of autoimmune disease or inflammatory disease, wherein the antibodies comprise at least one thioether cross-link. A non-limiting example of the antibodies that are used for the treatment or prevention of inflammatory disorders which can be engineered according to the invention is presented in TABLE 5A, and a non-limiting example of the antibodies that are used for the treatment or prevention of autoimmune disorder is presented in Table 5B. These antibody listed in Table 5A and 5B can be engineered and/or enriched to comprise at least one thioether cross-link.

TABLE 5A

ANTIBODIES FOR INFLAMMATORY DISEASES AND AUTOIMMUNE DISEASES THAT CAN PRODUCED IN ACCORDANCE WITH THE INVENTION.

| Antibody Name | Target Antigen | Product Type | Isotype | Sponsors | Indication |
|---|---|---|---|---|---|
| 5G1.1 | Complement (C5) | Humanized | IgG | Alexion Pharm Inc | Rheumatoid Arthritis |
| 5G1.1 | Complement (C5) | Humanized | IgG | Alexion Pharm Inc | SLE |
| 5G1.1 | Complement (C5) | Humanized | IgG | Alexion Pharm Inc | Nephritis |
| 5G1.1-SC | Complement (C5) | Humanized | ScFv | Alexion Pharm Inc | Cardiopulmonary Bypass |
| 5G1.1-SC | Complement (C5) | Humanized | ScFv | Alexion Pharm Inc | Myocardial Infarction |
| 5G1.1-SC | Complement (C5) | Humanized | ScFv | Alexion Pharm Inc | Angioplasty |
| ABX-CBL | CBL | Human | | Abgenix Inc | GvHD |
| ABX-CBL | CD147 | Murine | IgG | Abgenix Inc | Allograft rejection |
| ABX-IL8 | IL-8 | Human | IgG2 | Abgenix Inc | Psoriasis |
| Antegren | VLA-4 | Humanized | IgG | Athena/Elan | Multiple Sclerosis |
| Anti-CD11a | CD11a | Humanized | IgG1 | Genentech Inc/Xoma | Psoriasis |
| Anti-CD18 | CD18 | Humanized | Fab'2 | Genentech Inc | Myocardial infarction |
| Anti-LFA1 | CD18 | Murine | Fab'2 | Pasteur-Merieux/Immunotech | Allograft rejection |
| Antova | CD40L | Humanized | IgG | Biogen | Allograft rejection |
| Antova | CD40L | Humanized | IgG | Biogen | SLE |
| BTI-322 | CD2 | Rat | IgG | Medimmune Inc | GvHD, Psoriasis |
| CDP571 | TNF-alpha | Humanized | IgG4 | Celltech | Crohn's |
| CDP571 | TNF-alpha | Humanized | IgG4 | Celltech | Rheumatoid Arthritis |
| CDP850 | E-selectin | Humanized | | Celltech | Psoriasis |
| Corsevin M | Fact VII | Chimeric | | Centocor | Anticoagulant |
| D2E7 | TNF-alpha | Human | | CAT/BASF | Rheumatoid Arthritis |
| Hu23F2G | CD11/18 | Humanized | | ICOS Pharm Inc | Multiple Sclerosis |
| Hu23F2G | CD11/18 | Humanized | IgG | ICOS Pharm Inc | Stroke |
| IC14 | CD14 | | | ICOS Pharm Inc | Toxic shock |
| ICM3 | ICAM-3 | Humanized | | ICOS Pharm Inc | Psoriasis |
| IDEC-114 | CD80 | Primatised | | IDEC Pharm/Mitsubishi | Psoriasis |
| IDEC-131 | CD40L | Humanized | | IDEC Pharm/Eisai | SLE |
| IDEC-131 | CD40L | Humanized | | IDEC Pharm/Eisai | Multiple Sclerosis |
| IDEC-151 | CD4 | Primatised | IgG1 | IDEC Pharm/Glaxo SmithKline | Rheumatoid Arthritis |
| IDEC-152 | CD23 | Primatised | | IDEC Pharm | Asthma/Allergy |
| Infliximab | TNF-alpha | Chimeric | IgG1 | Centocor | Rheumatoid Arthritis |
| Infliximab | TNF-alpha | Chimeric | IgG1 | Centocor | Crohn's |
| LDP-01 | beta2-integrin | Humanized | IgG | Millennium Inc (LeukoSite Inc.) | Stroke |
| LDP-01 | beta2-integrin | Humanized | IgG | Millennium Inc (LeukoSite Inc.) | Allograft rejection |
| LDP-02 | alpha4beta7 | Humanized | | Millennium Inc (LeukoSite Inc.) | Ulcerative Colitis |
| MAK-195F | TNF alpha | Murine | Fab'2 | Knoll Pharm, BASF | Toxic shock |
| MDX-33 | CD64 (FcR) | Human | | Medarex/Centeon | Autoimmune haematogical disorders |

TABLE 5A-continued

ANTIBODIES FOR INFLAMMATORY DISEASES AND AUTOIMMUNE DISEASES THAT CAN PRODUCED IN ACCORDANCE WITH THE INVENTION.

| Antibody Name | Target Antigen | Product Type | Isotype | Sponsors | Indication |
|---|---|---|---|---|---|
| MDX-CD4 | CD4 | Human | IgG | Medarex/Eisai/Genmab | Rheumatoid Arthritis |
| MEDI-507 | CD2 | Humanized | | Medimmune Inc | Psoriasis |
| MEDI-507 | CD2 | Humanized | | Medimmune Inc | GvHD |
| OKT4A | CD4 | Humanized | IgG | Ortho Biotech | Allograft rejection |
| OrthoClone OKT4A | CD4 | Humanized | IgG | Ortho Biotech | Autoimmune disease |
| Orthoclone/anti-CD3 OKT3 | CD3 | Murine | mIgG2a | Ortho Biotech | Allograft rejection |
| RepPro/Abciximab | gpIIbIIIa | Chimeric | Fab | Centocor/Lilly | Complications of coronary angioplasty |
| rhuMab-E25 | IgE | Humanized | IgG1 | Genentech/Novartis/Tanox Biosystems | Asthma/Allergy |
| SB-240563 | IL5 | Humanized | | GlaxoSmithKline | Asthma/Allergy |
| SB-240683 | IL-4 | Humanized | | GlaxoSmithKline | Asthma/Allergy |
| SCH55700 | IL-5 | Humanized | | Celltech/Schering | Asthma/Allergy |
| Simulect | CD25 | Chimeric | IgG1 | Novartis Pharm | Allograft rejection |
| SMART a-CD3 | CD3 | Humanized | | Protein Design Lab | Autoimmune disease |
| SMART a-CD3 | CD3 | Humanized | | Protein Design Lab | Allograft rejection |
| SMART a-CD3 | CD3 | Humanized | IgG | Protein Design Lab | Psoriasis |
| Zenapax | CD25 | Humanized | IgG1 | Protein Design Lab/Hoffman-La Roche | Allograft rejection |

TABLE 5B

ANTIBODIES FOR AUTOIMMUNE DISORDERS THAT CAN BE PRODUCED IN ACCORDANCE WITH THE INVENTION

| Antibody | Indication | Target Antigen |
|---|---|---|
| ABX-RB2 | | antibody to CBL antigen on T cells, B cells and NK cells fully human antibody from the Xenomouse |
| 5c8 (Anti CD-40 ligand antibody) | Phase II trials were halted in October 1999 examine "adverse events" | CD-40 |
| IDEC 131 | systemic lupus erythyematous (SLE) | anti CD40 humanized |
| IDEC 151 | rheumatoid arthritis | primatized; anti-CD4 |
| IDEC 152 | Asthma | primatized; anti-CD23 |
| IDEC 114 | Psoriasis | primatized anti-CD80 |
| MEDI-507 | rheumatoid arthritis; multiple sclerosis Crohn's disease Psoriasis | anti-CD2 |
| LDP-02 (anti-b7 mAb) | inflammatory bowel disease Chron's disease ulcerative colitis | a4b7 integrin receptor on white blood cells (leukocytes) |
| SMART Anti-Gamma Interferon antibody | autoimmune disorders | Anti-Gamma Interferon |
| Verteportin | rheumatoid arthritis | |
| MDX-33 | blood disorders caused by autoimmune reactions Idiopathic Thrombocytopenia Purpurea (ITP) autoimmune hemolytic anemia | monoclonal antibody against FcRI receptors |

TABLE 5B-continued

ANTIBODIES FOR AUTOIMMUNE DISORDERS THAT CAN BE PRODUCED IN ACCORDANCE WITH THE INVENTION

| Antibody | Indication | Target Antigen |
| --- | --- | --- |
| MDX-CD4 | treat rheumatoid arthritis and other autoimmunity | monoclonal antibody against CD4 receptor molecule |
| VX-497 | autoimmune disorders multiple sclerosis rheumatoid arthritis inflammatory bowel disease lupus psoriasis | inhibitor of inosine monophosphate dehydrogenase (enzyme needed to make new RNA and DNA used in production of nucleotides needed for lymphocyte proliferation) |
| VX-740 | rheumatoid arthritis | inhibitor of ICE interleukin-1 beta (converting enzyme controls pathways leading to aggressive immune response) |
| VX-745 | specific to inflammation involved in chemical signalling of immune response onset and progression of inflammation | inhibitor of P38MAP kinase mitogen activated protein kinase |
| Enbrel (etanercept) | | targets TNF (tumor necrosis factor) |
| IL-8 | | fully human monoclonal antibody against IL-8 (interleukin 8) |
| Apogen MP4 | | recombinant antigen selectively destroys disease associated T-cells induces apoptosis T-cells eliminated by programmed cell death no longer attack body's own cells specific apogens target specific T-cells |

5.5. Production of Polypeptides

The macromolecules of the present invention can be produced by any method or technique known in the art. For example, polypeptides can be chemically synthesized or recombinantly produced. See e.g., Sambrook et al., 1990. *Molecular Cloning: A Laboratory Manual* (Cold Spring Harbor Press, Cold Spring Harbor, N.Y.).

5.5.1 Methods of Producing Antibodies

The antibodies of the present invention can be produced by any method known in the art for the synthesis of antibodies, in particular, by chemical synthesis or preferably, by recombinant expression techniques.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas* 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with an antigen (either the full length protein or a domain thereof, e.g., the extracellular or the ligand binding domain) and once an immune response is detected, e.g., antibodies specific for the particular antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. Hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, monoclonal antibodies can be generated by culturing a hybridoma cell secreting an antibody of the invention wherein, preferably, the hybridoma is generated by fusing splenocytes isolated from a mouse immunized with the antigen with myeloma cells and then screening the hybridomas resulting from the fusion for hybridoma clones that secrete an antibody able to bind the antigen.

Antibody fragments of the present invention may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to an epitope of interest can be selected or identified with antigen, e.g., using labeled antigen or antigen bound or captured to a solid surface or bead. Examples of phage display methods that can be used to make the antibodies of the present invention include those disclosed in Brinkman et al., 1995, *J. Immunol. Methods* 182:41-50; Ames et al., 1995, *J. Immunol. Methods* 184:177; Kettleborough et al., 1994, *Eur. J. Immunol.* 24:952-958; Persic et al., 1997, *Gene* 187:9; Burton et al., 1994, *Advances in Immunology* 57:191-280; International Application No. PCT/GB91/01134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580, 717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

Phage may be screened for antigen binding activities. As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in International Publication No. WO 92/22324; Mullinax et al., 1992, *BioTechniques* 12:864; Sawai et al., 1995, *AJRI* 34:26; and Better et al., 1988, *Science* 240:1041 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lambda constant regions. Preferably, the vectors for expressing the VH or VL domains comprise an EF-1α promoter, a secretion signal, a cloning site for the variable domain, constant domains, and a selection marker such as neomycin. The VH and VL domains may also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444, 887 and 4,716,111; and International Publication Nos. WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Fremont, Calif.) and Medarex (Princeton, N.J.) can be engaged to provide human antibodies directed against a selected antigen using technology similar to that described above.

A chimeric antibody is a molecule in which different portions of the antibody are derived from different immunoglobulin molecules such as antibodies having a variable region derived from a non-human antibody and a human immunoglobulin constant region. Methods for producing chimeric antibodies are known in the art. See, e.g., Morrison, 1985, *Science* 229:1202; Oi et al., 1986, *BioTechniques* 4:214; Gillies et al., 1989, *J. Immunol. Methods* 125:191-202; and U.S. Pat. Nos. 6,311,415, 5,807,715, 4,816,567, and 4,816,397, which are incorporated herein by reference in their entirety. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519, 596; Padlan, 1991, *Molecular Immunology* 28(4/5):489-498; Studnicka et al., 1994, *Protein Engineering* 7:805; and Roguska et al., 1994, *PNAS* 91:969), and chain shuffling (U.S. Pat. No. 5,565,332).

Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann et al., 1988, Nature 332:323, which are incorporated herein by reference in their entireties.)

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including $IgG_1$, $IgG_2$, $IgG_3$ and $IgG_4$. Usually the constant domain is a complement fixing constant domain where it is desired that the humanized antibody exhibit cytotoxic activity, and the class is typically $IgG_1$. Where such cytotoxic activity is not desirable, the constant domain may be of the $IgG_2$ class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, J. Immunol. 169:1119-25, Caldas et al., 2000, Protein Eng. 13:353-60, Morea et al., 2000, Methods 20:267-79, Baca et al., 1997, J. Biol. Chem. 272:10678-84, Roguska et al., 1996, Protein Eng. 9:895-904, Couto et al., 1995, Cancer Res. 55 (23 Supp):5973s-5977s, Couto et al., 1995, Cancer Res. 55:1717-22, Sandhu, 1994, Gene 150:409-10, Pedersen et al., 1994, J. Mol. Biol. 235:959-73, Jones et al., 1986, Nature 321:522-525, Riechmann et al., 1988, Nature 332:323, and Presta, 1992, Curr. Op. Struct. Biol. 2:593-596. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323, which are incorporated herein by reference in their entireties.)

Further, the antibodies of the invention can, in turn, be utilized to generate anti-idiotype antibodies using techniques well known to those skilled in the art. (See, e.g., Greenspan & Bona, 1989, FASEB J. 7:437-444; and Nissinoff, 1991, J. Immunol. 147:2429-2438). The invention provides methods employing the use of polynucleotides comprising a nucleotide sequence encoding an antibody of the invention or a fragment thereof.

5.5.2 Recombinant Expression of an Antibody

Recombinant expression of an antibody of the invention, derivative, analog or fragment thereof, (e.g., a heavy or light chain of an antibody of the invention or a portion thereof or a single chain antibody of the invention), requires construction of an expression vector containing a polynucleotide that encodes the antibody. Once a polynucleotide encoding an antibody molecule or a heavy or light chain of an antibody, or portion thereof (preferably, but not necessarily, containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., International Publication Nos. WO 86/05807 and WO 89/01036; and U.S. Pat. No. 5,122,464) and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce an antibody of the invention. Thus, the invention includes host cells containing a polynucleotide encoding an antibody of the invention or fragments thereof, or a heavy or light chain thereof, or portion thereof, or a single chain antibody of the invention, operably linked to a heterologous promoter. In embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, *Gene* 45:101; and Cockett et al., 1990, *BioTechnology* 8:2). In a specific embodiment, the expression of nucleotide sequences encoding antibodies or fragments thereof which immunospecifically bind to and agonize is regulated by a constitutive promoter, inducible promoter or tissue specific promoter.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, *EMBO* 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be releastd from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, *PNAS* 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, *Methods in Enzymol.* 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI 38, BT483, Hs578T, HTB2, BT2O, NS1, T47D, NS0 (a murine myeloma cell line that does not endogenously produce any immunoglobulin chains), CRL7O3O and HsS78Bst cells.

The antibodies comprising at least one thioether cross-link can be recombinantly produced by any cell lines for producing antibodies known to those skilled in the art. It has been found that it is advantageous to produce the antibodies of the invention in melanoma cells. In certain embodiments, the antibodies of the invention are recombinantly produced in melanoma cells. In some embodiments, the antibodies of the invention are not recombinantly produced in CHO cell line. In other embodiments, the antibodies of the invention are not recombinantly produced in NS0 cell line.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, *Cell* 11:223), glutamine synthase, hypoxanthine guanine phosphoribosyltransferase (Szybalska & Szybalski, 1992, Proc. Natl. Acad. Sci. USA 48:202), and adenine phosphoribosyltransferase (Lowy et al., 1980, *Cell* 22:8-17) genes can be employed in tk-, gs-, hgprt- or aprt-cells, respectively. Also, antimetabolite resistance can be used as the basis of selection for the following genes: dhfr, which confers resistance to methotrexate (Wigler et al., 1980, *PNAS* 77:357; O'Hare et al., 1981, *PNAS* 78:1527); gpt, which confers resistance to mycophenolic acid (Mulligan & Berg, 1981, *PNAS* 78:2072); neo, which confers resistance to the aminoglycoside G-418 (Wu and Wu, 1991, *Biotherapy* 3:87; Tolstoshev, 1993, *Ann. Rev. Pharmacol. Toxicol.* 32:573; Mulligan, 1993, *Science* 260:926; and Morgan and Anderson, 1993, *Ann. Rev. Biochem.* 62: 191; May, 1993, *TIB TECH* 11:155-); and hygro, which confers resistance to hygromycin (Santerre et al., 1984, *Gene* 30:147). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., 1981, *J. Mol. Biol.* 150: 1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, *Mol. Cell. Biol.* 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, *Nature* 322:52; and Kohler, 1980, *PNAS* 77:2197). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

5.6. Methods of Producing/Enriching Macromolecules that Comprise at Least One Thioether Cross-Link and Compositions thereof The present invention provides methods for producing a composition enriched in a macromolecule, wherein the macromolecule comprises at least one thioether cross-link. The macromolecule can be produced by any method for producing a macromolecule known to those skilled in the art. In certain embodiments, the macromolecule is a polypeptide, which can be produced by any method for producing a polypeptide known to those skilled in the art. In further embodiments, the polypeptide is an antibody, which can be produced by any method for producing an antibody known to those skilled in the art, including the methods described above. The antibody in the composition can be any antibody comprising at least one thioether cross-link as described herein.

The present invention also provides a method for increasing the amount of a macromolecule which comprises at least one thioether cross-link in a composition. The macromolecule in the composition can be any macromolecule comprising at least one thioether cross-link as described in detail herein.

In some embodiments, the methods of the invention comprise incubating the composition at a temperature greater than 4° C. for a time sufficient to enrich the macromolecule that comprises at least one thioether cross-link. In certain embodiments, the composition is incubated at room temperature. In certain embodiments, the composition is incubated at a temperature greater than 101C. In certain embodiments, the composition is incubated at a temperature greater than 15° C. In certain embodiments, the composition is incubated at a temperature greater than 20° C. In certain embodiments, the composition is incubated at a temperature greater than 30° C. In certain embodiments, the composition is incubated at a temperature greater than 37° C. In certain embodiments, the composition is incubated at a temperature between 4° C. and 40° C., between 4° C. and 37° C., between 4° C. and 30° C., between 15° C. and 40° C., between 20° C. and 37° C., between 30° C. and 37° C., or between 37° C. and 40° C.

In some further embodiments, the composition is incubated at a temperature greater than 37° C. for more than three minutes. In some further embodiments, the composition is incubated at a temperature about 37° C. for more than one day. In some further embodiments, the composition is incubated at a temperature about 37° C. for between three minutes to one day, between three minutes to one month, or between one day to one month.

In certain embodiments, the composition is incubated at a temperature about 40° C. In some further embodiments, the composition is incubated at a temperature about 40° C. for more than three minutes. In some further embodiments, the composition is incubated at a temperature about 40° C. for more than one day. In some further embodiments, the composition is incubated at a temperature about 40° C. for more than one month. In some further embodiments, the composition is incubated at a temperature about 40° C. for between three minutes to one day, between three minutes to one month, or between one day to one month.

In another embodiments, the methods of the invention comprise incubating the composition at pH greater than 7 for a time sufficient to enrich the macromolecule that comprises at least one thioether cross-link. In certain embodiments, the methods of the invention comprise incubating the composition at a pH greater than 8. In some further embodiments, the methods of the invention comprise incubating the composition at a pH greater than 9. In another embodiments, the methods of the invention comprise incubating the composition at a pH greater than 10. In certain embodiments, the methods of the invention comprise incubating the composition at a pH between 7 and 10, between 7 and 9, between 8 and 9, and between 8 and 10. In certain embodiments, the methods of the invention comprise incubating the composition at a pH greater than 7 for more than three minutes. In some further embodiments, the methods of the invention comprise incubating the composition at a pH greater than 7 for more than one hour. In some further embodiments, the methods of the invention comprise incubating the composition at a pH greater than 7 for between three minutes and one hour, between three minutes and one day, and between one hour and one day.

In another embodiments, the method comprises contacting the composition with a reducing agent. The reducing agent can be any reducing agent in connection with preparation of proteins, as known by those skilled in the art. In certain embodiments, the reducing agent is selected from the group consisting of β-mercaptoethanol (BME), dithiothreitol (DTT), NEM, tris(2-carboxyethyl)phosphine (TCEP), and dithioerythritol (DTE).

In a further embodiments, the method of the invention comprise incubating the composition at a temperature greater than 4° C. and at a pH greater than 7 for a time sufficient to enrich the macromolecule that comprises at least one thioether cross-link.

In another embodiments, the method of invention comprises incubating the composition at a temperature greater than 4° C. for a time sufficient to enrich the macromolecule that comprises at least one thioether cross-link and contacting the composition with a reducing agent.

In another embodiments, the method of invention comprises incubating the composition at a pH greater than 7 for a time sufficient to enrich the macromolecule that comprises at least one thioether cross-link and contacting the composition with a reducing agent.

The invention provides methods for producing macromolecules comprising at one thioether cross-link, the methods comprising incubating the macromolecules in a buffer component such as phosphate buffer or an analogous buffer. The invention also provides methods for enriching for macromolecules comprising at least one thioether cross-link, the methods comprising incubating the macromolecules in a buffer component such as phosphate buffer or an analogous buffer. In certain embodiments, the buffer component is phosphate buffer. In specific embodiments, the buffer component is not a His buffer. In accordance with the invention, the incubation may be performed at the pHs and/or temperatures disclosed supra. Further, in certain embodiments, the macromolecule may be contacted with a denaturing reagent such as described above.

In certain embodiments, the present invention provides methods of isolating a macromolecule comprising a thioether cross-link. The macromolecule comprising the thioether cross-link can be prepared according to any of the methods described above. The macromolecule can be isolated by any method for purifying the macromolecule apparent to one of skill in the art. For instance, a polypeptide comprising a thioether cross-link can be purified according to standard polypeptide purification techniques apparent to those of skill in the art. Such techniques include, but are not limited to, chromatography, ion exchange chromatography, size exclusion chromatography and affinity chromatography.

In certain embodiments, macromolecules comprising thioether cross-links can be purified from macromolecules that do not comprise thioether cross-links under denaturing conditions. Useful techniques include gel electrophoresis, SDS-PAGE and capillary gel electrophoresis. The purified macromolecules comprising thioether cross-links can be renatured according to techniques known to those of skill in the art. Advantageously, the stability of the thioether cross-link can permit more vigorous denaturing and renaturing than what would be tolerated by macromolecules comprising disulfide bonds.

In further embodiments, macromolecules comprising thioether cross-links can be purified from macromolecules that do not comprise thioether cross-links under native conditions. The purification can be according to any method of purification apparent to those of skill in the art. For instance, certain compositions comprising macromolecules that comprise thioether cross-links and macromolecules that do not comprise thioether cross-links can be incubated under reducing conditions. Reduction of the macromolecules that do not comprise thioether cross-links can lead to changes in quaternary or tertiary structure that permit resolution of the macromolecules that comprise thioether cross-links from the macromolecules that do not comprise thioether cross-links. In further embodiments, macromolecules that comprise thioether cross-links can be purified by affinity chromatography specific for the thioether cross-link. For instance, in certain embodiments antibodies specific for a thioether cross-link bond can be used to purify a macromolecules that comprises a thioether cross-link according to antibody affinity purification techniques known to those of skill in the art. Antibodies specific for a thioether cross-link bond can be prepared according to standard immunological techniques using, for instance, immunogenic molecules comprising a thioether cross-link. Such immonogenic molecules, for instance, peptides or polypeptides, can be prepared according to the techniques described herein.

In further embodiments, macromolecules comprising thioether cross-links can be prepared synthetically or semi-synthetically according to techniques apparent to those of skill in the art. For instance, peptides or polypeptides comprising thioether cross-links can be prepared by standard solution or solid phase synthetic techniques. Activated precursor residues comprising thioether cross-links can be prepared according to synthetic techniques apparent to those of skill in the art. The peptides or polypeptides can be used themselves or incorporated into larger macromolecules according to techniques known to those of skill in the art.

5.7. Methods of Decreasing the Amount of Macromolecules that Comprise at Least One Thioether Cross-Link The present invention further provides a method for decreasing the amount of an antibody which comprises at least one thioether cross-link in a composition resulting from a first purification method. In certain embodiments, the method comprises carrying out a second purification method identical to said first purification method except that at least one step of said second purification method is carried out at a lower temperature and pH than the corresponding step in said first purification method, wherein said second purification method results in a lower level of said antibody species than said first purification method. The purification method can be any purification method for antibodies known in the art. Exemplary purification methods include, but are not limited to, chromatography, ion exchange chromatography, size exclusion chromatography and affinity chromatography.

5.8. Use of the Antibodies and Compositions of the Present Invention

The present invention provides macromolecules comprising at least one thioether cross-link and compositions comprising the macromolecules of the present invention. The macromolecules and compositions of the present invention can be used in any context that those of skilled in the art recognize, for example, diagnosis or therapy etc.

The present invention provides isolated antibodies comprising at least one thioether cross-link and compositions comprising the antibodies of the present invention. The antibodies and compositions of the present invention can be used in any context that those of skilled in the art recognize. For example, the antibodies and compositions of the invention can be used directly against a particular antigen. The antibodies and compositions of the invention can also be used in diagnostic assays either in vivo or in vitro for detection/identification of the expression of an antigen in a subject or a biological sample (e.g., cells or tissues). The antibodies and compositions of the present invention can be used alone or in combination with other therapies for treating, managing, preventing or ameliorating a disorder or one or more symptoms thereof.

The present invention provides a fusion protein and a composition comprising the same, wherein the fusion protein comprises an Fc domain of an antibody or a fragment thereof, and wherein the Fc domain or Fc domain fragment comprises at least one thioether cross-link. The present invention also provides a fusion protein and a composition comprises an $C_H1$, $C_H2$, $C_H3$ and/or $C_L$ domain of an antibody, and wherein the $C_H1$, $C_H2$, $C_H3$ and/or $C_L$ domain comprises at least one thioether cross-link. In certain embodiments, the fusion protein comprises two, three or all of the domains of $C_H1$, $C_H2$, $C_H3$ or $C_L$. The fusion protein and compositions of the present invention can be used in any context that those of skilled in the art recognize, such as diagnosis or therapy etc.

The present invention provides methods for preventing, managing, treating, or ameliorating a disorder comprising administering to a subject in need thereof one or more antibodies of the invention alone or in combination with one or more therapies (e.g., one or more prophylactic or therapeutic agents) other than an antibody of the invention. The present invention also provides compositions comprising one or more antibodies of the invention and one or more prophylactic or therapeutic agents other than antibodies of the invention and methods of preventing, managing, treating, or ameliorating a disorder or one or more symptoms thereof utilizing said compositions. Therapeutic or prophylactic agents include, but are not limited to, small molecules, synthetic drugs, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides) antibodies, synthetic or natural inorganic molecules, mimetic agents, and synthetic or natural organic molecules.

Any therapy which is known to be useful, or which has been used or is currently being used for the prevention, management, treatment, or amelioration of a disorder or one or more symptoms thereof can be used in combination with an antibody or a composition of the invention in accordance with the invention described herein. See, e.g., Gilman et al., Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories, Rahway, N.J., 1999; Cecil Textbook of Medicine, 20th Ed., Bennett and Plum (eds.), W. B. Saunders, Philadelphia, 1996 for information regarding therapies (e.g., prophylactic or therapeutic agents) which have been or are currently being used for preventing, treating, managing, or ameliorating a disorder or one or more symptoms thereof. Examples of such therapies include, but are not limited to, immunomodulatory agents, anti-inflammatory agents (e.g., adrenocorticoids, corticosteroids (e.g., beclomethasone, budesonide, flunisolide, fluticasone, triamcinolone, methlyprednisolone, prednisolone, prednisone, hydrocortisone), glucocorticoids, steroids, non-steriodal anti-inflammatory drugs (e.g., aspirin, ibuprofen, diclofenac, and COX-2 inhibitors), anti-cancer agents, pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents, and antibiotics (e.g., dactinomycin (formerly actinomycin), bleomycin, erythomycin, penicillin, mithramycin, and anthramycin (AMC)).

In a specific embodiment, the present invention provides administering one or more humanized anti-RSV antibodies to a subject, preferably a human subject, for preventing, treating, managing, or ameliorating a RSV infection or one or more symptoms thereof in a subject. In one embodiment, the invention encompasses a method of preventing, treating, managing, or ameliorating a RSV infection or one or more symptoms thereof, said method comprising administering to a subject in need thereof a dose of a prophylactically or therapeutically effective amount of one or more humanized anti-RSV antibodies. In another embodiment, the invention provides a method of preventing, treating, managing, or ameliorating a RSV infection or one or more symptoms thereof, said method comprising administering a prophylactically or therapeutic effective amount of one or more humanized anti-RSV antibodies and another therapy.

In a specific embodiment, the present invention provides administering one or more humanized anti-CD2 antibodies to a subject, preferably a human subject, for preventing, treating, managing, or ameliorating T cell lymphoma related conditions or one or more symptoms thereof in a subject. In one embodiment, the invention encompasses a method of preventing, treating, managing, or ameliorating T cell lymphoma related conditions or one or more symptoms thereof, said method comprising administering to a subject in need thereof a dose of a prophylactically or therapeutically effective amount of one or more humanized anti-CD2 antibodies. In another embodiment, the invention provides a method of preventing, treating, managing, or ameliorating T cell lymphoma related conditions or one or more symptoms thereof, said method comprising administering a prophylactically or therapeutic effective amount of one or more humanized anti-CD2 antibodies and another therapy.

In a specific embodiment, the present invention provides administering one or more humanized anti-IL-9 antibodies to a subject, preferably a human subject, for preventing, treating, managing, or ameliorating a respiratory condition or one or more symptoms thereof. In one embodiment, the invention encompasses a method of preventing, treating, managing, or ameliorating a respiratory disorder or one or more symptoms thereof (e.g., an allergy, wheezing, and asthma), said method comprising administering to a subject in need thereof a dose of a prophylactically or therapeutically effective amount of one or more humanized anti-IL-9 antibodies. In another embodiment, the invention provides a method of preventing, treating, managing, or ameliorating a respiratory infection or one or more symptoms thereof, said method comprising administering a prophylactically or therapeutic effective amount of one or more humanized anti-IL-9 antibodies.

In a specific embodiment, the present invention provides administering one or more humanized anti-EphA2 antibodies to a subject, preferably a human subject, for preventing, treating, managing, or ameliorating a hyperproliferative cell disease or one or more symptoms thereof. In one embodiment, one or more humanized anti-EphA2 antibodies are administered alone or in combination with other agents to a subject to prevent, treat, manage, or ameliorate cancer or one or more symptoms thereof (see, e.g., U.S. application Ser. No. 10/436, 782, which is incorporated herein by reference in its entirety). In another embodiment, one or more humanized anti-EphA2 antibodies are administered alone or in combination with other agents to a subject to prevent, treat, manage, or ameliorate a disorder involving non-neoplastic hyperproliferative cells, in particular hyperproliferative epithlial and endothelial cells, or one or symptoms thereof (see e.g., U.S. Application Ser. No. 60/462,024, which is incorporated herein by reference in its entirety). In yet another embodiment, one or more humanized anti-EphA2 antibodies are used for diagnostic or screening purposes.

In a specific embodiment, the present invention provides administering one or more humanized anti-EphA4 antibodies to a subject, preferably a human subject, for preventing, treating, managing, or ameliorating a cancer such as a pancreatic cancer or one or more symptoms thereof in a subject. In one embodiment, the invention encompasses a method of preventing, treating, managing, or ameliorating a cancer such as a pancreatic cancer or one or more symptoms thereof, said method comprising administering to a subject in need thereof a dose of a prophylactically or therapeutically effective amount of one or more humanized anti-EphA4 antibodies. In another embodiment, the invention provides a method of preventing, treating, managing, or ameliorating a cancer such as a pancreatic cancer or one or more symptoms thereof, said method comprising administering a prophylactically or therapeutic effective amount of one or more humanized anti-EphA4 antibodies and another therapy.

In a specific embodiment, the present invention provides administering one or more humanized anti-EphB4 antibodies to a subject, preferably a human subject, for preventing, treating, managing, or ameliorating a cancer or one or more symptoms thereof, or inhibiting angiogenesis in a subject. In one embodiment, the invention encompasses a method of preventing, treating, managing, or ameliorating a cancer or one or more symptoms thereof, or inhibiting angiogenesis, said method comprising administering to a subject in need thereof a dose of a prophylactically or therapeutically effective amount of one or more humanized anti-EphB4 antibodies. In another embodiment, the invention provides a method of preventing, treating, managing, or ameliorating a cancer or one or more symptoms thereof, or inhibiting angiogenesis, said method comprising administering a prophylactically or therapeutic effective amount of one or more humanized anti-EphB4 antibodies and another therapy.

The antibodies and compositions of the invention can be used directly against a particular antigen. In some embodiments, the antibodies and compositions of the invention belong to a subclass or isotype that is capable of mediating the lysis of cells to which the antibody binds. In a specific embodiment, the antibodies of the invention belong to a subclass or isotype that, upon complexing with cell surface proteins, activates serum complement and/or mediates antibody dependent cellular cytotoxicity (ADCC) by activating effector cells such as natural killer cells or macrophages.

The biological activities of antibodies are known to be determined, to a large extent, by the constant domains or Fc region of the antibody molecule (Uananue and Benacerraf, Textbook of Immunology, 2nd Edition, Williams & Wilkins, p. 218 (1984)). This includes their ability to activate complement and to mediate antibody-dependent cellular cytotoxicity (ADCC) as effected by leukocytes. Antibodies of different classes and subclasses differ in this respect, as do antibodies from the same subclass but different species; according to the present invention, antibodies of those classes having the desired biological activity are prepared. Preparation of these antibodies involves the selection of antibody constant domains and their incorporation in the humanized antibody by known technique. For example, mouse immunoglobulins of the IgG3 and IgG2a class are capable of activating serum complement upon binding to the target cells which express the cognate antigen, and therefore humanized antibodies which incorporate IgG3 and IgG2a effector functions are desirable for certain therapeutic applications.

In some embodiments, the antibodies and compositions of this invention are useful in passively immunizing patients.

The antibodies and compositions of the invention can also be used in diagnostic assays either in vivo or in vitro for detection/identification of the expression of an antigen in a subject or a biological sample (e.g., cells or tissues). Non-limiting examples of using an antibody, or a composition comprising an antibody in a diagnostic assay are given in U.S. Pat. Nos. 6,392,020; 6,156,498; 6,136,526; 6,048,528; 6,015,555; 5,833,988; 5,811,310; 8 5,652,114; 5,604,126; 5,484,704; 5,346,687; 5,318,892; 5,273,743; 5,182,107; 5,122,447; 5,080,883; 5,057,313; 4,910,133; 4,816,402; 4,742,000; 4,724,213; 4,724,212; 4,624,846; 4,623,627; 4,618,486; 4,176,174 (all of which are incorporated herein by reference). Suitable diagnostic assays for the antigen and its antibodies depend on the particular antibody used. Non-limiting examples are an ELISA, sandwich assay, and steric inhibition assays. For in vivo diagnostic assays using the antibodies of the invention, the antibodies may be conjugated to a label that can be detected by imaging techniques, such as X-ray, computed tomography (CT), ultrasound, or magnetic resonance imaging (MRI). The antibodies of the invention can also be used for the affinity purification of the antigen from recombinant cell culture or natural sources.

6. EXAMPLES

The following examples are offered to illustrate this invention and not to be construed in any way as limiting the scope of this invention.

6.1. Identification, Isolation, Characterization of Antibodies that Comprise a Thioether Cross-Link and Specifically Bind to an Antigen of RSV This example illustrates the identification, isolation, characterization of antibodies that comprise a thioether cross-link and that specifically bind to an antigen of RSV. Motavizumab is used in this example. As discussed in the sections above, motavizumab is an IgG1 monoclonal antibody produced by recombinant DNA technology that specifically binds to an epitope in the A antigenic site of the fusion (F) protein of RSV. Motavizumab antibody is a humanized antibody and consists of the CDR regions specific for the targeted antigen and the constant regions of a human γ1 heavy chain and κ light chain. The monoclonal antibody has two inter-chain disulfide bonds to link heavy and light chains, and another two inter-chain disulfide bonds at the hinge region.

6.1.1 Identification of the Antibody Comprising a Thioether Cross-Link 6.1.1.1. By Reducing CGE Reducing Capillary Gel Electrophoresis (rCGE) was performed. Monoclonal antibody (Mab) samples were diluted into sample dilution buffer containing SDS in the presence of β-mercaptoethanol, heated in a boiling water bath for 10 min, and cooled prior to injection to a HP 3D capillary electrophoresis system (Agilent Technologies, Palo Alto, Calif.) (12-14). Electromigration injection was performed at −10.0 kV for 40 sec. The separation took place in an electric field of 390 V/cm for 22 min at 50° C. in a Hewlett-Packard extended light path fused silica capillary (50 μm I.D., 38.5 cm total length, 30 cm effective length). Detection was at 220 nm. Molecular weight markers were also analyzed: lysozyme (144,000 kDa), trypsin inhibitor (21,500 Da), carbonic anhydrase (31,000 Da), ovalbumin (45,000 Da), serum albumin (66,200 Da), phosphorylase B (97,000 Da), β-galactosidase (116,000 Da), and myosin (200,000 Da).

Figure 1A:
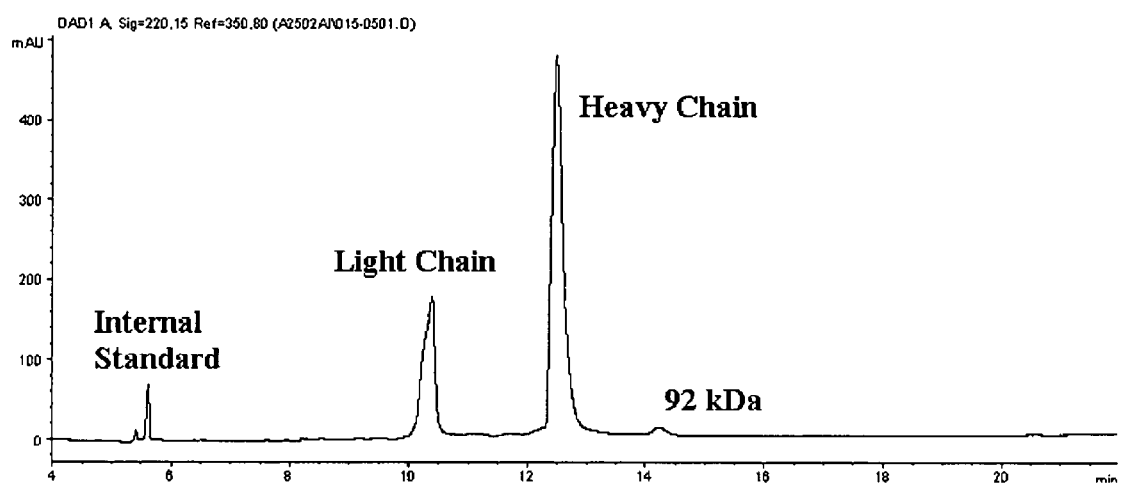

CGE utilizes a proprietary polymer solution that creates a dynamic sieving effect that is analogous to the cross-linked polyacrylamide sieving used in conventional slab gel electrophoresis. Both CGE and SDS-PAGE gel systems provide similar information such as fragmentation or aggregation events in the monoclonal antibody by calibrating the system with molecular weight markers. However, the results are more reproducible and easier to quantify when a monoclonal antibody is analyzed by reducing CGE (12-14, 18). rCGE produces a peak pattern that correlates to the migration times of the heavy and light chain of the monoclonal antibody. Three major bands are expected upon analysis of an Mab by rCGE: bands representing the heavy chain, the light chain, and the internal standard (benzoic acid). Analysis of a Mab by rCGE is shown in FIG. 1A. Bands (peaks) were seen at 5.6 min, 11 min, and 13 min corresponding to the internal standard, light chain, and heavy chain, respectively. In addition, an unexpected band was observed at 14.5 min corresponding to an apparent molecular weight of 92 kDa based on the molecular weight markers (not shown). This additional band was usually present at the 0.5-2% level of total protein.

6.1.2 By SDS-PAGE

The monoclonal antibody was also analyzed by reducing SDS-PAGE (FIG. 1B) followed by western blotting to verify that the additional band was product-related.

In SDA-PAGE analysis, Mab samples were diluted into sample dilution buffer containing 2% SDS in the presence or absence of 5% 2-mercaptoethanol. The resulting samples were heated to 80° C. for 10 min, cooled, and separated on a 4-20% polyacrylamide gradient gel (Novex) at 2 μg of protein per lane (15). The gels were then stained with Coomassie Blue, destained, and densitometry was performed. Molecular weight markers used were: myosin (200,000 Da), β-galactosidase (116,000 Da), phosphorylase b (97,400 Da), bovine serum albumin (66,200 Da), ovalbumin (45,000 Da), carbonic anhydrase (31,000 Da), soybean trypsin inhibitor (21, 500 Da), lysozyme (14,400 Da), and aprotinin (6,500 Da).

Western blot was performed. The SDS-PAGE gel was transferred to a polyvinylidene difluoride (PVDF) membrane (Pierce) by electroblotting (constant current 250 mA/blot) for 30 min in 25 mM Tris, 192 mM glycine and 20% methanol solution (16). The PVDF membrane was blocked for 1 hr at ambient temperature in 1×Tris-buffered saline (Bio-Rad, Hercules, Calif.) and 0.05% Tween-20 (TBST). The blot was incubated with biotin labeled light chain or heavy chain specific IgG (Kirkegaard & Perry, Gaithersburg, Md.) at a 1:1000 dilution for 2 hrs. The membrane was washed 3× with TBST, and then incubated with streptavidin and alkaline phosphatase (Pierce) at 1:5000 for 2 hrs at ambient temperature (17). Alkaline phosphatase activity was revealed by 5-bromo-4-chloro-3'-indolylphosphate p-toluidine salt/nitro-blue tetrazolium chloride (BCIP/NBT) development solution (Kirkegaard & Perry).

Figure 1B:
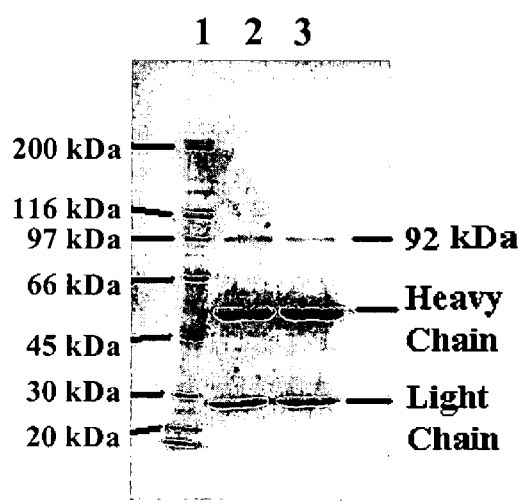
Figure 1C:
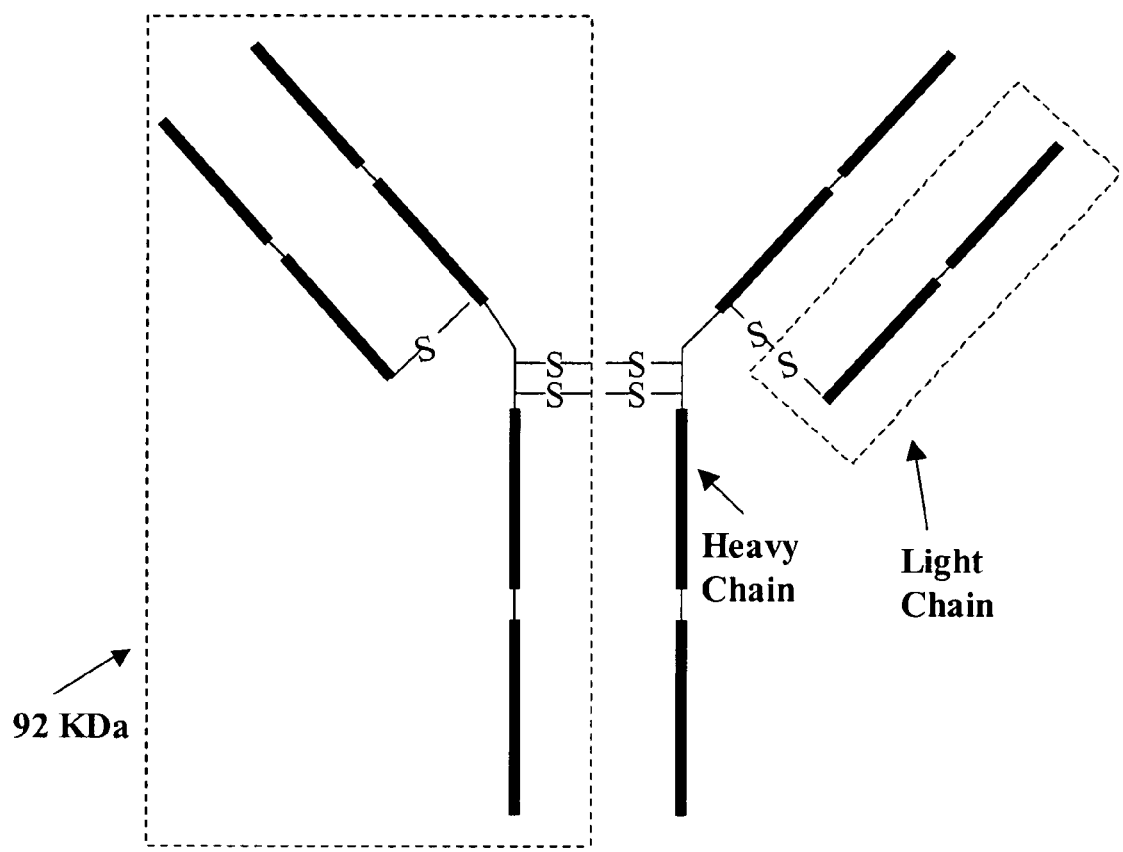

Similar to the results obtained from the rCGE, an additional band with an apparent molecular weight of 92 kDa was observed on the reduced SDS-PAGE gel in addition to the heavy and light chains (FIG. 1B). The 92 kDa band was further evaluated by western blotting, and shown to be immunoreactive to both heavy and light chain specific antibodies. When more powerful reducing agents were used (e.g., DTT, NEM), no change in the 9d2 kDa band was seen. The results indicated that the 92 kDa band may be a cross-linked species of the heavy and light chains (FIG. 1C).

6.1.3 Separation of Antibody Cross-Linked Species by Size Exclusion Chromatography (SEC)

To further investigate the nature of the 92 kDa band observed in rCGE and reducing SDS-PAGE, the heavy-light (H-L) species was separated for detailed characterization by SEC.

Figure 2:
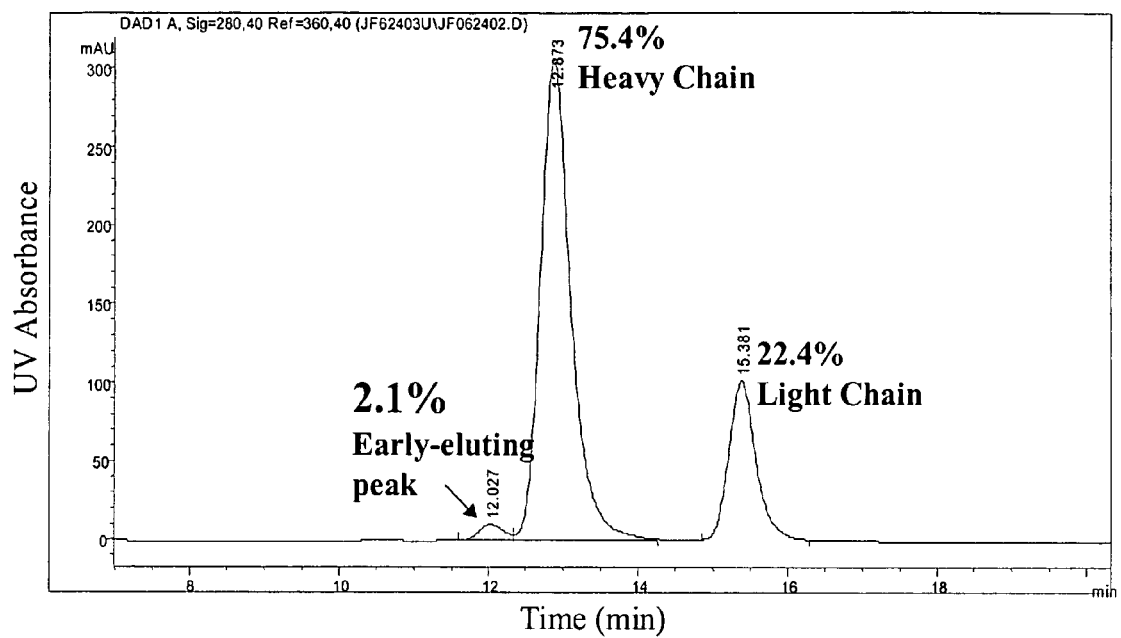
FIG. 2 shows size exclusion chromatogram of a reduced and alkylated monoclonal antibody motavizumab.

Size exclusion chromatography (SEC) was performed, Mab samples (53 mg/mL, 10 mg) were mixed with 630 μL of 8 M guanidine hydrochloride and 130 mM Tris (pH 7.6), 40 μL of water and 120 μL of 500 mM DTT and incubated at 37° C. for 1 hr. Neat 4-vinylpyridine (20 μL) was added to the sample and the incubation continued for 1 hr at ambient temperature in the dark. The reduced and alkylated antibody was dialyzed in 500 mL of 6 M guanidine hydrochloride for 2 hrs at 4° C. using a 10,000 MWCO dialysis cassette, and injected onto a size exclusion G3000 SW$_{XL}$ column (5 μm, 300 Å, 7.8×300 mm, TosoHaas). The mobile phase was 6 M guanidine hydrochloride and 1 M phosphaste (pH 6.8), running isocratically at a flow rate of 0.5 mL/min. The early-eluting fraction before the heavy and light chain peaks was detected by UV absorbance at 280 nm and collected for further characterization. The collected SEC fraction was concentrated using a Microcon-YM-30 filter unit and re-injected onto the TosoHaas G3000 SW$_{XL}$ column to verify identity and purity. Separation of Cross-linked Species by Size Exclusion Chromatography As indicated by rCGE, the protein species was present at a low level and could only be separated after the antibody was reduced; thus, it was challenging to obtain enough material for characterization. SEC was the method of choice to collect the H-L species. The denatured, reduced and alkylated monoclonal antibody was separated by SEC using a mobile phase containing 6 M guanidine to keep the reduced heavy and light chains, including the modified species, from precipitating and aggregating (FIG. 2). The heavy and light chain peaks were detected at 12.7 min and 15.4 min, respectively, and an additional peak was observed 12 min. This early-eluting peak was present at 2.1% level, while the heavy chain was present at 75.4% and the light chain at 22.4%. The early-eluting peak should have a higher molecular weight than the heavy and light chains because higher MW compounds pass through the column faster. The early-eluting peak was collected for further characterization.

6.1.4 Characterization of the Antibody Comprising a Thioether Cross-Link from SEC Purification The early-eluting peak in the SEC profile was analyzed by reducing SDS-PAGE, western blot, LC-MS, and tryptic peptide mapping with tandem mass spectrometry. The SEC fraction showed a band with an apparent molecular weight of 92 kDa by reducing SDS-PAGE. Upon western blot, this band was reactive to both heavy and light chain specific detection antibodies. This data indicated that the SEC fraction was the cross-linked species observed by rCGE and reducing SDS-PAGE.

6.1.4.1. Molecular Weight Determination by LC-ESI-MS

The Fab fragment of the antibody was prepared. Mab (1 mg) was digested with papain (Sigma) at an enzyme to protein ratio of 1:100 in 500 μL of phosphate buffer, pH 7.1 in the presence of 2.45 mg/mL cysteine at 37° C. for 1 hr. The papain digest was loaded onto a HiTrap NHS-activated HP affinity column coupled with Protein L using 2 mM phosphate, pH 7.2. The Fab portion bound to the Protein L column was eluted by 100 mM phosphate, pH 2.0, and collected, neutralized with 2 M Tris, pH 10, and concentrated with a 30,000 MWCO Microcon filter unit.

On-line LC-MS analysis of the SEC fraction and Fab fragment was performed using an Agilent 1100 HPLC system (Agilent Technologies, Palo Alto, Calif.) and ThermoElectron LCQDuo or LTQ ion trap mass spectrometer (Thermo Electron, San Jose, Calif.). The SEC fraction was analyzed on a reversed phase C18 column (Jupiter, 5 μm, 300 Å, 2×250 mm, Phenomenex) connected to a UV detector followed by the LCQ mass spectrometer The Fab fragment was analyzed on a Poroshell reversed phase 300-SB-C3 column (5 μm 300 Å, 2.1×75 mm, Agilent Technologies) followed by the LTQ mass spectrometer. The HPLC system used two different mobile phases: mobile phase A (0.1% TFA in water) and mobile phase B (0.1% TFA in acetonitrile). The samples were separated using a linear gradient of mobile phase B with a flow rate of 200 μL/min. The eluted proteins were monitored by UV detection at 220 nm and directed to the mass spectrometer, which was operated in positive ion mode. The deconvolution program of Bioworks version 3.1 (Thermo Electron) was used to deconvolute the mass spectra to obtain the molecular masses of the proteins.

The actual molecular weight of the early-eluting peak in the SEC profile was determined by LC-ESI-MS analysis. After mass spectrum deconvolution, a molecular weight of 75,860 Da was obtained, which is consistent with the combined molecular weights of the alkylated heavy and light chains. This result proves that the 92 kDa band observed in the rCGE and reducing SDS-PAGE is a cross-linked species containing one heavy and one light chain with an actual molecular weight of 75 kDa. It has been reported in the literature that during SDS-PAGE analysis, a half-antibody molecule migrates at 64 kDa with no heating, but migrates at 92 kDa with heating in SDS. (9). This phenomenon may be explained by the work of Pitt-Rivers and Impiombato (19), who demonstrated that proteins bind to 90-100% of their weight of SDS under native conditions, but reduction of all the disulfide bonds present results in more binding of SDS (up to 1.4 times the weight of the protein). It agrees with the observation that the apparent MW of the half-antibody (after heating) on the reducing SDS-PAGE is higher than its actual MW.

6.1.4.2. Peptide Mapping with Tandem Mass Spectrometry

To further investigate the nature of the cross-link modification, the SEC fraction was digested and analyzed by tryptic peptide mapping with tandem mass spectrometry.

Two different procedures were used for peptide mapping: tryptic peptide mapping for reduced samples, and Lys-C peptide mapping for non-reduced Fab samples. In the tryptic peptide mapping procedure, the reduced and alkylated antibody and the concentrated SEC fraction of interest were each dialyzed into 6 M urea containing 100 mM Tris buffer (pH 8.0) using 10,000 MWCO dialysis cassettes for 2 h at 4° C. The dialyzed fraction was mixed with 50 mM Tris buffer (pH 8.1) in the ratio of sample/Tris buffer 1:2 v/v. Trypsin (1 μg/μL trypsin in 1 mM HCl) was immediately added at a protein substrate to enzyme ratio of 25:1. The digestion proceeded for 4-5 hrs at 37° C. and was quenched by adding trifluoroacetic acid (TFA) to a final TFA concentration of 2%. For the Lys-C mapping procedure, the Fab fraction was digested by Lys-C (Wako Chemicals) at a protein to enzyme ratio of 10:1 in 5 M urea, 25 mM Tris-HCl and 1 mM EDTA, pH 8.5, at 37° C. for 8 h.

The on-line LC-MS/MS analysis of tryptic peptides was performed using an Agilent 1100 HPLC system and Thermo-Electron LTQ ion trap mass spectrometer. The HPLC system was equipped with a Polaris C18-A column (5 μm, 4.6×250 mm, Varian) connected to a UV detector followed by the mass spectrometer. The HPLC system used two different mobile phases: mobile phase A (0.02% TFA in water) and mobile phase B (0.02% TFA in acetonitrile.) The peptides were eluted using a gradient of 0-20% mobile phase B over 70 min and 20-36% over 90 min at a flow rate of 0.7 mL/min. The eluted peptides were monitored using two different orthogonal detection systems: UV detection at 220 nm and LCQ mass spectrometer detection in positive ion mode. The mass spectrometer was operated in data-dependent "triple play" mode with dynamic exclusion enabled. In this mode, the instrument continuously acquired full scan mass spectra (m/z 300-2000). When the signal exceeded a predefined threshold, a high resolution "zoom scan" and an MS/MS scan were acquired.

To obtain the exact mass of the thioether linked and disulfide linked peptides, the Lys-C digest was analyzed using ThermoElectron LTQ interfaced with Fourier-transform ion cyclotron resonance mass spectrometer (FTMS).

Figure 3:
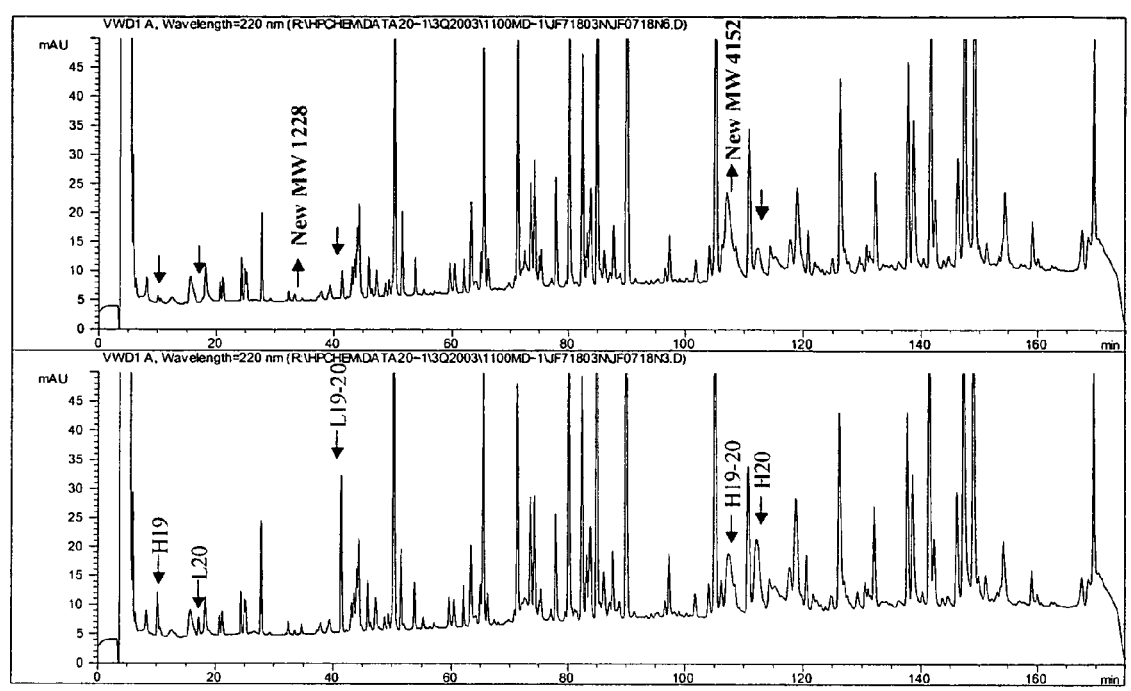
FIG. 3 shows tryptic peptide map profiles of the early-eluting SEC fraction (top panel) and unfractionated monoclonal antibody (bottom panel).

The SEC fraction was digested and analyzed by tryptic peptide mapping with tandem mass spectrometry. The peptide map profile of the early-eluting SEC fraction was compared to that of the unfractionated monoclonal antibody (FIG. 3). Because the proposed cross-linked species is a half-antibody, its peptide map profile should be equivalent to the peptide map profile of the monoclonal antibody and any differences should reveal the modification site. In the peptide map profile of the SEC fraction (FIG. 3, top panel), the tryptic peptides H19, H20, L20 and L19-L20 were significantly reduced, while two new peptides with molecular weights of 1228 and 4152, respectively, were observed. The peptides that decreased in intensity, H19 (SCDK) and L19-L20 (SFNRGEC), may explain the observed molecular mass of 1228, which corresponded to a cross-linked peptide between L19-L20 and H19, with the loss of 32 Da. The molecular mass of 4152 corresponds to a cross-linked peptide SFNRGEC-SCDKTHTCPPCPAPELLGGPSVFLFPPKPK (L19-L20 and H19-H20), with the loss of 32 Da. Because the SEC fraction was collected after a reduction step, these two cross-linked peptides contained non-reducible linkages. The loss of 32 Da may reflect the loss of one sulfur residue from the disulfide bond between the Cys residue on the heavy chain peptide H19 (SCDK) and the C-terminal Cys residue on the light chain peptide L20 (GEC), which could explain why the two cross-linked peptides could not be reduced. The mass assignments were confirmed by tandem mass spectrometry.

6.1.4.3. Location of the Thioether Linkage Between the Light and Heavy Chain

The tandem mass spectrometric analysis of the new tryptic peptides provided convincing evidence of the exact location of modification. The fragment mass spectrum (MS/MS) of the doubly charged ion at m/z $615.6^{+2}$ (L19-L20 and H19) is shown in FIG. 4A. The numbering system used was described by Roepstorff and Fohlman (20). Masses of the C-terminal fragment y series, $y_1$ to $y_7$, are consistent with the fragments from the peptide SFNRGEC attached with SCDK by a thioether link (loss of a sulfur from the disulfide bond) between the two cysteines. The masses of the N-terminal fragment b series of the peptide SFNRGEC, $b_1$ to $b_6$, and the fragment ion series from the peptide SCDK, $b^h_1$ to $b^h_4$ and $y^h_1$ to $y^h_4$, support the thioether link between the two cysteine residues of SFNRGEC and SCDK. There are also some fragment ions resulting from the linkage breakdown between two peptides ($e_7$-$SH_2$, $e^h_2$-$SH_2$, $e_7$, and $e^h_2$), and the a, c and x ion series in the MS/MS spectra. The MS/MS spectrum of H19-20 and H19-20 also supported the thioether linkage between H19-20 and L19-20 (not shown). Therefore, the modified species of the monoclonal antibody are the heavy and light chains cross-linked by a non-reducible thioether bond between Cys-223 of the heavy chain and the C-terminal Cys residue of the light chain (FIG. 1C).

6.1.4.4. Molecular Mass Determination of the Fab Fragment

Figure 5:
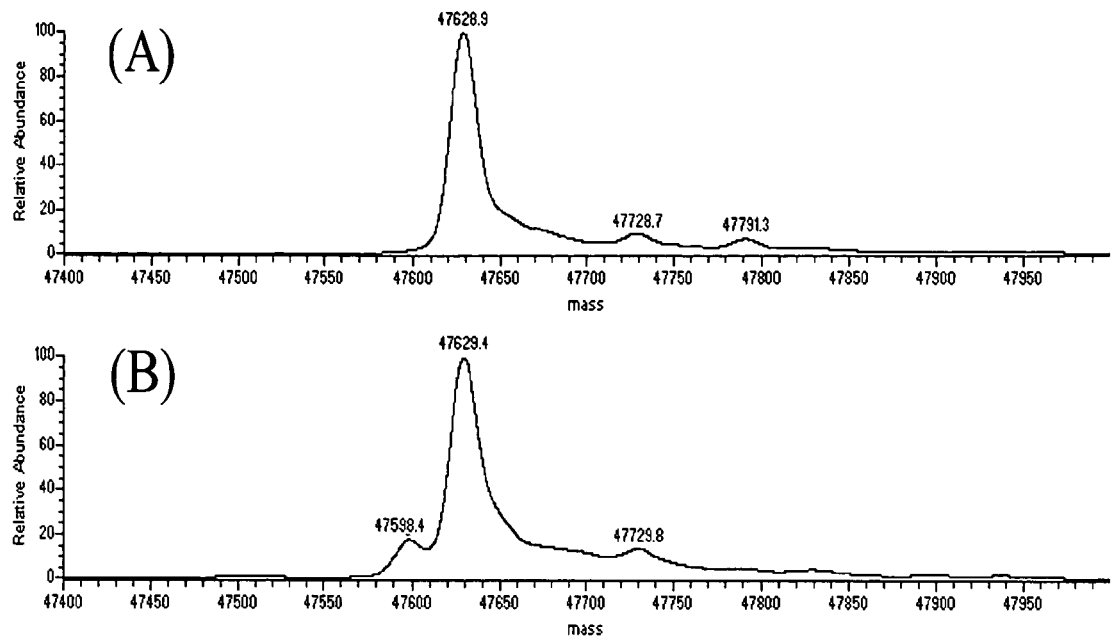

To further demonstrate that the disulfide bond modification was not an artifact resulting from sample preparation under the gel electrophoresis reducing conditions, the modification site was verified using non-reduced conditions. It was found that the 92 kDa band in the rCGE increased with time during incubation at 40° C. After 5.5 months of storage at 40° C., about 8% of the 92 kDa band had formed by rCGE analysis. To make the analysis easier, a monoclonal antibody stored at either 4° C. (control) or at 40° C. (heat-stressed) was digested by papain to generate Fab fragments. The Fab fragments were purified by a Protein L affinity column (specific to the antibody light chain). The molecular weights of two Fab fragments were then determined by LC-MS (FIG. 5).

The most intense ion in the deconvoluted mass spectra of both the control and stressed monoclonal antibodies (FIG. 5, m/z 47628.9 and 47629.4) agreed with the theoretical molecular mass 47626 for the Fab fragment consisting of the intact light chain linked to the heavy chain fragment (1-227) through a disulfide bond. The molecular mass measurement by LC-MS has a variation of ±3 Da. For the heat-stressed antibody (FIG. 5B), a minor component with an m/z of 47598.4 Da, which was 31 Da less than the mass of the major component (m/z at 47629.4 Da) was also observed. This mass was in agreement with a thioether bond linkage between Cys-213 of the light chain and Cys-233 of the heavy chain in the Fab fragment. Based on the ion intensity, the relative percentage of the thioether-linked Fab (47598.4 Da) is 14.5% for the heat-stressed antibody. Thus, the data supports that the thioether linkage existed in the monoclonal antibody under non-reduced conditions.

6.1.5 Confirmation of the Thioether Linkage under Non-Reduced Conditions

To identify the location of the thioether link, the Fab fragments of the control and heat-stressed antibodies were digested by Lys-C under non-reducing conditions and analyzed by reversed phase HPLC followed by on-line tandem mass spectrometric analysis on a LTQ ion trap instrument. A peptide with a m/z of 1260.4 Da was identified in the Lys-C digest of both control and heated-stressed antibodies, which was in agreement with the expected disulfide bond-linked peptide SFNRGEC-SCDK (data not shown). This is consistent with the molecular mass of the major component of the Fab fragments. Another peptide with an m/z at 1228.4 Da (32 Da less) and earlier retention time was identified in the Lys-C digest of both the control and heated-stressed antibodies, which was in agreement with the thioether-linked peptide SFNRGEC-SCDK. This is consistent with the molecular mass of the minor thioether-linked Fab for the heat-stressed antibody. The relative percent of the thioether-linked peptide was dramatically different between the control and heat-stressed antibodies. The thioether linked peptide was 13.6% for heat-stressed antibody, but only 0.4% for the antibody stored at 4° C. In the mass spectrum of the intact Fab of the control antibody, no visible ion corresponding to the thioether-linked Fab was observed, which was attributed to its low percentage and unit resolution of LTQ in full scan mode.

FIG. 4 shows the direct comparison of the tandem mass spectra of the peptide SFNRGEC-SCDK linked by a disulfide bond and a thioether bond, which were found in both tryptic and Lys-C digests. The fragment ions involving the thioether linkage, such as $y_1$-$y_7$, $b_7$, $y^h_3$-$y^h_4$, $b^h_2$-$b^h_4$, $c^h_2$, and $c^h_3$, are 32 Da less than the corresponding ions involving the disulfide bond linkage. On the other hand, the fragment ions not involving the thioether or disulfide linkage, such as $b_1$-$b_6$ and $y^h_2$, have the same masses for both peptides. For the fragment ions resulting from the linkage breakdown between two peptides, the disulfide-linked peptide has two additional ions, $e_7$+S and $e^h_2$+S, due to the extra sulfur residue, while the other four fragment ions $e_7$-$SH_2$, $e^h_2$-$SH_2$, $e_7$, and $e^h_2$, are common to both disulfide-linked and thioether-linked peptides. This direct comparison further provides the evidence for the thioether linkage between the peptides SFNRGEC and SCDK.

This example illustrates that a novel, non-reducible thioether bridge between the heavy and light chains of IgG1 monoclonal antibodies is the source of a band with an apparent molecular weight of 92 kDa in reducing rCGE and SDS-PAGE analysis. The analysis of the SEC fraction and the Fab fragment of a monoclonal antibody conclusively proved that the heavy and light chains were cross-linked by a non-reducible thioether bond between Cys-223 of the heavy chain and the C-terminal Cys residue of the light chain (Cys-213). The data support that the thioether linkage existed in the non-stressed monoclonal antibody, and its content increased with the duration of incubation at 40° C.

7. EQUIVALENTS

Those skilled in the art will recognize, or be able to ascertain using no more than routine experimentation, many equivalents to the specific embodiments of the invention described herein. Such equivalents are intended to be encompassed by the following claims. All publications, patents and patent applications mentioned in this specification are herein incorporated by reference into the specification to the same extent as if each individual publication, patent or patent application was specifically and individually indicated to be incorporated herein by reference.

What claimed is:

1. A composition substantially free of a denaturing reagent comprising a monoclonal antibody population and a carrier, wherein each monoclonal antibody in the population comprises the same amino acid sequence, wherein about 0.05%-4% of said population comprises one or multiple thioether cross-link, wherein the thioether cross-link links a heavy chain of the monoclonal antibody and a light chain of the monoclonal antibody, wherein the monoclonal antibody is capable of specifically binding to a respiratory syncytial virus (RSV) antigen provided that the monoclonal antibody is not palivizumab, and wherein said monoclonal antibody population is an IgG$_1$.

2. The composition of claim 1, wherein less than 2%, 1%, 0.75%, 0.5%, 0.25%, or 0.1% of said population comprises at least one thioether cross-link.

3. The composition of claim 1, wherein the monoclonal antibody population is a population of a human antibody, a chimeric antibody, and/or a humanized antibody.

4. The composition of claim 1, wherein said about 0.05%-4% of said population comprises multiple thioether cross-links.

5. The composition of claim 1, wherein the thioether cross-link is in the Fab portion or the Fc portion of the antibody.

6. The composition of claim 1, wherein the thioether cross-link links a cysteine residue of the heavy chain and a residue of the light chain.

7. The composition of claim 1, wherein the thioether links a residue of the heavy chain and a cysteine residue of the light chain of the antibody.

8. The composition of claim 1, wherein the thioether cross-link links a cysteine residue of the heavy chain and a cysteine residue of the light chain.

9. The composition of claim 7, wherein the thioether cross-link links a cysteine residue in the $C_H1$ region of the heavy chain and a cysteine residue in the $C_L$ region of the light chain.

10. The composition of claim 9, wherein the cysteine residue in the $C_H1$ region of the heavy chain is at the amino acid position 223 according to the Kabat numbering system.

11. The composition of claim 9, wherein the cysteine residue in the $C_L$ region of the light chain is at the amino acid position 213 according to the Kabat numbering system.

12. The composition of claim 1, wherein the carrier is water.

13. The composition of claim 1, wherein the monoclonal antibody is motavizumab.

14. The composition of claim 1, wherein the thioether crosslink is lanthionine.

15. The composition of claim 8, wherein the cysteine residue in the $C_H1$ region of the heavy chain is at the amino acid position 223 according to the Kabat numbering system, and the cysteine residue in the $C_L$ region of the heavy chain is at the amino acid position 213 according to the Kabat numbering system.

16. The composition of claim 15, wherein the monoclonal antibody is motavizumab.

* * * * *